US011892286B2

(12) United States Patent
Connor

(10) Patent No.: US 11,892,286 B2
(45) Date of Patent: Feb. 6, 2024

(54) MOTION RECOGNITION CLOTHING [TM] WITH AN ELECTROCONDUCTIVE MESH

(71) Applicant: Robert A. Connor, St. Paul, MN (US)

(72) Inventor: Robert A. Connor, St. Paul, MN (US)

(73) Assignee: Medibotics LLC, St. Paul, MN (US)

( * ) Notice: Subject to any disclaimer, the term of this patent is extended or adjusted under 35 U.S.C. 154(b) by 119 days.

(21) Appl. No.: 17/721,866

(22) Filed: Apr. 15, 2022

(65) Prior Publication Data

US 2022/0244032 A1 Aug. 4, 2022

Related U.S. Application Data

(63) Continuation-in-part of application No. 17/356,377, filed on Jun. 23, 2021, now Pat. No. 11,304,628, which is a continuation-in-part of application No. 16/751,245, filed on Jan. 24, 2020, now Pat. No. 11,071,498, which is a continuation-in-part of application No. 16/017,439, filed on Jun. 25, 2018, now Pat. No. 10,921,886, and a continuation-in-part of application No. 16/010,448, filed on Jun. 16, 2018, now Pat. No. 10,602,965, said application No. 16/010,448 is a continuation-in-part of application No. 15/227,254, filed on Aug. 3, 2016, now Pat. No. 10,321,873, which is a continuation-in-part of application No. 15/702,081, filed on Sep. 12, 2017, now Pat. No. 10,716,510, said application No. 16/751,245 is a continuation-in-part of application No. 15/702,081, filed on Sep. 12, 2017, said application No. 16/010,448 is a continuation-in-part of application No. 15/130,995, filed on Apr. 17, 2016, now Pat. No. 9,891,718, and a continuation-in-part of application No. 15/079,447, filed on Mar. 24, 2016, now Pat. No. 10,234,934, said application No. 16/017,439 is a continuation-in-part of application No. 14/795,373, filed on Jul. 9, 2015, said application No. 15/227,254 is a continuation-in-part of application No. 14/664,832, filed on Mar. 21, 2015, (Continued)

(51) Int. Cl.
*G01B 7/00* (2006.01)
*G01B 7/16* (2006.01)
*A41D 1/00* (2018.01)

(52) U.S. Cl.
CPC .............. *G01B 7/18* (2013.01); *A41D 1/002* (2013.01)

(58) Field of Classification Search
CPC .................................. G01B 7/18; A41D 1/002
USPC ......................................................... 73/127
See application file for complete search history.

(56) References Cited

U.S. PATENT DOCUMENTS 6,145,551 A   11/2000   Jayaraman et al.
6,315,009 B1  11/2001   Jayaraman et al.
(Continued)

*Primary Examiner* — Max H Noori

(57) ABSTRACT

This invention is Motion Recognition Clothing™ which measures the motion and/or configuration of a person's body using an energy-conducting mesh with a plurality of energy pathways. Energy input components direct energy into the pathways at a first set of locations. Energy sensors measure energy flow through the energy pathways from a second set of locations. As the person's body moves, the mesh stretches, elongates, and/or twists, which changes the flows of energy through pathways. These changes are then analyzed to estimate the motion and/or configuration of the person's body.

2 Claims, 7 Drawing Sheets

Related U.S. Application Data now Pat. No. 9,582,072, which is a continuation-in-part of application No. 14/736,652, filed on Jun. 11, 2015, said application No. 14/795,373 is a continuation-in-part of application No. 14/736,652, filed on Jun. 11, 2015, said application No. 15/079,447 is a continuation-in-part of application No. 14/463,741, filed on Aug. 20, 2014, now Pat. No. 9,588,582, which is a continuation-in-part of application No. 14/664,832, filed on Mar. 21, 2015, now Pat. No. 9,582,072, said application No. 15/227,254 is a continuation-in-part of application No. 14/463,741, filed on Aug. 20, 2014.

(60) Provisional application No. 62/797,266, filed on Jan. 26, 2019, provisional application No. 62/683,237, filed on Jun. 11, 2018, provisional application No. 62/538,793, filed on Jul. 30, 2017, provisional application No. 62/449,735, filed on Jan. 24, 2017, provisional application No. 62/357,957, filed on Jul. 2, 2016, provisional application No. 62/187,906, filed on Jul. 2, 2015, provisional application No. 62/182,473, filed on Jun. 20, 2015, provisional application No. 62/150,886, filed on Apr. 22, 2015, provisional application No. 62/100,217, filed on Jan. 6, 2015, provisional application No. 62/086,053, filed on Dec. 1, 2014, provisional application No. 62/065,032, filed on Oct. 17, 2014, provisional application No. 62/014,747, filed on Jun. 20, 2014, provisional application No. 61/976,650, filed on Apr. 8, 2014, provisional application No. 61/878,893, filed on Sep. 17, 2013.

(56) References Cited

U.S. PATENT DOCUMENTS

| | | |
|---|---|---|
| 6,381,482 B1 | 4/2002 | Jayaraman et al. |
| 6,487,906 B1 | 12/2002 | Hock |
| 6,687,523 B1 | 2/2004 | Jayaramen et al. |
| 6,970,731 B1 | 11/2005 | Jayaraman et al. |
| 7,771,318 B2 | 8/2010 | Narayanaswami |
| 7,850,574 B2 | 12/2010 | Narayanaswami |
| 7,981,057 B2 | 7/2011 | Stewart |
| 8,162,857 B2 | 4/2012 | Lanfermann et al. |
| 8,291,779 B2 | 10/2012 | Helmer et al. |
| 8,348,865 B2 * | 1/2013 | Jeong ............... A63B 24/0003 600/595 |
| 8,945,328 B2 | 2/2015 | Longinotti-Buitoni et al. |
| 8,948,839 B1 | 2/2015 | Longinotti-Buitoni et al. |
| 9,043,004 B2 | 5/2015 | Casillas et al. |
| 9,322,121 B2 | 4/2016 | Dunne et al. |
| 9,498,128 B2 | 11/2016 | Jayalath et al. |
| 9,546,921 B2 | 1/2017 | McMillen et al. |
| 9,612,102 B2 | 4/2017 | Reese et al. |
| 9,652,101 B2 | 5/2017 | McMillen |
| 9,696,833 B2 | 7/2017 | McMillen |
| 9,700,238 B2 | 7/2017 | Stewart |
| 9,710,060 B2 | 7/2017 | McMillen et al. |
| 9,753,568 B2 | 9/2017 | McMillen |
| 9,797,791 B2 | 10/2017 | Vogt et al. |
| 9,816,799 B2 | 11/2017 | Keller et al. |
| 9,816,800 B2 | 11/2017 | O'Brien et al. |
| 9,817,440 B2 | 11/2017 | Longinotti-Buitoni et al. |
| 9,839,394 B2 | 12/2017 | Casillas et al. |
| 9,841,330 B2 | 12/2017 | Casillas et al. |
| 9,850,600 B2 | 12/2017 | Gal |
| 9,874,431 B2 | 1/2018 | Reese |
| 9,885,621 B2 | 2/2018 | Dunne et al. |
| 9,913,611 B2 | 3/2018 | Wiebe et al. |
| 9,965,076 B2 | 5/2018 | McMillen |
| 9,986,771 B2 | 6/2018 | Longinotti-Buitoni et al. |
| 10,045,439 B2 | 8/2018 | Longinotti-Buitoni et al. |
| 10,065,074 B1 | 9/2018 | Hoang et al. |
| 10,067,007 B2 | 9/2018 | Keller et al. |
| 10,105,098 B2 | 10/2018 | Wiebe et al. |
| 10,119,208 B2 | 11/2018 | McMaster |
| 10,139,293 B2 | 11/2018 | Casillas et al. |
| 10,143,405 B2 | 12/2018 | Jayalath et al. |
| 10,159,440 B2 | 12/2018 | Longinotti-Buitoni et al. |
| 10,172,541 B2 | 1/2019 | Liao et al. |
| 10,197,459 B2 | 2/2019 | Keller et al. |
| 10,228,231 B2 | 3/2019 | O'Brien et al. |
| 10,240,265 B2 | 3/2019 | McMaster |
| 10,258,092 B2 | 4/2019 | Longinotti-Buitoni et al. |
| 10,268,315 B2 | 4/2019 | McMillen |
| 10,274,384 B2 | 4/2019 | Dunne et al. |
| 10,282,011 B2 | 5/2019 | McMillen |
| 10,288,507 B2 | 5/2019 | McMillen et al. |
| 10,292,652 B2 | 5/2019 | Berg et al. |
| 10,321,832 B2 | 6/2019 | Berg et al. |
| 10,362,958 B2 | 7/2019 | Morun et al. |
| 10,362,989 B2 | 7/2019 | McMillen et al. |
| 10,378,975 B1 | 8/2019 | Sun |
| 10,413,219 B2 | 9/2019 | Jayalath et al. |
| 10,429,928 B2 | 10/2019 | Morun et al. |
| 10,458,866 B1 | 10/2019 | Sun |
| 10,462,898 B2 | 10/2019 | Longinotti-Buitoni et al. |
| 10,488,936 B2 | 11/2019 | Baranski et al. |
| 10,502,643 B2 | 12/2019 | Keller et al. |
| 10,527,507 B2 | 1/2020 | Wood et al. |
| 10,535,278 B2 | 1/2020 | Chahine |
| 11,625,096 B2 * | 4/2023 | Matusik ............... G06F 3/014 345/173 |
| 2010/0036288 A1 | 2/2010 | Lanfermann et al. |
| 2012/0188158 A1 | 7/2012 | Tan et al. |
| 2013/0285577 A1 | 10/2013 | O'Brien et al. |
| 2014/0135593 A1 | 5/2014 | Jayalth et al. |
| 2014/0142459 A1 | 5/2014 | Jayalath et al. |
| 2014/0238151 A1 | 8/2014 | Dunne et al. |
| 2014/0238153 A1 | 8/2014 | Wood et al. |
| 2014/0240103 A1 | 8/2014 | Lake et al. |
| 2014/0240223 A1 | 8/2014 | Lake et al. |
| 2014/0318699 A1 | 10/2014 | Longinotti-Buitoni et al. |
| 2015/0040282 A1 | 2/2015 | Longinotti-Buitoni et al. |
| 2015/0123647 A1 | 5/2015 | Gisby et al. |
| 2015/0148619 A1 | 5/2015 | Berg et al. |
| 2015/0230719 A1 | 8/2015 | Berg et al. |
| 2015/0305677 A1 | 10/2015 | Berg et al. |
| 2015/0331533 A1 | 11/2015 | McMillen |
| 2015/0359455 A1 | 12/2015 | Hahami et al. |
| 2015/0359485 A1 | 12/2015 | Berg et al. |
| 2015/0364018 A1 * | 12/2015 | Mirov ............... G08B 6/00 340/407.1 |
| 2016/0033255 A1 | 2/2016 | Reese |
| 2016/0070347 A1 | 3/2016 | McMillen et al. |
| 2016/0091980 A1 | 3/2016 | Baranski et al. |
| 2016/0128632 A1 | 5/2016 | Wiebe et al. |
| 2016/0238368 A1 | 8/2016 | O'Brien et al. |
| 2016/0287175 A1 | 10/2016 | Coleman et al. |
| 2016/0305759 A1 | 10/2016 | Reese et al. |
| 2017/0035354 A1 | 2/2017 | Jayalath et al. |
| 2017/0036066 A1 | 2/2017 | Chahine |
| 2017/0038881 A1 | 2/2017 | McMillen |
| 2017/0074637 A1 | 3/2017 | Reese |
| 2017/0086711 A1 | 3/2017 | Liao et al. |
| 2017/0168567 A1 | 6/2017 | Reese et al. |
| 2017/0171965 A1 | 6/2017 | Youn et al. |
| 2017/0191819 A1 | 7/2017 | O'Brien et al. |
| 2017/0196513 A1 | 7/2017 | Longinotti-Buitoni et al. |
| 2017/0241847 A1 * | 8/2017 | Loh ............... G01L 1/18 |
| 2017/0265810 A1 | 9/2017 | Van De Vyver |
| 2017/0303853 A1 | 10/2017 | McMillen et al. |
| 2017/0347721 A1 | 12/2017 | Greenspan et al. |
| 2018/0049698 A1 | 2/2018 | Berg et al. |
| 2018/0051974 A1 | 2/2018 | O'Brien et al. |
| 2018/0067516 A1 | 3/2018 | Longinotti-Buitoni et al. |
| 2018/0279951 A1 | 10/2018 | Asnis et al. |
| 2018/0376586 A1 | 12/2018 | Longinotti-Buitoni et al. |
| 2019/0046114 A1 | 2/2019 | Bogdanovich et al. |
| 2019/0059461 A1 | 2/2019 | Walker |

(56) References Cited

U.S. PATENT DOCUMENTS

| | | |
|---|---|---|
| 2019/0117157 A1 | 4/2019 | Hu et al. |
| 2019/0132948 A1 | 5/2019 | Longinotti-Buitoni et al. |
| 2019/0145752 A1 | 5/2019 | Zhu et al. |
| 2019/0151713 A1 | 5/2019 | Berg et al. |
| 2019/0185672 A1 | 6/2019 | Boland et al. |
| 2019/0220099 A1 | 7/2019 | Baranski et al. |
| 2019/0228330 A1 | 7/2019 | Kaifosh et al. |
| 2019/0261874 A1 | 8/2019 | Berg et al. |
| 2019/0290198 A1 | 9/2019 | Belson et al. |
| 2019/0310713 A1 | 10/2019 | Wang et al. |
| 2019/0342993 A1 | 11/2019 | Ahn et al. |
| 2019/0364983 A1 | 12/2019 | Nakajima et al. |
| 2019/0390985 A1 | 12/2019 | Kwok et al. |
| 2020/0000378 A1 | 1/2020 | Jayalath et al. |
| 2020/0008715 A1 | 1/2020 | Schroeck et al. |
| 2021/0393427 A1* | 12/2021 | Mirza .................. A61B 5/6812 |
| 2023/0125796 A1* | 4/2023 | Baek ...................... G09G 3/035 345/212 |
| 2023/0148868 A1* | 5/2023 | Connor ................ A61B 5/0064 600/476 |

\* cited by examiner

MOTION RECOGNITION CLOTHING [TM] WITH AN ELECTROCONDUCTIVE MESH

CROSS-REFERENCE TO RELATED APPLICATIONS

This application is a continuation in part of patent application Ser. No. 17/356,377 filed on 2021 Jun. 23.

application Ser. No. 17/356,377 was a continuation in part of patent application Ser. No. 16/751,245 filed on 2020 Jan. 24.

application Ser. No. 16/751,245 was a continuation in part of patent application Ser. No. 16/543,056 filed on 2019 Aug. 16; claimed the priority benefit of provisional patent application 62/797,266 filed on 2019 Jan. 26; was a continuation in part of patent application Ser. No. 16/017,439 filed on 2018 Jun. 25; was a continuation in part of patent application Ser. No. 16/010,448 filed on 2018 Jun. 16; and was a continuation in part of patent application Ser. No. 15/702,081 filed on 2017 Sep. 12.

application Ser. No. 16/543,056 claimed the priority benefit of provisional patent application 62/797,266 filed on 2019 Jan. 26. application Ser. No. 16/543,056 claimed the priority benefit of provisional patent application 62/727,798 filed on 2018 Sep. 6. application Ser. No. 16/543,056 was a continuation in part of patent application Ser. No. 16/010,448 filed on 2018 Jun. 16.

application Ser. No. 16/017,439 was a continuation in part of patent application Ser. No. 16/010,448 filed on 2018 Jun. 16; claimed the priority benefit of provisional patent application 62/683,237 filed on 2018 Jun. 11; and was a continuation in part of patent application Ser. No. 14/795,373 filed on 2015 Jul. 9.

application Ser. No. 16/010,448 claimed the priority benefit of provisional patent application 62/683,237 filed on 2018 Jun. 11. application Ser. No. 16/010,448 claimed the priority benefit of provisional patent application 62/538,793 filed on 2017 Jul. 30. application Ser. No. 16/010,448 was a continuation in part of patent application Ser. No. 15/702,081 filed on 2017 Sep. 12. application Ser. No. 16/010,448 was a continuation in part of patent application Ser. No. 15/227,254 filed on 2016 Aug. 3 which is now U.S. Pat. No. 10,321,873 issued on 2019 Jun. 18.

application Ser. No. 15/702,081 was a continuation in part of patent application Ser. No. 14/795,373 filed on 2015 Jul. 9. application Ser. No. 15/702,081 claimed the priority benefit of provisional patent application 62/538,793 filed on 2017 Jul. 30. application Ser. No. 15/702,081 claimed the priority benefit of provisional patent application 62/449,735 filed on 2017 Jan. 24. application Ser. No. 15/702,081 was a continuation in part of patent application Ser. No. 15/227,254 filed on 2016 Aug. 3 which is now U.S. Pat. No. 10,321,873 issued on 2019 Jun. 18.

application Ser. No. 15/227,254 claimed the priority benefit of provisional patent application 62/357,957 filed on 2016 Jul. 2. application Ser. No. 15/227,254 was a continuation in part of patent application Ser. No. 14/736,652 filed on 2015 Jun. 11. application Ser. No. 15/227,254 was a continuation in part of patent application Ser. No. 14/664,832 filed on 2015 Mar. 21 which is now U.S. Pat. No. 9,582,072 issued on 2017 Feb. 28. application Ser. No. 15/227,254 was a continuation in part of patent application Ser. No. 15/130,995 filed on 2016 Apr. 17 which is now U.S. Pat. No. 9,891,718 issued on 2018 Feb. 13. application Ser. No. 15/227,254 was a continuation in part of patent application Ser. No. 15/079,447 filed on 2016 Mar. 24 which is now U.S. Pat. No. 10,234,934 issued on 2019 Mar. 19.

application Ser. No. 15/130,995 claimed the priority benefit of provisional patent application 62/150,886 filed on 2015 Apr. 22. application Ser. No. 15/079,447 claimed the priority benefit of provisional patent application 62/150,886 filed on 2015 Apr. 22. application Ser. No. 15/079,447 was a continuation in part of patent application Ser. No. 14/664,832 filed on 2015 Mar. 21 which is now U.S. Pat. No. 9,582,072 issued on 2017 Feb. 28. application Ser. No. 15/079,447 was a continuation in part of patent application Ser. No. 14/463,741 filed on 2014 Aug. 20 which is now U.S. Pat. No. 9,588,582 issued on 2017 Mar. 7.

application Ser. No. 14/795,373 claimed the priority benefit of provisional patent application 62/187,906 filed on 2015 Jul. 2. application Ser. No. 14/795,373 claimed the priority benefit of provisional patent application 62/182,473 filed on 2015 Jun. 20. application Ser. No. 14/795,373 claimed the priority benefit of provisional patent application 62/086,053 filed on 2014 Dec. 1. application Ser. No. 14/795,373 claimed the priority benefit of provisional patent application 62/065,032 filed on 2014 Oct. 17. application Ser. No. 14/795,373 was a continuation in part of patent application Ser. No. 14/736,652 filed on 2015 Jun. 11.

application Ser. No. 14/736,652 claimed the priority benefit of provisional patent application 62/100,217 filed on 2015 Jan. 6. application Ser. No. 14/736,652 claimed the priority benefit of provisional patent application 62/014,747 filed on 2014 Jun. 20. application Ser. No. 14/736,652 was a continuation in part of patent application Ser. No. 14/664,832 filed on 2015 Mar. 21 which is now U.S. Pat. No. 9,582,072 issued on 2017 Feb. 28. application Ser. No. 14/664,832 claimed the priority benefit of provisional patent application 61/976,650 filed on 2014 Apr. 8. application Ser. No. 14/664,832 was a continuation in part of patent application Ser. No. 14/463,741 filed on 2014 Aug. 20 which is now U.S. Pat. No. 9,588,582 issued on 2017 Mar. 7. application Ser. No. 14/463,741 claimed the priority benefit of provisional patent application 61/878,893 filed on 2013 Sep. 17.

The entire contents of these applications are incorporated herein by reference.

FEDERALLY SPONSORED RESEARCH

Not Applicable

SEQUENCE LISTING OR PROGRAM

Not Applicable

BACKGROUND

Field of Invention

This invention relates to devices and methods for human motion capture.

Introduction

There are several advantages of Motion Recognition Clothing™ as compared to camera-based, exoskeleton-based, or goniometer-based methods of motion capture. Motion Recognition Clothing™ is not constrained to a particular location, is not limited by optical occlusion, does not constrain or hinder body motion, can be unobtrusively integrated into clothing, has a low set-up time, and can be more accurate in measuring body joint motion than devices in the prior art. Full-body Motion Recognition Clothing™ can enable minimally-intrusive, ambulatory, full-body motion capture that does not confine a person to a narrow location in front of a camera. Such Motion Recognition Clothing™ opens up opportunities for full-body motion capture of outdoor and large-scale activities such as playing golf, running, swimming, playing soccer and playing basketball. Motion Recognition Clothing™ also has several medical applications, including range of motion analysis for body joints for medical diagnosis and physical therapy.

Review of the Relevant Art

Myant is a significant innovator with respect to clothing for human motion capture. Their work includes U.S. Pat. No. 10,535,278 (Chahine, Jan. 14, 2020, "Garment with Stretch Sensors") and U.S. patent application publication 20170036066 (Chahine, Feb. 9, 2017, "Garment with Stretch Sensors") which disclose a knitted or woven garment configured for sensing movement of an adjacent underlying body portion of a wearer of the garment via one or more sensors.

Another significant innovator with respect to clothing for human motion capture is L.I.F.E. Corporation. Their work includes U.S. Pat. No. 10,045,439 (Longinotti-Buitoni et al., Aug. 7, 2018, "Garments Having Stretchable and Conductive Ink"), U.S. Pat. No. 10,258,092 (Longinotti-Buitoni et al., Apr. 16, 2019, "Garments Having Stretchable and Conductive Ink"), U.S. Pat. No. 8,945,328 (Longinotti-Buitoni et al., Feb. 3, 2015, "Methods of Making Garments Having Stretchable and Conductive Ink"), U.S. Pat. No. 8,948,839 (Longinotti-Buitoni et al., Feb. 3, 2015, "Compression Garments Having Stretchable and Conductive Ink"), U.S. Pat. No. 9,817,440 (Longinotti-Buitoni et al., Nov. 14, 2017, "Garments Having Stretchable and Conductive Ink"), and U.S. Pat. No. 9,986,771 (Longinotti-Buitoni et al., Jun. 5, 2018, "Garments Having Stretchable and Conductive Ink"); and U.S. patent application publications 20180067516 (Longinotti-Buitoni et al., Mar. 8, 2018, "Garments Having Stretchable and Conductive Ink"), 20180376586 (Longinotti-Buitonii et al., Dec. 27, 2018, "Garments Having Stretchable and Conductive Ink"), 20170196513 (Longinotti-Buitoni et al., Jul. 13, 2017, "Garments Having Stretchable and Conductive Ink"), 20150040282 (Longinotti-Buitoni et al., Feb. 12, 2015, "Compression Garments Having Stretchable and Conductive Ink"), and 20140318699 (Longinotti-Buitoni et al., Oct. 30, 2014, "Methods of Making Garments Having Stretchable and Conductive Ink"), which disclose garments with stretchable conductive ink patterns. U.S. Pat. No. 10,159,440 (Longinotti-Buitoni et al., Dec. 25, 2018, "Physiological Monitoring Garments") and U.S. Pat. No. 10,462,898 (Longinotti-Buitoni et al., Oct. 29, 2019, "Physiological Monitoring Garments"), and U.S. patent application publication 20190132948 (Longinotti-Buitonii et al., May 2, 2019, "Physiological Monitoring Garments") disclose garments for detecting and monitoring physiological parameters such as respiration and cardiac parameters.

Another significant innovator with respect to clothing for human motion capture is StretchSense. Their work includes patent application publication 20130285577 (O'Brien et al., Oct. 31, 2013, "Dielectric Elastomer Self-Sensing Using Plane Approximation") which discloses a method for obtaining feedback parameters related to the state of a dielectric elastomer (DE). U.S. patent application publication 20170191819 (O'Brien et al., Jul. 6, 2017, "Electro-Mechanical Sensor") discloses an electrical sensor having an electrical capacitance which varies with mechanical deformation. U.S. Pat. No. 10,228,231 (O'Brien et al., Mar. 12, 2019, "Laminated Devices of Elastic Material Suitable for Dielectric Elastomer Sensing") discloses a laminated device of flexible and compliant layers of material, such as used to provide a dielectric elastomer sensor. U.S. Pat. No. 9,816,800 (O'Brien et al., Nov. 14, 2017, "Method of Fabrication of Laminates of Elastic Material Suitable for Dielectric Elastomer Sensing"), and U.S. patent application publications 20160238368 (O'Brien et al., Aug. 18, 2016, "Method of Fabrication of Laminates of Elastic Material Suitable for Dielectric Elastomer Sensing") and 20180051974 (O'Brien et al., Feb. 22, 2018, "Method of Fabrication of Laminates of Elastic Material Suitable for Dielectric Elastomer Sensing"), disclose a method of fabricating a laminate of flexible and compliant layers of material, such as used to provide a dielectric elastomer sensor. U.S. patent application publication 20150123647 (Gisby et al., May 7, 2015, "Self-Sensing Dielectric Elastomer Device") discloses circuits, systems and methods for dielectric elastomer device (DED) self-sensing.

Another significant innovator with respect to clothing for human motion capture is BeBop Sensors. Their work includes U.S. Pat. No. 9,753,568 (McMillen, Sep. 5, 2017, "Flexible Sensors and Applications") and U.S. Pat. No. 10,282,011 (McMillen, May 7, 2019, "Flexible Sensors and Applications"), and also U.S. patent application publications 20150331533 (McMillen, Nov. 19, 2015, "Flexible Sensors and Applications") and 20170038881 (McMillen, Feb. 9, 2017, "Flexible Sensors and Applications") which disclose wearable sensors with piezoresistive materials. U.S. Pat. No. 9,965,076 (McMillen, May 8, 2018, "Piezoresistive Sensors and Applications"), U.S. Pat. No. 9,546,921 (McMillen et al., Jan. 17, 2017, "Piezoresistive Sensors and Sensor Arrays"), U.S. Pat. No. 10,288,507 (McMillen et al., May 14, 2019, "Piezoresistive Sensors and Sensor Arrays"), and U.S. Pat. No. 9,696,833 (McMillen, Jul. 4, 2017, "Promoting Sensor Isolation and Performance in Flexible Sensor Arrays") disclose sensors with conductive traces on piezoresistive material with musical applications. U.S. Pat. No. 9,710,060 (McMillen et al., Jul. 18, 2017, "Sensor System Integrated with a Glove") and U.S. Pat. No. 10,362,989 (McMillen et al., Jul. 30, 2019, "Sensor System Integrated with a Glove"), and U.S. patent application publications 20160070347 (McMillen et al., Mar. 10, 2016, "Sensor System Integrated with a Glove") and 20170303853 (McMillen et al., Oct. 26, 2017, "Sensor System Integrated with a Glove") disclose sensor systems with piezoresistive material in gloves to measure hand motion. U.S. Pat. No. 9,652,101 (McMillen, May 16, 2017, "Two-Dimensional Sensor Arrays") and U.S. Pat. No. 10,268,315 (McMillen, Apr. 23, 2019, "Two-Dimensional Sensor Arrays") disclose two-dimensional sensor arrays made with piezoresistive material.

Another significant innovator with respect to clothing for human motion capture is Nike. Their work includes U.S. Pat. No. 9,043,004 (Casillas et al., May 26, 2015, "Apparel Having Sensor System"), U.S. Pat. No. 9,839,394 (Casillas et al., Dec. 12, 2017, "Apparel Having Sensor System"), U.S. Pat. No. 9,841,330 (Casillas et al., Dec. 12, 2017, "Apparel Having Sensor System"), and U.S. Pat. No. 10,139,293 (Casillas et al., Nov. 27, 2018, "Apparel Having Sensor System") which disclose a plurality of sensors formed of a polymeric material having a conductive particulate material dispersed therein and conductive leads connecting the sensors to a port. U.S. patent application publication 20190059461 (Walker, Feb. 28, 2019, "Sense- Enabled Apparel") discloses an apparel piece sized to be worn on a user and a sensor system integrated with the apparel piece.

Another significant innovator with respect to clothing for human motion capture is Mad Apparel (Athos). Their work includes patent application publication 20150305677 (Berg et al., Oct. 29, 2015, "Biometric Electrode System and Method of Manufacture") which discloses an electrode system for EMG sensors with a substrate comprising a reference region and a signal communication region. U.S. patent application publication 20150359485 (Berg et al., Dec. 17, 2015, "Biometric Signal Conduction System and Method of Manufacture") discloses EMG sensors with a flexible substrate including a first broad surface and a second broad surface opposing the first broad surface. U.S. Pat. No. 9,913,611 (Wiebe et al., Mar. 13, 2018, "Garment Integrated Sensing System and Method") and U.S. Pat. No. 10,105,098 (Wiebe et al., Oct. 23, 2018, "Garment Integrated Sensing System and Method"), and U.S. patent application publication 20160128632 (Wiebe et al., May 12, 2016, "Garment Integrated Sensing System and Method"), disclose wireless sensor interfaces coupled to a garment, wherein each sensor includes an electrode layer, a positional identifier, and a retention subsystem. U.S. patent application publication 20180049698 (Berg et al., Feb. 22, 2018, "Garment with Conductive Thread Exposed on Both Sides") discloses a garment made by bonding an adhesive to a first layer of fabric and a second layer of fabric. U.S. patent application publication 20180279951 (Asnis et al., Oct. 4, 2018, "Movement Compensation for Sensor-Equipped Athletic Garments") discloses an athletic garment includes connective segments that compensate for motion of an athlete wearing the athletic garment. U.S. patent application publication 20190151713 (Berg et al., May 23, 2019, "Printable Electronic Garment Conduit") discloses an athletic garment with printed EMG sensors. U.S. Pat. No. 10,292,652 (Berg et al., May 21, 2019, "System and Method for Monitoring Biometric Signals") and U.S. Pat. No. 10,321,832 (Berg et al., Jun. 18, 2019, "System and Method for Monitoring Biometric Signals"), and U.S. patent application publications 20150148619 (Berg et al., May 28, 2015, "System and Method for Monitoring Biometric Signals"), 20150230719 (Berg et al., Aug. 20, 2015, "System and Method for Monitoring Biometric Signals"), and 20190261874 (Berg et al., Aug. 29, 2019, "System and Method for Monitoring Biometric Signals") disclose a garment with a mounting module having an array of connection regions and biometric sensors. U.S. Pat. No. 9,498,128 (Jayalath et al., Nov. 22, 2016, "Wearable Architecture and Methods for Performance Monitoring, Analysis, and Feedback") and U.S. Pat. No. 10,413,219 (Jayalath et al., Sep. 17, 2019, "Wearable Architecture and Methods for Performance Monitoring, Analysis, and Feedback"), and U.S. patent application publications 20140135593 (Jayalth et al., May 15, 2014, "Wearable Architecture and Methods for Performance Monitoring, Analysis, and Feedback"), 20170035354 (Jayalath et al., Feb. 9, 2017, "Wearable Architecture and Methods for Performance Monitoring, Analysis, and Feedback"), and 20200000378 (Jayalath et al., Jan. 2, 2020, "Wearable Architecture and Methods for Performance Monitoring, Analysis, and Feedback"), disclose techniques, fabrics, materials, systems, sensors, EMG sensors, circuitry, algorithms and methods for wearable monitoring devices and associated exercise devices. U.S. Pat. No. 10,143,405 (Jayalath et al., Dec. 4, 2018, "Wearable Performance Monitoring, Analysis, and Feedback Systems and Methods") and U.S. patent application publication 20140142459 (Jayalath et al., May 22, 2014, "Wearable Performance Monitoring, Analysis, and Feedback Systems and Methods") disclose techniques, systems, sensors, circuitry, algorithms and methods for wearable monitoring devices.

Another significant innovator with respect to clothing for human motion capture is Georgia Tech. Their work includes U.S. Pat. No. 6,381,482 (Jayaraman et al., Apr. 30, 2002, "Fabric or Garment with Integrated Flexible Information Infrastructure") which discloses a modular electronic garment. U.S. Pat. No. 6,687,523 (Jayaramen et al., Feb. 3, 2004, "Fabric or Garment with Integrated Flexible Information Infrastructure for Monitoring Vital Signs Of Infants") discloses an infant garment which ensures a snug fit for the baby so that the sensors stay in place to minimize the risk of false alarms. U.S. Pat. No. 6,970,731 (Jayaraman et al., Nov. 29, 2005, "Fabric-Based Sensor for Monitoring Vital Signs") discloses a woven or knitted fabric-based sensor for monitoring vital signs or other electrical impulses. U.S. Pat. No. 6,315,009 (Jayaraman et al., Nov. 13, 2001, "Full-Fashioned Garment with Sleeves Having Intelligence Capability") discloses a full-fashioned weaving process for the production of a woven garment which can accommodate and include sleeves. U.S. Pat. No. 6,145,551 (Jayaraman et al., Nov. 14, 2000, "Full-Fashioned Weaving Process for Production of a Woven Garment with Intelligence Capability") discloses a full-fashioned weaving process for the production of a woven garment which can accommodate and include holes.

Another significant innovator with respect to clothing for human motion capture is Thalmic Labs (North). Their work includes patent application publication 20140240223 (Lake et al., Aug. 28, 2014, "Method and Apparatus for Analyzing Capacitive EMG and IMU Sensor Signals for Gesture Control") which discloses a muscle interface device to control connected devices. U.S. patent application publication 20140240103 (Lake et al., Aug. 28, 2014, "Methods and Devices for Combining Muscle Activity Sensor Signals and Inertial Sensor Signals for Gesture-Based Control") discloses a wearable electronic EMG device for use with controllable connected devices.

Another significant innovator with respect to clothing for human motion capture is Bend Labs. Their work includes U.S. Pat. No. 9,874,431 (Reese, Jan. 23, 2018, "Angular Displacement Sensor of Compliant Material"), and U.S. patent application publications 20160033255 (Reese, Feb. 4, 2016, "Angular Displacement Sensor of Compliant Material") and 20170074637 (Reese, Mar. 16, 2017, "Angular Displacement Sensor of Compliant Material") which disclose multi-directional capacitive sensors. U.S. Pat. No. 9,612,102 (Reese et al., Apr. 4, 2017, "Compliant Multi-Region Angular Displacement and Strain Sensors"), and U.S. patent application publications 20160305759 (Reese et al., Oct. 20, 2016, "Compliant Multi-Region Angular Displacement and Strain Sensors") and 20170168567 (Reese et al., Jun. 15, 2017, "Compliant Multi-Region Angular Displacement and Strain Sensors") disclose angular displacement sensors and strain sensors multiple motion sensing regions.

Another significant innovator with respect to clothing for human motion capture is Harvard University. Their work includes U.S. Pat. No. 10,527,507 (Wood et al., Jan. 7, 2020, "Artificial Skin and Elastic Strain Sensor") and U.S. Pat. No. 9,797,791 (Vogt et al., Oct. 24, 2017, "Multi-Axis Force Sensing Soft Artificial Skin"), and U.S. patent application publication 20140238153 (Wood et al., Aug. 28, 2014, "Artificial Skin and Elastic Strain Sensor"), which disclose an elastic strain sensor with conductive fluid.

Another significant innovator with respect to clothing for human motion capture is CTRL-Labs. Their work includes patent application publication 20190228330 (Kaifosh et al., Jul. 25, 2019, "Handstate Reconstruction Based on Multiple Inputs") which discloses methods and systems for recognizing gestures using a plurality of neuromuscular sensors. U.S. Pat. No. 10,429,928 (Morun et al., Oct. 1, 2019, "Systems, Articles, and Methods for Capacitive Electromyography Sensors") and U.S. Pat. No. 10,362,958 (Morun et al., Jul. 30, 2019, "Systems, Articles, and Methods for Electromyography Sensors") disclose EMG sensors which coated with protective barriers and adapted to resistively couple to a user's skin.

Another significant innovator with respect to clothing for human motion capture is IBM. Their work includes U.S. Pat. No. 7,771,318 (Narayanaswami, Aug. 10, 2010, "Device for Monitoring a User's Posture") and U.S. Pat. No. 7,850,574 (Narayanaswami, Dec. 14, 2010, "Device for Monitoring a User's Posture") which disclose a wearable device which monitors a person's posture. U.S. patent application publication 20190117157 (Hu et al., Apr. 25, 2019, "Sensors Facilitating Monitoring of Living Entities") discloses methods of manufacturing optical strain sensors.

Another significant innovator with respect to clothing for human motion capture is Apple. Their work includes U.S. Pat. No. 10,488,936 (Baranski et al., Nov. 26, 2019, "Motion and Gesture Input from a Wearable Device"), and U.S. patent application publications 20160091980 (Baranski et al., Mar. 31, 2016, "Motion and Gesture Input from a Wearable Device") and 20190220099 (Baranski et al., Jul. 18, 2019, "Motion and Gesture Input from a Wearable Device") which disclose wearable devices with optical or EMG sensors that recognize gestures of a user's hand, arm, wrist, and fingers. U.S. patent application publication 20190310713 (Wang et al., Oct. 10, 2019, "Sensors for Electronic Finger Devices") discloses finger-mounted devices with strain sensors and/or ultrasonic sensors to measure finger movement.

Another significant innovator with respect to clothing for human motion capture is J-MEX. Their work includes U.S. Pat. No. 10,172,541 (Liao et al., Jan. 8, 2019, "Motion Recognition Device and Method") and U.S. patent application publication 20170086711 (Liao et al., Mar. 30, 2017, "Motion Recognition Device and Method") which disclose a motion recognition device with a first sense signal portion and a second sense signal portion different from the first sense signal portion.

Another significant innovator with respect to clothing for human motion capture is the University of Minnesota. Their work includes U.S. Pat. No. 9,322,121 (Dunne et al., Apr. 26, 2016, "Stitched Stretch Sensor"), U.S. Pat. No. 9,885,621 (Dunne et al., Feb. 6, 2018, "Stitched Stretch Sensor"), and U.S. Pat. No. 10,274,384 (Dunne et al., Apr. 30, 2019, "Stitched Stretch Sensor"), and U.S. patent application publication 20140238151 (Dunne et al., Aug. 28, 2014, "Stitched Stretch Sensor") which disclose a stitched sensor including a conductive thread, and the stitch geometry is configured such that an electrical property of the stitched sensor changes based on at least one of stretching, relaxation, or bending of the textile.

Another significant innovator with respect to clothing for human motion capture is Xenoma. Their work includes patent application publication 20190364983 (Nakajima et al., Dec. 5, 2019, "Wearable Device and Paper Pattern") which discloses a wearable device with sensors, at least one of which is on the front side and the back side respectively.

Another significant innovator with respect to clothing for human motion capture is Facebook. Their work includes U.S. Pat. No. 10,197,459 (Keller et al., Feb. 5, 2019, "Indexable Strain Sensor") which discloses a deformation sensing apparatus comprising an elastic substrate, a conductive element, and an additional conductive element. U.S. Pat. No. 10,502,643 (Keller et al., Dec. 10, 2019, "Resistive-Capacitive Deformation Sensor") and U.S. Pat. No. 10,067,007 (Keller et al., Sep. 4, 2018, "Resistive-Capacitive Deformation Sensor") disclose a deformation sensing apparatus which senses stain in two directions. U.S. Pat. No. 9,816,799 (Keller et al., Nov. 14, 2017, "Embroidered Strain Sensing Elements") discloses a deformation sensing fabric comprising a fabric substrate with a first fabric layer and a first conductive element woven into the first fabric layer.

Another significant innovator with respect to clothing for human motion capture is Footfalls and Heartbeats. Their work includes U.S. Pat. No. 10,119,208 (McMaster, Nov. 6, 2018, "Method for Making Electrically Conductive Textiles and Textile Sensor") which discloses a method for making a textile sensor which includes selecting yarn variables, stitch variables, and/or textile variables. U.S. Pat. No. 10,240,265 (McMaster, Mar. 26, 2019, "Method for Optimizing Contact Resistance in Electrically Conductive Textiles") discloses a method for optimizing contact resistance in electrically conductive yarns and textiles.

Another significant innovator with respect to clothing for human motion capture is Nextiles. Their work includes U.S. Pat. No. 10,458,866 (Sun, Oct. 29, 2019, "Methods of Manufacturing Devices for Static and Dynamic Body Measurements") which discloses a method of fabricating a sensor for static and dynamic body measurements. U.S. Pat. No. 10,378,975 (Sun, Aug. 13, 2019, "Systems, Methods, and Devices for Static and Dynamic Body Measurements") discloses systems and methods to measure static and dynamic forces of a body using sensors.

Other relevant art with respect to clothing for human motion capture includes the following. U.S. Pat. No. 9,850,600 (Gal, Dec. 26, 2017, "Sensor Garment and Methods of Making the Same") discloses IP sensor conductors with waveforms having legs that are substantially parallel throughout the operating range of stretch. U.S. Pat. No. 6,487,906 (Hock, Dec. 3, 2002, "Flexible Film Sensor System for Monitoring Body Motion") discloses a sequence of low force, high compliance, long extension, piezofilm-based sensors for a biofeedback system for self-monitoring of selected body motions. U.S. patent application publication 20170265810 (Van De Vyver, Sep. 21, 2017, "Elastic Sensor") discloses a stretchable sensor patch comprising an elastic film layer with a stretchability of at least 100% and at least one elastic DEAP strip.

U.S. patent application publication 20190046114 (Bogdanovich et al., Feb. 14, 2019, "Garment System Providing Biometric Monitoring") discloses a garment for monitoring biometric properties of the wearer. U.S. patent application publication 20200008715 (Schroeck et al., Jan. 9, 2020, "Rotation Monitoring System and Method") discloses a rotation monitoring system attached to a limb to identify ranges of motion associated with injuries or poor performance. U.S. patent application publication 20160287175 (Coleman et al., Oct. 6, 2016, "Sensitive, High-Strain, High-Rate, Bodily Motion Sensors Based on Conductive Nano-Material-Rubber Composites") discloses a process for producing conductive composites. U.S. patent application publication 20190185672 (Boland et al., Jun. 20, 2019, "Viscoelastic Conductive Nanomaterial-Polymer Nanocomposites and Sensing Devices Comprising the Composite Material") discloses a homogenous composite material with high strength.

U.S. Pat. No. 8,291,779 (Helmer et al., Oct. 23, 2012, "System and Garment for Detecting Movement") discloses a system for detecting movement of a limb or section of a limb. U.S. patent application publication 20150359455 (Hahami et al., Dec. 17, 2015, "Fiber Optic Shape Sensing Applications") discloses a fiber optic cable and interrogation circuitry. U.S. Pat. No. 8,348,865 (Jeong et al., Jan. 8, 2013, "Non-Intrusive Movement Measuring Apparatus and Method Using Wearable Electro-Conductive Fiber") discloses a non-intrusive movement measuring apparatus and method using wearable electro-conductive fibers. U.S. patent application publication 20170171965 (Youn et al., Jun. 15, 2017, "Stretchable Electronic Device and Method of Fabricating the Same") discloses a stretchable electronic device including a flexible substrate, a conductive fiber pattern formed on the flexible substrate, wherein the conductive fiber pattern has a repetitive circular structure.

U.S. patent application publication 20190342993 (Ahn et al., Nov. 7, 2019, "Stretchable Electronics and Method for Fabricating the Same") discloses stretchable electronics including a stretchable substrate, support patterns disposed on a surface of the stretchable substrate, and output devices disposed on the patterns. U.S. Pat. No. 10,065,074 (Hoang et al., Sep. 4, 2018~T=Training Systems with Wearable Sensors for Providing Users with Feedback") discloses a training system based on mobile technology and the kinematics of human motion which characterizes, analyzes, and supplies feedback to a user based on the user's movements. U.S. patent application publication 20120188158 (Tan et al., Jul. 26, 2012, "Wearable Electromyography-Based Human-Computer Interface") discloses a plurality of Electromyography (EMG) sensors comprising a human-computer interface (HCl) for interacting with computing systems.

U.S. Pat. No. 7,981,057 (Stewart, Jul. 19, 2011, "Joint Motion Sensing to Make a Determination of a Positional Change of an Individual") and U.S. Pat. No. 9,700,238 (Stewart, Jul. 11, 2017, "Joint Motion Sensing to Make a Determination of a Positional Change of an Individual") disclose one or more sensors that produce one or more signals based on one or more joint motions of an individual. U.S. Pat. No. 8,162,857 (Lanfermann et al., Apr. 24, 2012, "Limb Movement Monitoring System") and U.S. patent application publication 20100036288 (Lanfermann et al., Feb. 11, 2010, "Limb Movement Monitoring System") disclose a garment comprising spatially addressable photonic textiles. U.S. patent application publication 20190145752 (Zhu et al., May 16, 2019, "Highly Stretchable Strain Sensor for Human Motion Monitoring") discloses a method to assemble a highly stretchable and highly sensitive strain sensor.

U.S. patent application publication 20170347721 (Greenspan et al., Dec. 7, 2017, "Conductive Thread Stitched Stretch Sensor") discloses conductive thread stitched stretch sensors. U.S. patent application publication 20190390985 (Kwok et al., Dec. 26, 2019, "Real-Time Surface Shape Sensing for Flexible Structures") discloses a surface shape sensor in the form of a flexible and stretchable elastomeric substrate with strain/displacement sensing elements embedded in it. U.S. patent application publication 20190290198 (Belson et al., Sep. 26, 2019, "Systems and Methods for Monitoring Physical Therapy of the Knee and Other Joints") discloses systems, devices, and methods for post-surgical joint range of motion measurement, activity monitoring, as well as monitoring compliance.

SUMMARY OF THE INVENTION

Disclosed herein is Motion Recognition Clothing™ which measures the motion and/or configuration of a person's body. This Motion Recognition Clothing™ incorporates a wearable energy-conducting mesh, lattice, grid, or matrix that spans the surface of a portion of a person's body which contains a joint. The mesh, lattice, grid, or matrix further comprises a plurality of energy pathways. The clothing further includes a plurality of energy input components which direct energy into the energy pathways at a first plurality (or set) of locations and a plurality of energy sensors which measure energy flow through the energy pathways from a second plurality (or set) of locations.

As the body joint moves, the mesh, grid, lattice, or matrix bends, stretches, elongates, and/or twists. This bending, stretching, elongation, and/or twisting changes the flows of energy through different energy pathways in the mesh, grid, lattice, or matrix. These changes in energy flows can, in turn, be measured by energy sensors and analyzed together to estimate the motion and/or configuration of the body joint.

There are several advantages of Motion Recognition Clothing™ as compared to camera-based, exoskeleton-based, or goniometer-based methods of motion capture in the prior art. Motion Recognition Clothing™ is not constrained to a particular location, is not limited by optical occlusion, does not constrain or hinder body motion, can be unobtrusively integrated into clothing, has a low set-up time, and can be more accurate in measuring body joint motion than devices in the prior art. Full-body Motion Recognition Clothing™ can enable minimally-intrusive, ambulatory, full-body motion capture that does not confine a person to a narrow location in front of a camera. Such Motion Recognition Clothing™ opens up opportunities for full-body motion capture of outdoor and large-scale activities such as playing golf, running, swimming, playing soccer and playing basketball. Motion Recognition Clothing™ also has several medical applications, including range of motion analysis for body joints for medical diagnosis and physical therapy.

INTRODUCTION TO THE FIGURES

DETAILED DESCRIPTION OF THE FIGURES

Figure 1:
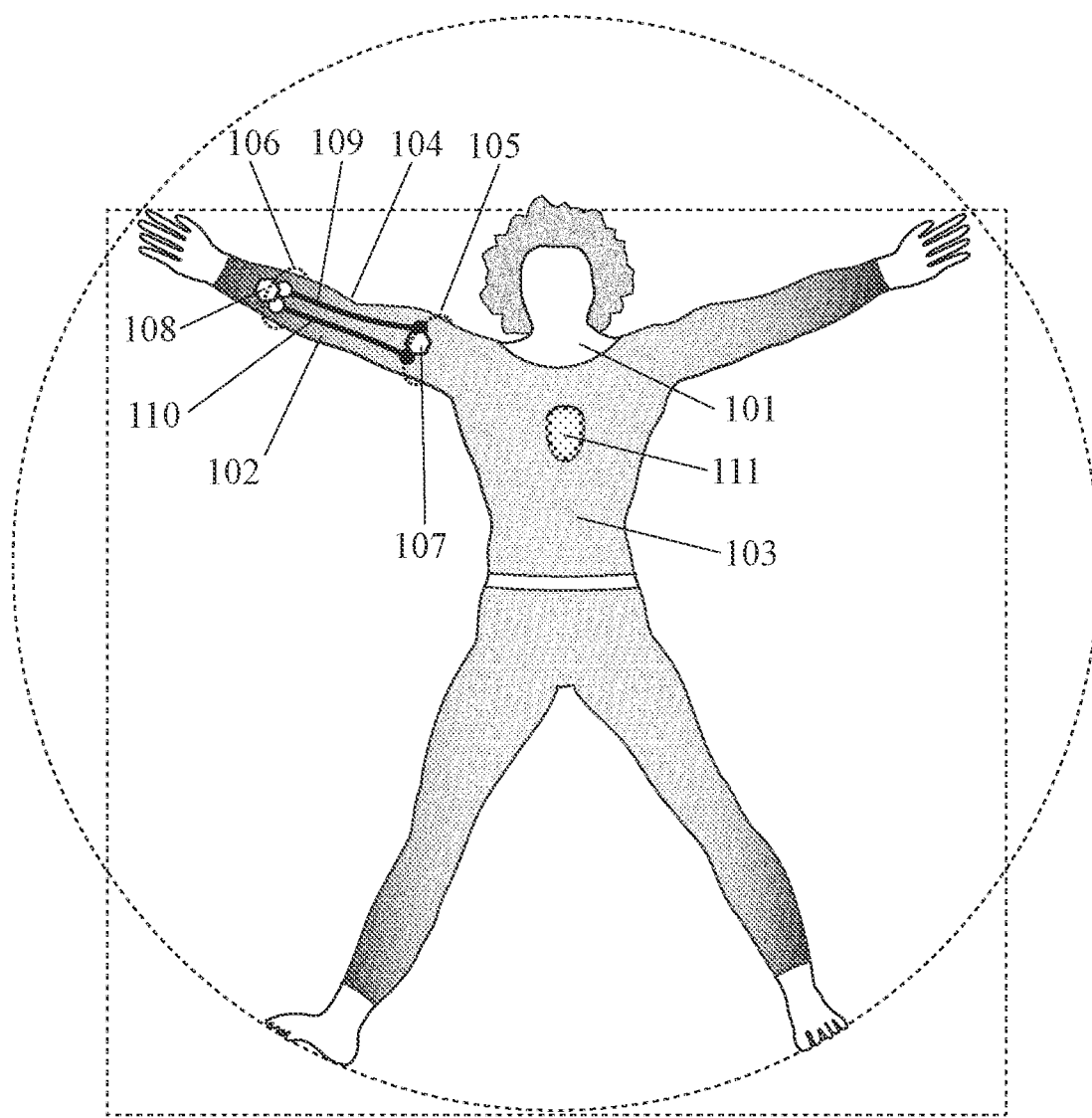
FIG. 1 shows an example of a smart shirt with dual inertial sensors and dual stretch (or bend) sensors.

There are several advantages of Motion Recognition Clothing™ as compared to camera-based or exoskeleton-based methods of motion capture. For example, Motion Recognition Clothing™ is not constrained to a particular location, is not limited by optical occlusion, does not constrain or hinder body motion, can be unobtrusively integrated into clothing, and can be more accurate in measuring body joint motion than devices in the prior art. Full-body Motion Recognition Clothing™ can enable minimally-intrusive, ambulatory, full-body motion capture that does not confine a person to a narrow location in front of a camera. Such Motion Recognition Clothing™ opens up opportunities for full-body motion capture of outdoor and large-scale activities such as playing golf, running, swimming, playing soccer and playing basketball. Motion Recognition Clothing™ also has several applications for medical diagnosis and therapy, including range of motion analysis for body joints.

More generally, Motion Recognition Clothing™ enables mobile non-intrusive measurement of body motion, posture, and/or configuration for many applications. Such clothing has many potential applications including: athletic training and motion capture for sports which involve extensive lower-body motion (such as bicycling and soccer), extensive arm motion (such as tennis and golf), extensive lower-body motion (such as bicycling and running), extensive spinal motion, extensive forearm motion (such as tennis and golf), wrist motion (such as tennis, golf, and Frisbee), ankle motion (such as running and soccer), finger and hand motion (such as tennis, golf, baseball, and fencing), athletic performance measurement and improvement; and entertainment, gaming, and artistic applications (such as animated pictures, avatar animation, computer animation, computer gaming, dance instruction, dance performance, gaming input devices, graphical animation, motion capture, motion picture animation, motion pictures, movie making, performance arts, training and motion capture for playing musical instruments, virtual gaming, virtual reality); and health, fitness, and medical applications (such as avoidance of repeated motion injuries, biofeedback, biomechanical analysis, caloric expenditure measurement, caloric intake monitoring, cardiac function monitoring, congestive heart failure assessment, energy balance, ergonomic evaluation, fall prevention and detection, gait analysis, medical diagnosis, medical therapy, nutritional monitoring and improvement, orthopedic therapy, orthotic design and fitting, physical therapy, plethysmography, post-operative therapy, posture correction, pronation analysis, pulse monitoring, range of motion assessment, rehabilitation assessment, repetitive stress injury avoidance, respiratory function analysis, spinal injury avoidance, spinal motion assessment, telemedicine, telesurgery, virtual exercise, weight management); and human-computer interface and telecommunication (such as gesture recognition, telerobotics, telesurgery, telepresence, notifications, telecommunication, teleconferencing, telepresence, telerobotics, virtual commerce, and virtual reality interaction).

Before discussing the specific examples of Motion Recognition Clothing™ which are shown in FIGS. 1 through 7, it is useful to first discuss some general embodiment variations which can be applied later to these specific examples. Motion Recognition Clothing™ can comprise a wearable electroconductive mesh, grid, lattice, or matrix which is formed by a plurality of electroconductive pathways which span one or more body joints. As these body joints move, they bend, stretch, elongate, and/or twist the mesh, grid, lattice, or matrix. This bending, stretching, elongation, and/or twisting changes the flows of energy through different energy pathways in the mesh, grid, lattice, or matrix. These changes in energy flows can, in turn, be measured by energy sensors and analyzed together to estimate the motions and/or configurations of the body joints.

In an example, a wearable device to measure the motion and/or configuration of a person's body can comprise: a wearable energy-conducting mesh, lattice, grid, or matrix that spans the surface of a portion of a person's body which contains a joint, wherein the mesh, lattice, grid, or matrix further comprises a plurality of energy pathways; a plurality of energy input components which direct energy into the energy pathways at a first plurality (or set) of locations; a plurality of energy sensors which measure energy flow through the energy pathways from a second plurality (or set) of locations; and wherein data from the energy sensors are analyzed in order to measure the motion and/or configuration of the body joint.

In an example, an energy-conducting mesh, lattice, grid, or matrix can be incorporated into or attached to an article of clothing. In an example, the type of energy which is measured can be electrical energy. In an example, energy flow can be measured by measuring voltage, resistance, or impedance. In an example, the mesh, lattice, grid, or matrix can comprise an orthogonal array of energy pathways. In an example, the mesh, lattice, grid, or matrix can comprise a nested array of energy pathways. In an example, the mesh, lattice, grid, or matrix can comprise a woven array of energy pathways. In an example, the mesh, lattice, grid, or matrix can comprise a knitted array of energy pathways.

In an example, a mesh, lattice, grid, or matrix can have interlocking and/or repeating elements which are all the same size and shape. In an example, gaps or elements in a mesh, lattice, grid, or matrix can have square, rhomboid, diamond, trapezoidal, or parallelogram shapes. In an example, gaps or elements in a mesh, lattice, grid, or matrix can have hexagonal shapes. In an example, gaps or elements in a mesh, lattice, grid, or matrix can have triangular shapes. In an example, gaps or elements in a mesh, lattice, grid, or matrix can have circular or elliptical shapes. In an example, gaps or elements in a mesh, lattice, grid, or matrix can have conic section shapes. In an example, gaps or elements in a mesh, lattice, grid, or matrix can have helical or spiral shapes.

In an example, gaps or elements in a mesh, lattice, grid, or matrix can have sinusoidal shapes. In an example, gaps or elements in a mesh, lattice, grid, or matrix can have shapes formed by parallel sinusoidal pathways. In an example, gaps or elements in a mesh, lattice, grid, or matrix can have shapes formed by intersecting sinusoidal pathways. In an example, a mesh, grid, lattice, or matrix further can comprise loops. In an example, a mesh, grid, lattice, or matrix further can comprise interlocking chains of loops.

In an example, an article of clothing or clothing accessory for estimating and/or modeling three-dimensional body motion, posture, and/or configuration can have a mesh, grid, lattice, or matrix of multiple flexible electromagnetic energy pathways, each of which longitudinally spans the same body joint in a selected configuration in order to increase measurement accuracy. Data from multiple flexible energy pathways which span the same body joint can be analyzed with multivariate statistical methods in order to estimate and/or model three-dimensional body motion, posture, and/or configuration.

In an example, a device or system for capturing human motion can comprise: an article of clothing worn by a person, wherein a portion of the article of clothing has a longitudinal axis which is configured to span a body joint, wherein the portion has a first cross-sectional circumference which is proximal relative to the body joint, wherein the portion has a second cross-sectional circumference which is distal relative to the body joint, and wherein proximal means closer to and distal means farther from the person's heart when the person is in Vitruvian Man configuration; a first inertial motion sensor which is incorporated into the portion at the first cross-sectional circumference; a second inertial motion sensor which is incorporated into the portion at the second cross-sectional circumference; a first stretch sensor made with an elastomeric silicone-based polymer which has been doped, impregnated, or coated with electroconductive material and is incorporated into the portion and spans the body joint between the first cross-sectional circumference and the second cross-sectional circumference, wherein the first stretch sensor collects data concerning the transmission of electromagnetic energy through the first stretch sensor; a second stretch sensor made with an elastomeric silicone-based polymer which has been doped, impregnated, or coated with electroconductive material and is incorporated into the portion and spans the body joint between the first cross-sectional circumference and the second cross-sectional circumference, wherein the second stretch sensor collects data concerning the transmission of electromagnetic energy through the second stretch sensor; a stretch (or bend) sensor which is incorporated into the portion and is in electromagnetic communication with a muscle which moves the body joint and/or with nerves which innervate the muscle, and wherein the stretch (or bend) sensor collects data concerning electromagnetic energy emitted by the muscle and/or the nerves; and a data processor which analyzes data from the first inertial motion sensor, the second inertial motion sensor, the first stretch sensor, the second stretch sensor, and the stretch (or bend) sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first optical stretch (or bend) sensor made from PMMA or a styrene-based polymer which is incorporated into (or attached to) the portion and spans the body joint between the first cross-sectional circumference and the second cross-sectional circumference, and wherein the first optical stretch sensor collects data concerning the transmission of light energy through the first optical stretch sensor; (e) a second optical stretch (or bend) sensor made from PMMA or a styrene-based polymer which is incorporated into (or attached to) the portion and spans the body joint between the first cross-sectional circumference and the second cross-sectional circumference, and wherein the second optical stretch sensor collects data concerning the transmission of light energy through the second optical stretch sensor; (f) a stretch (or bend) sensor which is incorporated into (or attached to) the portion and is in electromagnetic communication with a muscle which moves the body joint and/or with nerves which innervate the muscle, and wherein the stretch (or bend) sensor collects data concerning electromagnetic energy emitted by the muscle and/or the nerves; and (g) a data processor which analyzes data from the first inertial motion sensor, the second inertial motion sensor, the first stretch sensor, the second stretch sensor, and the stretch (or bend) sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first stretch (or bend) sensor comprising a light energy transmission sensor made from an elastomeric polymer doped with dye which is incorporated into (or attached to) the portion and spans the body joint between the first cross-sectional circumference and the second cross-sectional circumference, and wherein the first stretch sensor collects data concerning the transmission of light energy through the first stretch sensor; (e) a second stretch (or bend) sensor comprising a light energy transmission sensor made from an elastomeric polymer doped with dye which is incorporated into (or attached to) the portion and spans the body joint between the first cross-sectional circumference and the second cross-sectional circumference, and wherein the second stretch sensor collects data concerning the transmission of light energy through the second stretch sensor; (f) a stretch (or bend) sensor which is incorporated into (or attached to) the portion and is in electromagnetic communication with a muscle which moves the body joint and/or with nerves which innervate the muscle, and wherein the stretch (or bend) sensor collects data concerning electromagnetic energy emitted by the muscle and/or the nerves; and (g) a data processor which analyzes data from the first inertial motion sensor, the second inertial motion sensor, the first stretch sensor, the second stretch sensor, and the stretch (or bend) sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first stretch (or bend) sensor made by printing conductive silicone-based ink onto portion which spans the body joint between the first cross-sectional circumference and the second cross-sectional circumference, and wherein the first stretch sensor collects data concerning the transmission of energy through the first stretch sensor; (e) a second stretch (or bend) sensor made by printing conductive silicone-based ink onto portion which spans the body joint between the first cross-sectional circumference and the second cross-sectional circumference, and wherein the second stretch sensor collects data concerning the transmission of energy through the second stretch sensor; (f) a stretch (or bend) sensor which is incorporated into (or attached to) the portion and is in electromagnetic communication with a muscle which moves the body joint and/or with nerves which innervate the muscle, and wherein the stretch (or bend) sensor collects data concerning electromagnetic energy emitted by the muscle and/or the nerves; and (g) a data processor which analyzes data from the first inertial motion sensor, the second inertial motion sensor, the first stretch sensor, the second stretch sensor, and the stretch (or bend) sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first stretch (or bend) sensor made from a silicone polymer which has been embedded, impregnated, doped, or coated with conductive material which is incorporated into (or attached to) the portion and spans the body joint between the first cross-sectional circumference and the second cross-sectional circumference, and wherein the first stretch sensor collects data concerning the transmission of electromagnetic energy through the first stretch sensor; (e) a second stretch (or bend) sensor made from a silicone polymer which has been embedded, impregnated, doped, or coated with conductive material which is incorporated into (or attached to) the portion and spans the body joint between the first cross-sectional circumference and the second cross-sectional circumference, and wherein the second stretch sensor collects data concerning the transmission of electromagnetic energy through the second stretch sensor; (f) a stretch (or bend) sensor which is incorporated into (or attached to) the portion and is in electromagnetic communication with a muscle which moves the body joint and/or with nerves which innervate the muscle, and wherein the stretch (or bend) sensor collects data concerning electromagnetic energy emitted by the muscle and/or the nerves; and (g) a data processor which analyzes data from the first inertial motion sensor, the second inertial motion sensor, the first stretch sensor, the second stretch sensor, and the stretch (or bend) sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first stretch (or bend) sensor made from a silicone polymer which has been embedded, impregnated, doped, or coated with silver particles which is incorporated into (or attached to) the portion and spans the body joint between the first cross-sectional circumference and the second cross-sectional circumference, and wherein the first stretch sensor collects data concerning the transmission of electromagnetic energy through the first stretch sensor; (e) a second stretch (or bend) sensor made from a silicone polymer which has been embedded, impregnated, doped, or coated with silver particles which is incorporated into (or attached to) the portion and spans the body joint between the first cross-sectional circumference and the second cross-sectional circumference, and wherein the second stretch sensor collects data concerning the transmission of electromagnetic energy through the second stretch sensor; (f) a stretch (or bend) sensor which is incorporated into (or attached to) the portion and is in electromagnetic communication with a muscle which moves the body joint and/or with nerves which innervate the muscle, and wherein the stretch (or bend) sensor collects data concerning electromagnetic energy emitted by the muscle and/or the nerves; and (g) a data processor which analyzes data from the first inertial motion sensor, the second inertial motion sensor, the first stretch sensor, the second stretch sensor, and the stretch (or bend) sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first stretch (or bend) sensor made from a silicone polymer which has been embedded, impregnated, doped, or coated with carbon which is incorporated into (or attached to) the portion and spans the body joint between the first cross-sectional circumference and the second cross-sectional circumference, and wherein the first stretch sensor collects data concerning the transmission of electromagnetic energy through the first stretch sensor; (e) a second stretch (or bend) sensor made from a silicone polymer which has been embedded, impregnated, doped, or coated with carbon which is incorporated into (or attached to) the portion and spans the body joint between the first cross-sectional circumference and the second cross-sectional circumference, and wherein the second stretch sensor collects data concerning the transmission of electromagnetic energy through the second stretch sensor; (f) a stretch (or bend) sensor which is incorporated into (or attached to) the portion and is in electromagnetic communication with a muscle which moves the body joint and/or with nerves which innervate the muscle, and wherein the stretch (or bend) sensor collects data concerning electromagnetic energy emitted by the muscle and/or the nerves; and (g) a data processor which analyzes data from the first inertial motion sensor, the second inertial motion sensor, the first stretch sensor, the second stretch sensor, and the stretch (or bend) sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first stretch (or bend) sensor made from an elastomeric polymer impregnated, doped, or coated with carbon black which is incorporated into (or attached to) the portion and spans the body joint between the first cross-sectional circumference and the second cross-sectional circumference, and wherein the first stretch sensor collects data concerning the transmission of energy through the first stretch sensor; (e) a second stretch (or bend) sensor made from an elastomeric polymer impregnated, doped, or coated with carbon black which is incorporated into (or attached to) the portion and spans the body joint between the first cross-sectional circumference and the second cross-sectional circumference, and wherein the second stretch sensor collects data concerning the transmission of energy through the second stretch sensor; (f) a stretch (or bend) sensor which is incorporated into (or attached to) the portion and is in electromagnetic communication with a muscle which moves the body joint and/or with nerves which innervate the muscle, and wherein the stretch (or bend) sensor collects data concerning electromagnetic energy emitted by the muscle and/or the nerves; and (g) a data processor which analyzes data from the first inertial motion sensor, the second inertial motion sensor, the first stretch sensor, the second stretch sensor, and the stretch (or bend) sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first stretch (or bend) sensor made from an elastomeric polymer impregnated, doped, or coated with graphene which is incorporated into (or attached to) the portion and spans the body joint between the first cross-sectional circumference and the second cross-sectional circumference, and wherein the first stretch sensor collects data concerning the transmission of energy through the first stretch sensor; (e) a second stretch (or bend) sensor made from an elastomeric polymer impregnated, doped, or coated with graphene which is incorporated into (or attached to) the portion and spans the body joint between the first cross-sectional circumference and the second cross-sectional circumference, and wherein the second stretch sensor collects data concerning the transmission of energy through the second stretch sensor; (f) a stretch (or bend) sensor which is incorporated into (or attached to) the portion and is in electromagnetic communication with a muscle which moves the body joint and/or with nerves which innervate the muscle, and wherein the stretch (or bend) sensor collects data concerning electromagnetic energy emitted by the muscle and/or the nerves; and (g) a data processor which analyzes data from the first inertial motion sensor, the second inertial motion sensor, the first stretch sensor, the second stretch sensor, and the stretch (or bend) sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first stretch (or bend) sensor made from an elastomeric polymer impregnated, doped, or coated with iron particles which is incorporated into (or attached to) the portion and spans the body joint between the first cross-sectional circumference and the second cross-sectional circumference, and wherein the first stretch sensor collects data concerning the transmission of energy through the first stretch sensor; (e) a second stretch (or bend) sensor made from an elastomeric polymer impregnated, doped, or coated with iron particles which is incorporated into (or attached to) the portion and spans the body joint between the first cross-sectional circumference and the second cross-sectional circumference, and wherein the second stretch sensor collects data concerning the transmission of energy through the second stretch sensor; (f) a stretch (or bend) sensor which is incorporated into (or attached to) the portion and is in electromagnetic communication with a muscle which moves the body joint and/or with nerves which innervate the muscle, and wherein the stretch (or bend) sensor collects data concerning electromagnetic energy emitted by the muscle and/or the nerves; and (g) a data processor which analyzes data from the first inertial motion sensor, the second inertial motion sensor, the first stretch sensor, the second stretch sensor, and the stretch (or bend) sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first stretch (or bend) sensor made from an elastomeric polymer impregnated, doped, or coated with carbon nanotubes which is incorporated into (or attached to) the portion and spans the body joint between the first cross-sectional circumference and the second cross-sectional circumference, and wherein the first stretch sensor collects data concerning the transmission of energy through the first stretch sensor; (e) a second stretch (or bend) sensor made from an elastomeric polymer impregnated, doped, or coated with carbon nanotubes which is incorporated into (or attached to) the portion and spans the body joint between the first cross-sectional circumference and the second cross-sectional circumference, and wherein the second stretch sensor collects data concerning the transmission of energy through the second stretch sensor; (f) a stretch (or bend) sensor which is incorporated into (or attached to) the portion and is in electromagnetic communication with a muscle which moves the body joint and/or with nerves which innervate the muscle, and wherein the stretch (or bend) sensor collects data concerning electromagnetic energy emitted by the muscle and/or the nerves; and (g) a data processor which analyzes data from the first inertial motion sensor, the second inertial motion sensor, the first stretch sensor, the second stretch sensor, and the stretch (or bend) sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first stretch (or bend) sensor made from an elastomeric polymer which has been impregnated, doped, or coated with carbon, copper, silver, nickel, aluminum, steel, or iron and which is incorporated into (or attached to) the portion and spans the body joint between the first cross-sectional circumference and the second cross-sectional circumference, and wherein the first stretch sensor collects data concerning the transmission of energy through the first stretch sensor; (e) a second stretch (or bend) sensor made from an elastomeric polymer which has been impregnated, doped, or coated with carbon, copper, silver, nickel, aluminum, steel, or iron and which is incorporated into (or attached to) the portion and spans the body joint between the first cross-sectional circumference and the second cross-sectional circumference, and wherein the second stretch sensor collects data concerning the transmission of energy through the second stretch sensor; (f) a stretch (or bend) sensor which is incorporated into (or attached to) the portion and is in electromagnetic communication with a muscle which moves the body joint and/or with nerves which innervate the muscle, and wherein the stretch (or bend) sensor collects data concerning electromagnetic energy emitted by the muscle and/or the nerves; and (g) a data processor which analyzes data from the first inertial motion sensor, the second inertial motion sensor, the first stretch sensor, the second stretch sensor, and the stretch (or bend) sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first stretch (or bend) sensor made from an elastomeric polymer which has been embedded, impregnated, doped, or coated with conductive material which is incorporated into (or attached to) the portion and spans the body joint between the first cross-sectional circumference and the second cross-sectional circumference, and wherein the first stretch sensor collects data concerning the transmission of electromagnetic energy through the first stretch sensor; (e) a second stretch (or bend) sensor made from an elastomeric polymer which has been embedded, impregnated, doped, or coated with conductive material which is incorporated into (or attached to) the portion and spans the body joint between the first cross-sectional circumference and the second cross-sectional circumference, and wherein the second stretch sensor collects data concerning the transmission of electromagnetic energy through the second stretch sensor; (f) a stretch (or bend) sensor which is incorporated into (or attached to) the portion and is in electromagnetic communication with a muscle which moves the body joint and/or with nerves which innervate the muscle, and wherein the stretch (or bend) sensor collects data concerning electromagnetic energy emitted by the muscle and/or the nerves; and (g) a data processor which analyzes data from the first inertial motion sensor, the second inertial motion sensor, the first stretch sensor, the second stretch sensor, and the stretch (or bend) sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first stretch (or bend) sensor made from an polyurethane which has been embedded, impregnated, doped, or coated with silver particles is incorporated into (or attached to) the portion and spans the body joint between the first cross-sectional circumference and the second cross-sectional circumference, and wherein the first stretch sensor collects data concerning the transmission of electromagnetic energy through the first stretch sensor; (e) a second stretch (or bend) sensor made from an polyurethane which has been embedded, impregnated, doped, or coated with silver particles is incorporated into (or attached to) the portion and spans the body joint between the first cross-sectional circumference and the second cross-sectional circumference, and wherein the second stretch sensor collects data concerning the transmission of electromagnetic energy through the second stretch sensor; (f) a stretch (or bend) sensor which is incorporated into (or attached to) the portion and is in electromagnetic communication with a muscle which moves the body joint and/or with nerves which innervate the muscle, and wherein the stretch (or bend) sensor collects data concerning electromagnetic energy emitted by the muscle and/or the nerves; and (g) a data processor which analyzes data from the first inertial motion sensor, the second inertial motion sensor, the first stretch sensor, the second stretch sensor, and the stretch (or bend) sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first stretch (or bend) sensor made from nylon, rubber, or spandex which has been impregnated, doped, or coated with carbon, copper, silver, nickel, aluminum, steel, or iron and which is incorporated into (or attached to) the portion and spans the body joint between the first cross-sectional circumference and the second cross-sectional circumference, and wherein the first stretch sensor collects data concerning the transmission of energy through the first stretch sensor; (e) a second stretch (or bend) sensor made from nylon, rubber, or spandex which has been impregnated, doped, or coated with carbon, copper, silver, nickel, aluminum, steel, or iron and which is incorporated into (or attached to) the portion and spans the body joint between the first cross-sectional circumference and the second cross-sectional circumference, and wherein the second stretch sensor collects data concerning the transmission of energy through the second stretch sensor; (f) a stretch (or bend) sensor which is incorporated into (or attached to) the portion and is in electromagnetic communication with a muscle which moves the body joint and/or with nerves which innervate the muscle, and wherein the stretch (or bend) sensor collects data concerning electromagnetic energy emitted by the muscle and/or the nerves; and (g) a data processor which analyzes data from the first inertial motion sensor, the second inertial motion sensor, the first stretch sensor, the second stretch sensor, and the stretch (or bend) sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first stretch (or bend) sensor made from polydimethylsiloxane (PDMS) which has been embedded, impregnated, doped, or coated with conductive material which is incorporated into (or attached to) the portion and spans the body joint between the first cross-sectional circumference and the second cross-sectional circumference, and wherein the first stretch sensor collects data concerning the transmission of electromagnetic energy through the first stretch sensor; (e) a second stretch (or bend) sensor made from polydimethylsiloxane (PDMS) which has been embedded, impregnated, doped, or coated with conductive material which is incorporated into (or attached to) the portion and spans the body joint between the first cross-sectional circumference and the second cross-sectional circumference, and wherein the second stretch sensor collects data concerning the transmission of electromagnetic energy through the second stretch sensor; (f) a stretch (or bend) sensor which is incorporated into (or attached to) the portion and is in electromagnetic communication with a muscle which moves the body joint and/or with nerves which innervate the muscle, and wherein the stretch (or bend) sensor collects data concerning electromagnetic energy emitted by the muscle and/or the nerves; and (g) a data processor which analyzes data from the first inertial motion sensor, the second inertial motion sensor, the first stretch sensor, the second stretch sensor, and the stretch (or bend) sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first stretch (or bend) sensor made from polydimethylsiloxane (PDMS) which has been embedded, impregnated, doped, or coated with silver particles which is incorporated into (or attached to) the portion and spans the body joint between the first cross-sectional circumference and the second cross-sectional circumference, and wherein the first stretch sensor collects data concerning the transmission of electromagnetic energy through the first stretch sensor; (e) a second stretch (or bend) sensor made from polydimethylsiloxane (PDMS) which has been embedded, impregnated, doped, or coated with silver particles which is incorporated into (or attached to) the portion and spans the body joint between the first cross-sectional circumference and the second cross-sectional circumference, and wherein the second stretch sensor collects data concerning the transmission of electromagnetic energy through the second stretch sensor; (f) a stretch (or bend) sensor which is incorporated into (or attached to) the portion and is in electromagnetic communication with a muscle which moves the body joint and/or with nerves which innervate the muscle, and wherein the stretch (or bend) sensor collects data concerning electromagnetic energy emitted by the muscle and/or the nerves; and (g) a data processor which analyzes data from the first inertial motion sensor, the second inertial motion sensor, the first stretch sensor, the second stretch sensor, and the stretch (or bend) sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first stretch (or bend) sensor made from polydimethylsiloxane (PDMS) which has been embedded, impregnated, doped, or coated with carbon which is incorporated into (or attached to) the portion and spans the body joint between the first cross-sectional circumference and the second cross-sectional circumference, and wherein the first stretch sensor collects data concerning the transmission of electromagnetic energy through the first stretch sensor; (e) a second stretch (or bend) sensor made from polydimethylsiloxane (PDMS) which has been embedded, impregnated, doped, or coated with carbon which is incorporated into (or attached to) the portion and spans the body joint between the first cross-sectional circumference and the second cross-sectional circumference, and wherein the second stretch sensor collects data concerning the transmission of electromagnetic energy through the second stretch sensor; (f) a stretch (or bend) sensor which is incorporated into (or attached to) the portion and is in electromagnetic communication with a muscle which moves the body joint and/or with nerves which innervate the muscle, and wherein the stretch (or bend) sensor collects data concerning electromagnetic energy emitted by the muscle and/or the nerves; and (g) a data processor which analyzes data from the first inertial motion sensor, the second inertial motion sensor, the first stretch sensor, the second stretch sensor, and the stretch (or bend) sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first stretch (or bend) sensor which is incorporated into (or attached to) the portion and spans the body joint between the first cross-sectional circumference and the second cross-sectional circumference, and wherein the first stretch sensor collects data concerning the transmission of electromagnetic energy through the first stretch sensor; (e) a second stretch (or bend) sensor which is incorporated into (or attached to) the portion and spans the body joint between the first cross-sectional circumference and the second cross-sectional circumference, and wherein the second stretch sensor collects data concerning the transmission of energy through the second stretch sensor; (f) a stretch (or bend) sensor made with electrically-conductive silver yarn which is incorporated into (or attached to) the portion and is in electromagnetic communication with a muscle which moves the body joint and/or with nerves which innervate the muscle, and wherein the stretch (or bend) sensor collects data concerning electromagnetic energy emitted by the muscle and/or the nerves; and (g) a data processor which analyzes data from the first inertial motion sensor, the second inertial motion sensor, the first stretch sensor, the second stretch sensor, and the stretch (or bend) sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first stretch (or bend) sensor which is incorporated into (or attached to) the portion and spans the body joint between the first cross-sectional circumference and the second cross-sectional circumference, and wherein the first stretch sensor collects data concerning the transmission of electromagnetic energy through the first stretch sensor; (e) a second stretch (or bend) sensor which is incorporated into (or attached to) the portion and spans the body joint between the first cross-sectional circumference and the second cross-sectional circumference, and wherein the second stretch sensor collects data concerning the transmission of electromagnetic energy through the second stretch sensor; (f) a stretch (or bend) sensor made with an elastomeric polymer which has been embedded, impregnated, doped, or coated with conductive material which is incorporated into (or attached to) the portion and is in electromagnetic communication with a muscle which moves the body joint and/or with nerves which innervate the muscle, and wherein the stretch (or bend) sensor collects data concerning electromagnetic energy emitted by the muscle and/or the nerves; and (g) a data processor which analyzes data from the first inertial motion sensor, the second inertial motion sensor, the first stretch sensor, the second stretch sensor, and the stretch (or bend) sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first stretch (or bend) sensor which is incorporated into (or attached to) the portion and spans the body joint between the first cross-sectional circumference and the second cross-sectional circumference, and wherein the first stretch sensor collects data concerning the transmission of electromagnetic energy through the first stretch sensor; (e) a second stretch (or bend) sensor which is incorporated into (or attached to) the portion and spans the body joint between the first cross-sectional circumference and the second cross-sectional circumference, and wherein the second stretch sensor collects data concerning the transmission of electromagnetic energy through the second stretch sensor; (f) a stretch (or bend) sensor made with polydimethylsiloxane (PDMS) which has been embedded, impregnated, doped, or coated with conductive material which is incorporated into (or attached to) the portion and is in electromagnetic communication with a muscle which moves the body joint and/or with nerves which innervate the muscle, and wherein the stretch (or bend) sensor collects data concerning electromagnetic energy emitted by the muscle and/or the nerves; and (g) a data processor which analyzes data from the first inertial motion sensor, the second inertial motion sensor, the first stretch sensor, the second stretch sensor, and the stretch (or bend) sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first stretch (or bend) sensor which is incorporated into (or attached to) the portion and spans the body joint between the first cross-sectional circumference and the second cross-sectional circumference, and wherein the first stretch sensor collects data concerning the transmission of electromagnetic energy through the first stretch sensor; (e) a second stretch (or bend) sensor which is incorporated into (or attached to) the portion and spans the body joint between the first cross-sectional circumference and the second cross-sectional circumference, and wherein the second stretch sensor collects data concerning the transmission of electromagnetic energy through the second stretch sensor; (f) a stretch (or bend) sensor made with polydimethylsiloxane (PDMS) which has been embedded, impregnated, doped, or coated with silver particles which is incorporated into (or attached to) the portion and is in electromagnetic communication with a muscle which moves the body joint and/or with nerves which innervate the muscle, and wherein the stretch (or bend) sensor collects data concerning electromagnetic energy emitted by the muscle and/or the nerves; and (g) a data processor which analyzes data from the first inertial motion sensor, the second inertial motion sensor, the first stretch sensor, the second stretch sensor, and the stretch (or bend) sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first stretch (or bend) sensor which is incorporated into (or attached to) the portion and spans the body joint between the first cross-sectional circumference and the second cross-sectional circumference, and wherein the first stretch sensor collects data concerning the transmission of electromagnetic energy through the first stretch sensor; (e) a second stretch (or bend) sensor which is incorporated into (or attached to) the portion and spans the body joint between the first cross-sectional circumference and the second cross-sectional circumference, and wherein the second stretch sensor collects data concerning the transmission of electromagnetic energy through the second stretch sensor; (f) a stretch (or bend) sensor made with polydimethylsiloxane (PDMS) which has been embedded, impregnated, doped, or coated with carbon which is incorporated into (or attached to) the portion and is in electromagnetic communication with a muscle which moves the body joint and/or with nerves which innervate the muscle, and wherein the stretch (or bend) sensor collects data concerning electromagnetic energy emitted by the muscle and/or the nerves; and (g) a data processor which analyzes data from the first inertial motion sensor, the second inertial motion sensor, the first stretch sensor, the second stretch sensor, and the stretch (or bend) sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first stretch (or bend) sensor which is incorporated into (or attached to) the portion and spans the body joint between the first cross-sectional circumference and the second cross-sectional circumference, and wherein the first stretch sensor collects data concerning the transmission of electromagnetic energy through the first stretch sensor; (e) a second stretch (or bend) sensor which is incorporated into (or attached to) the portion and spans the body joint between the first cross-sectional circumference and the second cross-sectional circumference, and wherein the second stretch sensor collects data concerning the transmission of electromagnetic energy through the second stretch sensor; (f) a stretch (or bend) sensor made with polyurethane which has been embedded, impregnated, doped, or coated with silver particles which is incorporated into (or attached to) the portion and is in electromagnetic communication with a muscle which moves the body joint and/or with nerves which innervate the muscle, and wherein the stretch (or bend) sensor collects data concerning electromagnetic energy emitted by the muscle and/or the nerves; and (g) a data processor which analyzes data from the first inertial motion sensor, the second inertial motion sensor, the first stretch sensor, the second stretch sensor, and the stretch (or bend) sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first stretch (or bend) sensor which is incorporated into (or attached to) the portion and spans the body joint between the first cross-sectional circumference and the second cross-sectional circumference, and wherein the first stretch sensor collects data concerning the transmission of electromagnetic energy through the first stretch sensor; (e) a second stretch (or bend) sensor which is incorporated into (or attached to) the portion and spans the body joint between the first cross-sectional circumference and the second cross-sectional circumference, and wherein the second stretch sensor collects data concerning the transmission of electromagnetic energy through the second stretch sensor; (f) a stretch (or bend) sensor made with a silicone polymer which has been embedded, impregnated, doped, or coated with conductive material which is incorporated into (or attached to) the portion and is in electromagnetic communication with a muscle which moves the body joint and/or with nerves which innervate the muscle, and wherein the stretch (or bend) sensor collects data concerning electromagnetic energy emitted by the muscle and/or the nerves; and (g) a data processor which analyzes data from the first inertial motion sensor, the second inertial motion sensor, the first stretch sensor, the second stretch sensor, and the stretch (or bend) sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first stretch (or bend) sensor which is incorporated into (or attached to) the portion and spans the body joint between the first cross-sectional circumference and the second cross-sectional circumference, and wherein the first stretch sensor collects data concerning the transmission of electromagnetic energy through the first stretch sensor; (e) a second stretch (or bend) sensor which is incorporated into (or attached to) the portion and spans the body joint between the first cross-sectional circumference and the second cross-sectional circumference, and wherein the second stretch sensor collects data concerning the transmission of electromagnetic energy through the second stretch sensor; (f) a stretch (or bend) sensor made with a silicone polymer which has been embedded, impregnated, doped, or coated with silver particles which is incorporated into (or attached to) the portion and is in electromagnetic communication with a muscle which moves the body joint and/or with nerves which innervate the muscle, and wherein the stretch (or bend) sensor collects data concerning electromagnetic energy emitted by the muscle and/or the nerves; and (g) a data processor which analyzes data from the first inertial motion sensor, the second inertial motion sensor, the first stretch sensor, the second stretch sensor, and the stretch (or bend) sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first stretch (or bend) sensor which is incorporated into (or attached to) the portion and spans the body joint between the first cross-sectional circumference and the second cross-sectional circumference, and wherein the first stretch sensor collects data concerning the transmission of electromagnetic energy through the first stretch sensor; (e) a second stretch (or bend) sensor which is incorporated into (or attached to) the portion and spans the body joint between the first cross-sectional circumference and the second cross-sectional circumference, and wherein the second stretch sensor collects data concerning the transmission of electromagnetic energy through the second stretch sensor; (f) a stretch (or bend) sensor made with a silicone polymer which has been embedded, impregnated, doped, or coated with carbon which is incorporated into (or attached to) the portion and is in electromagnetic communication with a muscle which moves the body joint and/or with nerves which innervate the muscle, and wherein the stretch (or bend) sensor collects data concerning electromagnetic energy emitted by the muscle and/or the nerves; and (g) a data processor which analyzes data from the first inertial motion sensor, the second inertial motion sensor, the first stretch sensor, the second stretch sensor, and the stretch (or bend) sensor to measure a configuration and/or motion of the body joint.

In an example, electromagnetic energy sensors can comprise conductive threads, yarns, or fibers which are sewn, woven, or embroidered into smart clothing. In an example, conductive threads, yarns, or fibers can be made from relatively non-conductive material (such as cotton or wool) which is coated or impregnated with conductive material (such as carbon, silver, or aluminum). In an example, electromagnetic energy sensors can comprise longitudinal strips, fibers, channels, or tubes of conductive elastomeric material. In an example, conductive elastomeric material can be made from relatively non-conductive elastomeric material (such as polydimethylsiloxane or PDMS) which is impregnated, doped, or coated with conductive material (such as carbon, silver, or aluminum). In an example, electromagnetic energy sensors can be created by printing patterns onto clothing fabric using conductive ink or resin.

In an example, smart clothing can comprise: an article of clothing which is configured to be worn over a person's arm and/or leg; and an electromagnetic stretch (or bend) sensor comprising a non-conductive polymer (such as PDMS) which has been impregnated, doped, embedded, or coated with metal particles or nanostructures (such as carbon particles or nanostructures); wherein the stretch sensor longitudinally spans an elbow, knee, shoulder, or hip. In an example, smart clothing can comprise: an article of clothing which is configured to be worn over a person's arm and/or leg; and an electromagnetic stretch (or bend) sensor comprising a non-conductive polymer (such as PDMS) which has been impregnated, doped, embedded, or coated with metal particles or nanostructures (such as carbon particles or nanostructures); wherein the stretch sensor spirals around an elbow, knee, shoulder, or hip. In an example, smart clothing can comprise: an article of clothing which is configured to be worn over a person's arm and/or leg; and a stretch (or bend) sensor made with a non-conductive polymer (such as PDMS) which has been impregnated, doped, embedded, or coated with metal particles or nanostructures (such as carbon particles or nanostructures); wherein the stretch (or bend) sensor spans between 5% and 55% of the circumference of the arm or leg.

In an example, smart clothing can comprise: an article of clothing which is configured to be worn over a person's arm and/or leg; and an electromagnetic stretch (or bend) sensor comprising latex impregnated (or doped, embedded, or coated) with niobium; wherein the stretch sensor spirals around an elbow and/or a knee. Alternatively, smart clothing can comprise: an article of clothing worn over a person's arm and/or leg; and an electromagnetic stretch (or bend) sensor comprising silk thread coated (or embedded) with silver (or sliver alloy, silver chloride) particles or pieces; wherein the stretch sensor spirals around an elbow and/or a knee. In an example, it can form a half-spiral around an elbow and/or a knee. Smart clothing can comprise: an article of clothing worn over a person's arm and/or leg; and an electromagnetic stretch (or bend) sensor comprising cellulose, hydroxypropyl cellulose, and/or hydroxypropyl methylcellulose (HPMC) impregnated (or doped, embedded, or coated) with steel particles or pieces; wherein the stretch sensor longitudinally spans the dorsal surface of an elbow and/or the ventral surface of a knee.

In an example, smart clothing can comprise: an article of clothing worn over a person's arm and/or leg; and a stretch (or bend) sensor printed onto the article of clothing with a polydimethylsiloxane PDMS-based ink which has been impregnated (or doped) with conductive metal particles, pieces, or microstructures; wherein the stretch (or bend) sensor spans between 10% and 60% of the circumference of the arm or leg. Smart clothing can comprise: an article of clothing; and a stretch (or bend) sensor comprising stretchable thread or yarn coated (or embedded) with copper (or copper alloy); wherein the stretch (or bend) sensor is woven, sewn, or embroidered into the article of clothing Smart clothing can comprise: an article of clothing; and a stretch (or bend) sensor comprising rubber impregnated (or doped, embedded, or coated) with gallium; wherein the stretch (or bend) sensor is sewn onto, woven into, adhered to, inserted into, or otherwise attached to the article of clothing. Smart clothing can comprise: an article of clothing; and a stretch (or bend) sensor comprising nylon (thread or yarn) coated (or embedded) with gold (or gold alloy) particles or pieces. Alternatively, smart clothing can comprise: an article of clothing; and a stretch (or bend) sensor comprising stretchable thread or yarn coated (or embedded) with nickel (or nickel alloy) particles or pieces. Smart clothing can comprise: an article of clothing worn over a person's arm and/or leg; and an electromagnetic stretch (or bend) sensor comprising acrylic (yarn, thread, or fiber) coated (or embedded) with niobium; wherein the stretch sensor spirals around an elbow and/or a knee.

In an example, smart clothing can comprise: an article of clothing worn over a person's arm and/or leg; and an electromagnetic stretch (or bend) sensor comprising cotton (thread or fiber) coated (or embedded) with silver (or sliver alloy, silver chloride); wherein the stretch sensor spirals around an elbow and/or a knee. Alternatively, smart clothing can comprise: an article of clothing worn over a person's arm and/or leg; and an electromagnetic stretch (or bend) sensor comprising hydrogel impregnated (or doped, embedded, or coated) with niobium; wherein the stretch sensor spirals around an elbow and/or a knee. Smart clothing can comprise: an article of clothing worn over a person's arm and/or leg; and an electromagnetic stretch (or bend) sensor comprising nylon (thread or yarn) coated (or embedded) with tungsten particles or pieces; wherein the stretch sensor spirals around an elbow and/or a knee.

Smart clothing can comprise: an article of clothing which is configured to be worn over a person's arm and/or leg; and an electromagnetic stretch (or bend) sensor comprising polyester (thread or yarn) coated (or embedded) with niobium; wherein the stretch sensor spirals around an elbow and/or a knee. In an example, it can form a half-spiral around an elbow and/or a knee. Alternatively, smart clothing can comprise: an article of clothing worn over a person's arm and/or leg; and an electromagnetic stretch (or bend) sensor comprising polystyrene (PST) impregnated (or doped, embedded, or coated) with silver (or sliver alloy, silver chloride); wherein the stretch sensor spirals around an elbow and/or a knee. Smart clothing can comprise: an article of clothing worn over a person's arm and/or leg; and an electromagnetic stretch (or bend) sensor comprising rayon (thread or yarn) coated (or embedded) with copper (or copper alloy) particles or pieces; wherein the stretch sensor spirals around an elbow and/or a knee.

In an example, smart clothing can comprise: an article of clothing worn over a person's arm and/or leg; and an electromagnetic stretch (or bend) sensor comprising silicone, silicone rubber, and/or PDMS impregnated (or doped, embedded, or coated) with silver (or sliver alloy, silver chloride) particles or pieces; wherein the stretch sensor spirals around an elbow and/or a knee. Alternatively, smart clothing can comprise: an article of clothing worn over a person's arm and/or leg; and an electromagnetic stretch (or bend) sensor comprising styrene ethylene butylene streyene (SEBS) impregnated (or doped, embedded, or coated) with aluminum (or aluminum alloy); wherein the stretch sensor spirals around an elbow and/or a knee. Smart clothing can comprise: an article of clothing worn over a person's arm and/or leg; and an electromagnetic stretch (or bend) sensor comprising thermoplastic elastomer (TPE), thermoplastic polyurethane (TPU), and/or thermoplastic vulcanizate (TPV) impregnated (or doped, embedded, or coated) with silver (or sliver alloy, silver chloride); wherein the stretch sensor spirals around an elbow and/or a knee. In an example, it can form a half-spiral around an elbow and/or a knee. Smart clothing can comprise: an article of clothing which is configured to be worn over a person's arm and/or leg; and an electromagnetic stretch (or bend) sensor printed onto the article of clothing with a polymer-based ink which has been impregnated (or doped) with steel particles or pieces; wherein the stretch sensor spirals around an elbow and/or a knee. Alternatively, smart clothing can comprise: an article of clothing worn over a person's arm and/or leg; and an electromagnetic stretch (or bend) sensor comprising acetate (thread or yarn) coated (or embedded) with gallium; wherein the stretch sensor longitudinally spans the dorsal surface of an elbow and/or the ventral surface of a knee. Alternatively, smart clothing can comprise: an article of clothing worn over a person's arm and/or leg; and an electromagnetic stretch (or bend) sensor comprising an elastic material and/or an elastomeric polymer impregnated (or doped, embedded, or coated) with steel particles or pieces; wherein the stretch sensor longitudinally spans the dorsal surface of an elbow and/or the ventral surface of a knee.

In another example, smart clothing can comprise: an article of clothing worn over a person's arm and/or leg; and an electromagnetic stretch (or bend) sensor comprising rubber impregnated (or doped, embedded, or coated) with conductive metal particles, pieces, or microstructures; wherein the stretch sensor longitudinally spans the dorsal surface of an elbow and/or the ventral surface of a knee. Alternatively, smart clothing can comprise: an article of clothing worn over a person's arm and/or leg; and an electromagnetic stretch (or bend) sensor comprising silicone, silicone rubber, and/or PDMS impregnated (or doped, embedded, or coated) with tungsten particles or pieces; wherein the stretch sensor longitudinally spans the dorsal surface of an elbow and/or the ventral surface of a knee. Smart clothing can comprise: an article of clothing worn over a person's arm and/or leg; and an electromagnetic stretch (or bend) sensor comprising TPE, TPU, and/or TPV impregnated (or doped, embedded, or coated) with conductive metal particles, pieces, or microstructures; wherein the stretch sensor longitudinally spans the dorsal surface of an elbow and/or the ventral surface of a knee.

Alternatively, smart clothing can comprise: an article of clothing which is configured to be worn over a person's arm and/or leg; and an electromagnetic stretch (or bend) sensor printed onto the article of clothing with a PDMS-based ink which has been impregnated (or doped) with nickel (or nickel alloy) particles or pieces; wherein the stretch sensor longitudinally spans the dorsal surface of an elbow and/or the ventral surface of a knee. Smart clothing can comprise: an article of clothing worn over a person's arm and/or leg; and an electromagnetic stretch (or bend) sensor printed onto the article of clothing with conductive ink or resin which has been impregnated (or doped) with aluminum (or aluminum alloy) particles or pieces; wherein the stretch sensor longitudinally spans the dorsal surface of an elbow and/or the ventral surface of a knee. Smart clothing can comprise: an article of clothing worn over a person's arm and/or leg; and a stretch (or bend) sensor comprising acrylic (yarn, thread, or fiber) coated (or embedded) with copper (or copper alloy) particles or pieces; wherein the stretch (or bend) sensor spans between 10% and 60% of the circumference of the arm or leg.

In another example, smart clothing can comprise: an article of clothing worn over a person's arm and/or leg; and a stretch (or bend) sensor comprising silicone, silicone rubber, and/or PDMS impregnated (or doped, embedded, or coated) with carbon (particles, nanotubes, microstructures, graphene, graphite); wherein the stretch (or bend) sensor spans between 10% and 60% of the circumference of the arm or leg. Smart clothing can comprise: an article of clothing worn over a person's arm and/or leg; and a stretch (or bend) sensor comprising stretchable thread or yarn coated (or embedded) with silver (or sliver alloy, silver chloride); wherein the stretch (or bend) sensor spans between 10% and 60% of the circumference of the arm or leg. Smart clothing can comprise: an article of clothing worn over a person's arm and/or leg; and a stretch (or bend) sensor comprising wool yarn coated (or embedded) with conductive metal particles, pieces, or microstructures; wherein the stretch (or bend) sensor spans between 10% and 60% of the circumference of the arm or leg.

Alternatively, smart clothing can comprise: an article of clothing which is configured to be worn over a person's arm and/or leg; and a stretch (or bend) sensor printed onto the article of clothing with a polymer-based ink which has been impregnated (or doped) with gold (or gold alloy); wherein the stretch (or bend) sensor spans between 10% and 60% of the circumference of the arm or leg. Smart clothing can comprise: an article of clothing worn over a person's arm and/or leg; and a stretch (or bend) sensor printed onto the article of clothing with conductive ink or resin which has been impregnated (or doped) with conductive metal particles, pieces, or microstructures; wherein the stretch (or bend) sensor spans between 10% and 60% of the circumference of the arm or leg. Alternatively, smart clothing can comprise: an article of clothing; and a stretch (or bend) sensor comprising cotton (thread or fiber) coated (or embedded) with niobium; wherein the stretch (or bend) sensor is woven, sewn, or embroidered into the article of clothing.

In another example, smart clothing can comprise: an article of clothing; and a stretch (or bend) sensor comprising PVOH impregnated (or doped, embedded, or coated) with gallium; wherein the stretch (or bend) sensor is sewn onto, woven into, adhered to, inserted into, or otherwise attached to the article of clothing. Alternatively, smart clothing can comprise: an article of clothing; and a stretch (or bend) sensor comprising silicone, silicone rubber, and/or PDMS impregnated (or doped, embedded, or coated) with niobium; wherein the stretch (or bend) sensor is sewn onto, woven into, adhered to, inserted into, or otherwise attached to the article of clothing. Alternatively, smart clothing can comprise: an article of clothing; and a stretch (or bend) sensor comprising TPE, TPU, and/or thermoplastic vulcanizate (TPV) impregnated (or doped, embedded, or coated) with gallium; wherein the stretch (or bend) sensor is sewn onto, woven into, adhered to, inserted into, or otherwise attached to the article of clothing. Smart clothing can comprise: an article of clothing; and a stretch (or bend) sensor comprising an elastic material and/or an elastomeric polymer impregnated (or doped, embedded, or coated) with gold (or gold alloy) particles or pieces. Smart clothing can comprise: an article of clothing; and a stretch (or bend) sensor comprising elastane and/or Lycra™ (thread or fiber) coated (or embedded) with tungsten particles or pieces. Smart clothing can comprise: an article of clothing; and a stretch (or bend) sensor comprising latex impregnated (or doped, embedded, or coated) with gold (or gold alloy) particles or pieces.

In an example, smart clothing can comprise: an article of clothing; and a stretch (or bend) sensor comprising PEDOT/

PSS impregnated (or doped, embedded, or coated) with silver (or sliver alloy, silver chloride) particles or pieces. Alternatively, smart clothing can comprise: an article of clothing; and a stretch (or bend) sensor comprising polyethylene glycol (PEG), polyethylene terephthalate (PET), or polytetrafluoroethylene (PTFE) impregnated (or doped, embedded, or coated) with gold (or gold alloy) particles or pieces. Alternatively, smart clothing can comprise: an article of clothing; and a stretch (or bend) sensor comprising polyurethane impregnated (or doped, embedded, or coated) with nickel (or nickel alloy) particles or pieces. Smart clothing can comprise: an article of clothing; and a stretch (or bend) sensor comprising rubber impregnated (or doped, embedded, or coated) with carbon (particles, nanotubes, microstructures, graphene, graphite). Alternatively, smart clothing can comprise: an article of clothing; and a stretch (or bend) sensor comprising silk thread coated (or embedded) with nickel (or nickel alloy) particles or pieces. Smart clothing can comprise: an article of clothing; and a stretch (or bend) sensor comprising SEBS impregnated (or doped, embedded, or coated) with steel particles or pieces.

In another example, smart clothing can comprise: an article of clothing; and a stretch (or bend) sensor comprising wool yarn coated (or embedded) with nickel (or nickel alloy) particles or pieces. Alternatively, smart clothing can comprise: an article of clothing; and a stretch (or bend) sensor printed onto the article of clothing with a silicone-based ink which has been impregnated (or doped) with niobium. Smart clothing can comprise: an article of clothing worn over a person's arm and/or leg; and an electromagnetic stretch (or bend) sensor comprising an elastic material and/or an elastomeric polymer impregnated (or doped, embedded, or coated) with carbon (particles, nanotubes, microstructures, graphene, graphite); wherein the stretch sensor spirals around an elbow and/or a knee. Smart clothing can comprise: an article of clothing worn over a person's arm and/or leg; and an electromagnetic stretch (or bend) sensor comprising elastane and/or Lycra™ (thread or fiber) coated (or embedded) with steel particles or pieces; wherein the stretch sensor spirals around an elbow and/or a knee. Smart clothing can comprise: an article of clothing worn over a person's arm and/or leg; and an electromagnetic stretch (or bend) sensor comprising nylon (thread or yarn) coated (or embedded) with carbon (particles, nanotubes, microstructures, graphene, graphite); wherein the stretch sensor spirals around an elbow and/or a knee. In an example, it can form a half-spiral around an elbow and/or a knee. Alternatively, smart clothing can comprise: an article of clothing worn over a person's arm and/or leg; and an electromagnetic stretch (or bend) sensor comprising polyurethane impregnated (or doped, embedded, or coated) with conductive metal particles, pieces, or microstructures; wherein the stretch sensor spirals around an elbow and/or a knee.

In an example, smart clothing can comprise: an article of clothing which is configured to be worn over a person's arm and/or leg; and an electromagnetic stretch (or bend) sensor comprising rubber impregnated (or doped, embedded, or coated) with conductive metal particles, pieces, or microstructures; wherein the stretch sensor spirals around an elbow and/or a knee. Smart clothing can comprise: an article of clothing worn over a person's arm and/or leg; and an electromagnetic stretch (or bend) sensor comprising stretchable thread or yarn coated (or embedded) with conductive metal particles, pieces, or microstructures; wherein the stretch sensor spirals around an elbow and/or a knee. Alternatively, smart clothing can comprise: an article of clothing which is configured to be worn over a person's arm and/or leg; and an electromagnetic stretch (or bend) sensor printed onto the article of clothing with a silicone-based ink which has been impregnated (or doped) with copper (or copper alloy) particles or pieces; wherein the stretch sensor spirals around an elbow and/or a knee. Smart clothing can comprise: an article of clothing worn over a person's arm and/or leg; and an electromagnetic stretch (or bend) sensor comprising acrylic (yarn, thread, or fiber) coated (or embedded) with copper (or copper alloy) particles or pieces; wherein the stretch sensor longitudinally spans the dorsal surface of an elbow and/or the ventral surface of a knee.

In another example, smart clothing can comprise: an article of clothing worn over a person's arm and/or leg; and an electromagnetic stretch (or bend) sensor comprising polystyrene (PST) impregnated (or doped, embedded, or coated) with gallium; wherein the stretch sensor longitudinally spans the dorsal surface of an elbow and/or the ventral surface of a knee. Alternatively, smart clothing can comprise: an article of clothing worn over a person's arm and/or leg; and an electromagnetic stretch (or bend) sensor comprising rayon (thread or yarn) coated (or embedded) with gallium; wherein the stretch sensor longitudinally spans the dorsal surface of an elbow and/or the ventral surface of a knee. Smart clothing can comprise: an article of clothing worn over a person's arm and/or leg; and an electromagnetic stretch (or bend) sensor comprising TPE, TPU, and/or TPV impregnated (or doped, embedded, or coated) with gold (or gold alloy) particles or pieces; wherein the stretch sensor longitudinally spans the dorsal surface of an elbow and/or the ventral surface of a knee. Smart clothing can comprise: an article of clothing which is configured to be worn over a person's arm and/or leg; and an electromagnetic stretch (or bend) sensor printed onto the article of clothing with a polymer-based ink which has been impregnated (or doped) with gold (or gold alloy) particles or pieces; wherein the stretch sensor longitudinally spans the dorsal surface of an elbow and/or the ventral surface of a knee. Smart clothing can comprise: an article of clothing worn over a person's arm and/or leg; and a stretch (or bend) sensor comprising acetate (thread or yarn) coated (or embedded) with gold (or gold alloy); wherein the stretch (or bend) sensor spans between 10% and 60% of the circumference of the arm or leg. Alternatively, smart clothing can comprise: an article of clothing worn over a person's arm and/or leg; and a stretch (or bend) sensor comprising hydrogel impregnated (or doped, embedded, or coated) with nickel (or nickel alloy) particles or pieces; wherein the stretch (or bend) sensor spans between 5% and 55% of the circumference of the arm or leg.

In an example, smart clothing can comprise: an article of clothing worn over a person's arm and/or leg; and a stretch (or bend) sensor comprising PEDOT/PSS impregnated (or doped, embedded, or coated) with nickel (or nickel alloy) particles or pieces; wherein the stretch (or bend) sensor spans between 10% and 60% of the circumference of the arm or leg. Alternatively, smart clothing can comprise: an article of clothing which is configured to be worn over a person's arm and/or leg; and a stretch (or bend) sensor comprising polypropylene glycol impregnated (or doped, embedded, or coated) with nickel (or nickel alloy); wherein the stretch (or bend) sensor spans between 10% and 60% of the circumference of the arm or leg. Smart clothing can comprise: an article of clothing which is configured to be worn over a person's arm and/or leg; and a stretch (or bend) sensor comprising silicone, silicone rubber, and/or PDMS impregnated (or doped, embedded, or coated) with niobium; wherein the stretch (or bend) sensor spans between 10% and 60% of the circumference of the arm or leg. Alternatively, smart clothing can comprise: an article of clothing worn over a person's arm and/or leg; and a stretch (or bend) sensor comprising SEBS impregnated (or doped, embedded, or coated) with niobium; wherein the stretch (or bend) sensor spans between 10% and 60% of the circumference of the arm or leg. Smart clothing can comprise: an article of clothing which is configured to be worn over a person's arm and/or leg; and a stretch (or bend) sensor printed onto the article of clothing with a PDMS-based ink which has been impregnated (or doped) with niobium; wherein the stretch (or bend) sensor spans between 10% and 60% of the circumference of the arm or leg. Alternatively, smart clothing can comprise: an article of clothing; and a stretch (or bend) sensor comprising cotton (thread or fiber) coated (or embedded) with conductive metal particles, pieces, or microstructures; wherein the stretch (or bend) sensor is woven, sewn, or embroidered into the article of clothing In an example, smart clothing can comprise: an article of clothing; and a stretch (or bend) sensor comprising polyester (thread or yarn) coated (or embedded) with silver (or sliver alloy, silver chloride) particles or pieces; wherein the stretch (or bend) sensor is woven, sewn, or embroidered into the article of clothing. Smart clothing can comprise: an article of clothing; and a stretch (or bend) sensor comprising stretchable thread or yarn coated (or embedded) with silver (or sliver alloy, silver chloride) particles or pieces; wherein the stretch (or bend) sensor is woven, sewn, or embroidered into the article of clothing. Alternatively, smart clothing can comprise: an article of clothing; and a stretch (or bend) sensor comprising PEDOT/PSS impregnated (or doped, embedded, or coated) with steel particles or pieces; wherein the stretch (or bend) sensor is sewn onto, woven into, adhered to, inserted into, or otherwise attached to the article of clothing. Smart clothing can comprise: an article of clothing; and a stretch (or bend) sensor comprising polystyrene (PST) impregnated (or doped, embedded, or coated) with steel particles or pieces; wherein the stretch (or bend) sensor is sewn onto, woven into, adhered to, inserted into, or otherwise attached to the article of clothing. Smart clothing can comprise: an article of clothing; and a stretch (or bend) sensor comprising rubber impregnated (or doped, embedded, or coated) with steel particles or pieces; wherein the stretch (or bend) sensor is sewn onto, woven into, adhered to, inserted into, or otherwise attached to the article of clothing. Alternatively, smart clothing can comprise: an article of clothing; and a stretch (or bend) sensor comprising an elastic material and/or an elastomeric polymer impregnated (or doped, embedded, or coated) with tungsten particles or pieces.

In an example, smart clothing can comprise: an article of clothing; and a stretch (or bend) sensor comprising elastane and/or Lycra™ (thread or fiber) coated (or embedded) with aluminum (or aluminum alloy) particles or pieces. Smart clothing can comprise: an article of clothing; and a stretch (or bend) sensor comprising nylon (thread or yarn) coated (or embedded) with tungsten particles or pieces. Alternatively, smart clothing can comprise: an article of clothing; and a stretch (or bend) sensor comprising PVOH impregnated (or doped, embedded, or coated) with aluminum (or aluminum alloy) particles or pieces. Smart clothing can comprise: an article of clothing; and a stretch (or bend) sensor comprising silicone, silicone rubber, and/or PDMS impregnated (or doped, embedded, or coated) with conductive metal particles, pieces, or microstructures. Alternatively, smart clothing can comprise: an article of clothing; and a stretch (or bend) sensor comprising SEBS impregnated (or doped, embedded, or coated) with aluminum (or aluminum alloy) particles or pieces. Smart clothing can comprise: an article of clothing; and a stretch (or bend) sensor printed onto the article of clothing with conductive ink or resin which has been impregnated (or doped) with carbon (particles, nanotubes, microstructures, graphene, graphite).

In another example, smart clothing can comprise: an article of clothing worn over a person's arm and/or leg; and an electromagnetic stretch (or bend) sensor comprising acrylic (yarn, thread, or fiber) coated (or embedded) with tungsten particles or pieces; wherein the stretch sensor spirals around an elbow and/or a knee. In an example, it can form a half-spiral around an elbow and/or a knee. Smart clothing can comprise: an article of clothing worn over a person's arm and/or leg; and an electromagnetic stretch (or bend) sensor comprising cellulose, hydroxypropyl cellulose, and/or HPMC impregnated (or doped, embedded, or coated) with niobium; wherein the stretch sensor spirals around an elbow and/or a knee. Smart clothing can comprise: an article of clothing worn over a person's arm and/or leg; and an electromagnetic stretch (or bend) sensor comprising nylon (thread or yarn) coated (or embedded) with niobium; wherein the stretch sensor spirals around an elbow and/or a knee. Alternatively, smart clothing can comprise: an article of clothing which is configured to be worn over a person's arm and/or leg; and an electromagnetic stretch (or bend) sensor comprising polyethylene glycol (PEG), polyethylene terephthalate (PET), or polytetrafluoroethylene (PTFE) impregnated (or doped, embedded, or coated) with aluminum (or aluminum alloy) particles or pieces; wherein the stretch sensor spirals around an elbow and/or a knee. Smart clothing can comprise: an article of clothing worn over a person's arm and/or leg; and an electromagnetic stretch (or bend) sensor comprising polyurethane impregnated (or doped, embedded, or coated) with aluminum (or aluminum alloy) particles or pieces; wherein the stretch sensor spirals around an elbow and/or a knee. In an example, it can form a half-spiral around an elbow and/or a knee. Alternatively, smart clothing can comprise: an article of clothing worn over a person's arm and/or leg; and an electromagnetic stretch (or bend) sensor comprising PVOH impregnated (or doped, embedded, or coated) with silver (or sliver alloy, silver chloride) particles or pieces; wherein the stretch sensor spirals around an elbow and/or a knee.

In an example, smart clothing can comprise: an article of clothing worn over a person's arm and/or leg; and an electromagnetic stretch (or bend) sensor comprising stretchable thread or yarn coated (or embedded) with silver (or sliver alloy, silver chloride) particles or pieces; wherein the stretch sensor spirals around an elbow and/or a knee. Smart clothing can comprise: an article of clothing which is configured to be worn over a person's arm and/or leg; and an electromagnetic stretch (or bend) sensor comprising wool yarn coated (or embedded) with conductive metal particles, pieces, or microstructures; wherein the stretch sensor spirals around an elbow and/or a knee. In an example, it can form a half-spiral around an elbow and/or a knee. Smart clothing can comprise: an article of clothing worn over a person's arm and/or leg; and an electromagnetic stretch (or bend) sensor printed onto the article of clothing with a silicone-based ink which has been impregnated (or doped) with carbon (particles, nanotubes, microstructures, graphene, graphite); wherein the stretch sensor spirals around an elbow and/or a knee. Alternatively, smart clothing can comprise: an article of clothing worn over a person's arm and/or leg; and an electromagnetic stretch (or bend) sensor printed onto the article of clothing with conductive ink or resin which has been impregnated (or doped) with steel particles or pieces; wherein the stretch sensor spirals around an elbow and/or a knee. In an example, it can form a half-spiral around an elbow and/or a knee. Smart clothing can comprise: an article of clothing which is configured to be worn over a person's arm and/or leg; and an electromagnetic stretch (or bend) sensor comprising cotton (thread or fiber) coated (or embedded) with carbon (particles, nanotubes, microstructures, graphene, graphite); wherein the stretch sensor longitudinally spans the dorsal surface of an elbow and/or the ventral surface of a knee. Alternatively, smart clothing can comprise: an article of clothing worn over a person's arm and/or leg; and an electromagnetic stretch (or bend) sensor comprising latex impregnated (or doped, embedded, or coated) with copper (or copper alloy) particles or pieces; wherein the stretch sensor longitudinally spans the dorsal surface of an elbow and/or the ventral surface of a knee.

and an electromagnetic stretch (or bend) sensor comprising PEG, PET, or PTFE impregnated (or doped, embedded, or coated) with tungsten particles or pieces; wherein the stretch sensor longitudinally spans the dorsal surface of an elbow and/or the ventral surface of a knee. Smart clothing can comprise: an article of clothing worn over a person's arm and/or leg; and an electromagnetic stretch (or bend) sensor comprising rayon (thread or yarn) coated (or embedded) with tungsten particles or pieces; wherein the stretch sensor longitudinally spans the dorsal surface of an elbow and/or the ventral surface of a knee. Smart clothing can comprise: an article of clothing worn over a person's arm and/or leg; and an electromagnetic stretch (or bend) sensor comprising silk thread coated (or embedded) with gallium; wherein the stretch sensor longitudinally spans the dorsal surface of an elbow and/or the ventral surface of a knee. Smart clothing can comprise: an article of clothing which is configured to be worn over a person's arm and/or leg; and an electromagnetic stretch (or bend) sensor comprising TPE, TPU, and/or thermoplastic vulcanizate (TPV) impregnated (or doped, embedded, or coated) with copper (or copper alloy); wherein the stretch sensor longitudinally spans the dorsal surface of an elbow and/or the ventral surface of a knee. Alternatively, smart clothing can comprise: an article of clothing worn over a person's arm and/or leg; and an electromagnetic stretch (or bend) sensor printed onto the article of clothing with a PDMS-based ink which has been impregnated (or doped) with aluminum (or aluminum alloy) particles or pieces; wherein the stretch sensor longitudinally spans the dorsal surface of an elbow and/or the ventral surface of a knee.

In another example, smart clothing can comprise: an article of clothing worn over a person's arm and/or leg; and a stretch (or bend) sensor comprising silicone, silicone rubber, and/or PDMS impregnated (or doped, embedded, or coated) with gold (or gold alloy); wherein the stretch (or bend) sensor spans between 10% and 60% of the circumference of the arm or leg. Alternatively, smart clothing can comprise: an article of clothing worn over a person's arm and/or leg; and a stretch (or bend) sensor comprising stretchable thread or yarn coated (or embedded) with conductive metal particles, pieces, or microstructures; wherein the stretch (or bend) sensor spans between 10% and 60% of the circumference of the arm or leg. Alternatively, smart clothing can comprise: an article of clothing which is configured to be worn over a person's arm and/or leg; and a stretch (or bend) sensor printed onto the article of clothing with a polymer-based ink which has been impregnated (or doped) with conductive metal particles, pieces, or microstructures; wherein the stretch (or bend) sensor spans between 10% and 60% of the circumference of the arm or leg. Smart clothing can comprise: an article of clothing worn over a person's arm and/or leg; and a stretch (or bend) sensor printed onto the article of clothing with conductive ink or resin which has been impregnated (or doped) with niobium; wherein the stretch (or bend) sensor spans between 10% and 60% of the circumference of the arm or leg. Smart clothing can comprise: an article of clothing; and a stretch (or bend) sensor comprising cotton (thread or fiber) coated (or embedded) with gallium; wherein the stretch (or bend) sensor is woven, sewn, or embroidered into the article of clothing. Smart clothing can comprise: an article of clothing; and a stretch (or bend) sensor comprising nylon (thread or yarn) coated (or embedded) with copper (or copper alloy) particles or pieces; wherein the stretch (or bend) sensor is woven, sewn, or embroidered into the article of clothing.

In an example, smart clothing can comprise: an article of clothing; and a stretch (or bend) sensor comprising wool yarn coated (or embedded) with copper (or copper alloy) particles or pieces; wherein the stretch (or bend) sensor is woven, sewn, or embroidered into the article of clothing Smart clothing can comprise: an article of clothing; and a stretch (or bend) sensor comprising cellulose, hydroxypropyl cellulose, and/or HPMC impregnated (or doped, embedded, or coated) with silver (or sliver alloy, silver chloride); wherein the stretch (or bend) sensor is sewn onto, woven into, adhered to, inserted into, or otherwise attached to the article of clothing. Alternatively, smart clothing can comprise: an article of clothing; and a stretch (or bend) sensor comprising PEDOT/PSS impregnated (or doped, embedded, or coated) with niobium; wherein the stretch (or bend) sensor is sewn onto, woven into, adhered to, inserted into, or otherwise attached to the article of clothing. Smart clothing can comprise: an article of clothing; and a stretch (or bend) sensor comprising polypropylene glycol impregnated (or doped, embedded, or coated) with gallium; wherein the stretch (or bend) sensor is sewn onto, woven into, adhered to, inserted into, or otherwise attached to the article of clothing. Alternatively, smart clothing can comprise: an article of clothing; and a stretch (or bend) sensor comprising silicone, silicone rubber, and/or PDMS impregnated (or doped, embedded, or coated) with gallium; wherein the stretch (or bend) sensor is sewn onto, woven into, adhered to, inserted into, or otherwise attached to the article of clothing. Alternatively, smart clothing can comprise: an article of clothing; and a stretch (or bend) sensor comprising TPE, TPU, and/or TPV impregnated (or doped, embedded, or coated) with steel particles or pieces; wherein the stretch (or bend) sensor is sewn onto, woven into, adhered to, inserted into, or otherwise attached to the article of clothing.

In another example, smart clothing can comprise: an article of clothing; and a stretch (or bend) sensor comprising an elastic material and/or an elastomeric polymer impregnated (or doped, embedded, or coated) with silver (or sliver alloy, silver chloride) particles or pieces. Smart clothing can comprise: an article of clothing; and a stretch (or bend) sensor comprising cotton (thread or fiber) coated (or embedded) with gold (or gold alloy) particles or pieces. Smart clothing can comprise: an article of clothing; and a stretch (or bend) sensor comprising PEDOT/PSS impregnated (or doped, embedded, or coated) with gold (or gold alloy) particles or pieces. Alternatively, smart clothing can comprise: an article of clothing; and a stretch (or bend) sensor comprising PEG, PET, or PTFE impregnated (or doped, embedded, or coated) with tungsten particles or pieces. Smart clothing can comprise: an article of clothing; and a stretch (or bend) sensor comprising polyurethane impregnated (or doped, embedded, or coated) with steel particles or pieces. Alternatively, smart clothing can comprise: an article of clothing; and a stretch (or bend) sensor comprising rayon (thread or yarn) coated (or embedded) with nickel (or nickel alloy) particles or pieces.

In an example, smart clothing can comprise: an article of clothing; and a stretch (or bend) sensor comprising SEBS impregnated (or doped, embedded, or coated) with nickel (or nickel alloy) particles or pieces. Smart clothing can comprise: an article of clothing; and a stretch (or bend) sensor printed onto the article of clothing with a PDMS-based ink which has been impregnated (or doped) with aluminum (or aluminum alloy) particles or pieces. Smart clothing can comprise: an article of clothing; and a stretch (or bend) sensor printed onto the article of clothing with a silicone-based ink which has been impregnated (or doped) with tungsten particles or pieces. Smart clothing can comprise: an article of clothing worn over a person's arm and/or leg; and an electromagnetic stretch (or bend) sensor comprising acrylic (yarn, thread, or fiber) coated (or embedded) with gold (or gold alloy); wherein the stretch sensor spirals around an elbow and/or a knee. Alternatively, smart clothing can comprise: an article of clothing worn over a person's arm and/or leg; and an electromagnetic stretch (or bend) sensor comprising cellulose, hydroxypropyl cellulose, and/or HPMC impregnated (or doped, embedded, or coated) with copper (or copper alloy); wherein the stretch sensor spirals around an elbow and/or a knee. Smart clothing can comprise: an article of clothing worn over a person's arm and/or leg; and an electromagnetic stretch (or bend) sensor comprising cotton (thread or fiber) coated (or embedded) with nickel (or nickel alloy) particles or pieces; wherein the stretch sensor spirals around an elbow and/or a knee.

In an example, a device or system for capturing human motion can comprise: an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; a first inertial motion sensor which is incorporated into or attached to the portion at the first cross-sectional circumference; a second inertial motion sensor which is incorporated into or attached to the portion at the second cross-sectional circumference; a first stretch (or bend) sensor which is incorporated into or attached to the portion and spans the body joint between the first cross-sectional circumference and the second cross-sectional circumference, and wherein the first stretch sensor collects data concerning the transmission of energy through the first stretch sensor; a second stretch (or bend) sensor which is incorporated into or attached to the portion and spans the body joint between the first cross-sectional circumference and the second cross-sectional circumference, and wherein the second stretch sensor collects data concerning the transmission of energy through the second stretch sensor; and a data processor which analyzes data from the first inertial motion sensor, the second inertial motion sensor, the first stretch sensor, and the second stretch sensor to measure a configuration or motion of the body joint.

In an example, a device or system for capturing human motion can comprise: an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; a first inertial motion sensor which is incorporated into or attached to the portion at the first cross-sectional circumference; a second inertial motion sensor which is incorporated into or attached to the portion at the second cross-sectional circumference; a first stretch (or bend) sensor which is incorporated into or attached to the portion and spans the body joint between the first cross-sectional circumference and the second cross-sectional circumference; wherein the first stretch (or bend) sensor is made from a thermoplastic elastomer which has been embedded, impregnated, doped, or coated with conductive material; and wherein the first stretch sensor collects data concerning the transmission of energy through the first stretch sensor; a second stretch (or bend) sensor which is incorporated into or attached to the portion and spans the body joint between the first cross-sectional circumference and the second cross-sectional circumference; wherein the second stretch (or bend) sensor is made from a thermoplastic elastomer which has been embedded, impregnated, doped, or coated with conductive material; and wherein the second stretch sensor collects data concerning the transmission of energy through the second stretch sensor; and a data processor which analyzes data from the first inertial motion sensor, the second inertial motion sensor, the first stretch sensor, and the second stretch sensor to measure a configuration or motion of the body joint.

In an example, a device or system for capturing human motion can comprise: an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; a first inertial motion sensor which is incorporated into or attached to the portion at the first cross-sectional circumference; a second inertial motion sensor which is incorporated into or attached to the portion at the second cross-sectional circumference; a first stretch (or bend) sensor which is incorporated into or attached to the portion and spans the body joint between the first cross-sectional circumference and the second cross-sectional circumference; wherein the first stretch (or bend) sensor is made from polydimethylsiloxane (PDMS) which has been embedded, impregnated, doped, or coated with conductive material; and wherein the first stretch sensor collects data concerning the transmission of energy through the first stretch sensor; a second stretch (or bend) sensor which is incorporated into or attached to the portion and spans the body joint between the first cross-sectional circumference and the second cross-sectional circumference; wherein the second stretch (or bend) sensor is made from polydimethylsiloxane (PDMS) which has been embedded, impregnated, doped, or coated with conductive material; and wherein the second stretch sensor collects data concerning the transmission of energy through the second stretch sensor; and a data processor which analyzes data from the first inertial motion sensor, the second inertial motion sensor, the first stretch sensor, and the second stretch sensor to measure a configuration or motion of the body joint.

In an example, Motion Recognition Clothing™ can be embodied in a wearable device for measuring body joint motion and/or configuration comprising: (a) a first energy pathway, wherein this first energy pathway is configured to span the surface of a portion of a person's body which contains at least one body joint, wherein this first energy pathway is moved from a first configuration to a second configuration by movement of the at least one body joint, and wherein this first energy pathway has a first energy flow when the pathway is in the first configuration and has a second energy flow when the pathway is in the second configuration; (b) a first energy sensor which measures energy flow through or from the first energy pathway; (c) a second energy pathway, wherein this second energy pathway is configured to span the surface of the portion of a person's body which contains the at least one body joint, wherein this second energy pathway is moved from a third configuration to a fourth configuration by movement of the at least one body joint, and wherein this second energy pathway has a third energy flow when the pathway is in the third configuration and has a fourth energy flow when the pathway is in the fourth configuration; (d) a second energy sensor which measures energy flow through or from the second energy pathway, wherein data from the first energy sensor and data from the second energy sensor are analyzed together in order to measure the motion and/or configuration of the at least one body joint.

In an example, a first energy pathway and a second energy pathway can each have a longitudinal axis. In an example, a longitudinal axis of an energy pathway can span the surface of a body member containing a body joint in a proximal-to-distal manner. In this disclosure, the term "proximal" refers to locations in (or on) the person's body which are closer to the person's mass centroid or the person's heart. The term "distal" refers to locations in (or on) the person's body which are further from the person's mass centroid or the person's heart. In an example, a longitudinal axis of an energy pathway can span the surface of a body member containing a body joint in a circumferential or cross-sectional manner.

In an example, the geometric relationship between the longitudinal axis of a first energy pathway and the longitudinal axis of a second energy pathway can be selected from the group consisting of: substantially parallel; separated by a substantially-constant distance; separated by a substantially-constant number of radial degrees of the cross-sectional perimeter of a body member; separated by a substantially-constant percentage of the cross-sectional perimeter of a body member; forming vectors which intersect in 3D space at a right angle; substantially-parallel as they span a distal portion of a joint and diverging as they span a proximal portion of a joint; substantially-parallel as they span a proximal portion of a joint and diverging as they span a distal portion of a joint; substantially perpendicular; intersecting at an acute angle; forming vectors which intersect in 3D space at an acute angle; substantially diagonal to each other; plaited together; woven together; braided together; combining to form a 3D lattice, mesh, or grid; differing in length; nested; forming a rainbow arc configuration; radial vectors with a common point of convergence; straight vectors with a common convergence point; and arcuate elements with a common convergence point.

In an example, two energy pathways spanning the same body joint can differ in the angles at which they span the longitudinal axis of the body member which contains the body joint. In an example, having different energy pathways span a body joint at different angles can be especially useful for measuring the motion and/or configuration of ball-and-socket or other complex motion joints. In an example, two energy pathways can have longitudinal axes which are substantially perpendicular as they span the body member which contains a body joint. In an example, multiple energy pathways spanning the same body joint can form inter-pathway areas which, when projected from 3D space onto a 2D plane, are squares or rectangles. In an example, two energy pathways can be woven together in a substantially-parallel manner to form a textile wherein this textile is then used to make a garment which spans a portion of a body member in a curvaceous 3D manner. In an example, two energy pathways can be woven together in a substantially-perpendicular manner to form a textile wherein this textile is then used to make a garment which spans a portion of a body member in a curvaceous 3D manner. In an example, two energy pathways can have longitudinal axes which intersect at acute angles as they span the body member which contains a body joint.

In an example, multiple energy pathways spanning the same body joint can form inter-pathway areas which, when projected from 3D space onto a 2D plane, are rhombuses, diamonds, trapezoids, parallelograms, triangles, or hexagons. In an example, energy pathways can be part of a mesh which is an array of one or more shapes selected from the group consisting of: square elements; rectangular elements; diamond elements; rhomboid elements; parallelogram elements; trapezoidal elements; triangular elements; hexagonal elements; circular elements; and elliptical elements.

In an example, a first energy pathway and a second energy pathway can each have a circular, semi-circular, or other conic section shape axis. In an example, a circular, semi-circular, or other conic section shape axis can span all or part of the cross-sectional perimeter of a body member containing a body joint. In an example, one or more aspects of the geometric relationship between these two axes can be selected from the group consisting of: substantially parallel; separated by a substantially-constant distance; intersecting at an acute angle; forming vectors which intersect in 3D space at an acute angle; combining to form a 3D mesh or grid; differing in length; substantially concentric; nested; differing in diameter; knitted together in loops; and tangential.

In an example, a first energy pathway can have an axis which spans a body member in a longitudinal manner and a second energy pathway can have an axis which spans the same body member in a circular, semi-circular, or other conic sectional manner. In an example, the first energy pathway can span the surface of a body member containing a body joint in a proximal-to-distal manner. In an example, the second energy pathway can span the surface of the body member in a circular, semi-circular, or other conic sectional manner. In an example, one or more aspects of the geometric relationship between the first energy pathway and the second energy pathway can be selected from the group consisting of: substantially perpendicular; intersecting at a right angle; intersecting at an acute angle; defining square-shaped spaces (when projected onto a 2D plane) as they intersect; defining rhomboid-shaped spaces (when projected onto a 2D plane) as they intersect; defining trapezoid-shaped spaces (when projected onto a 2D plane) as they intersect; plaited together; woven together; braided together; combining to form a 3D mesh or grid; overlapping; and tangential.

In an example, an energy pathway can have a substantially straight configuration when a joint is fully extended. In an example, an energy pathway can have an arcuate shape, even when a joint is fully extended. In an example, an energy pathway can have a shape comprising a repeating waveform selected from the group consisting of: simple sinusoidal wave; composite sinusoidal wave; saw-tooth wave or zig-zag; and square wave. In an example, an energy pathway can have a shape which is a conic section. In an example, an energy pathway can have a shape which is a spiral or helix. In an example, an energy pathway can have a shape which is a chain of loops.

In an example, the flows of energy through first and second energy pathways can be independent or be separate as these flows span a body member containing a body joint. In an example, the flows of energy through first and second energy pathways can interact or combine with each other as these flows span a body member containing a body joint. In an example, first and second energy pathways can be in electromagnetic communication with each other as they span a body joint. In an example, first and second energy pathways can be in mechanical communication with each other as they span a body joint. In an example, first and second energy pathways can be in optical communication with each other as they span a body joint. In an example, first and second energy pathways can be in sonic communication with each other as they span a body joint.

In an example, first and second energy pathways which span a body member which contains a body joint can differ in the angle at which they span the body member. In an example, combined multivariate analysis of data from both the first and second energy pathways can provide more accurate measurement of body joint motion and/or configuration than data from either the first energy pathway or the second energy pathway alone. In an example, data from the first energy pathway can provide more accurate measurement of body joint motion over a first range of motion and data from the second energy pathway can provide more accurate measurement of body joint motion over a second range of motion. When analyzed together, data from the first and second energy pathways reduce error in measuring the full range of joint motion.

In an example, first and second energy pathways which span a body member which contains a body joint can differ in length. In an example, combined multivariate analysis of data from both the first and second energy pathways can provide more accurate measurement of body joint motion than data from either the first energy pathway or the second energy pathway alone. In an example, data from a longer energy pathway can provide more accurate measurement of body joint motion over a first range of motion and data from a shorter energy pathway can provide more accurate measurement of body joint motion over a second range of motion. When analyzed together, data from the longer and shorter energy pathways reduce error in measuring the full range of joint motion.

In an example, first and second energy pathways which span a body member which contains a body joint can differ in longitudinal curvature or convolution. In an example, combined multivariate analysis of data from both the first and second energy pathways can provide more accurate measurement of body joint motion than data from either the first energy pathway or the second energy pathway alone. In an example, an energy pathway with a sinusoidal, zigzag, or other repeated wave shape can have a higher curvature or convolution if it has a waveform with a larger amplitude or higher wave frequency. In an example, data from a highly curved or convoluted energy pathway can provide more accurate measurement of body joint motion over a first range of motion and data from a less curved or convoluted energy pathway can provide more accurate measurement of body joint motion over a second range of motion. When analyzed together, data from the highly curved or convoluted and the less curved or convoluted energy pathways reduce error in measuring the full range of joint motion.

In an example, first and second energy pathways which span a body member which contains a body joint can differ in flexibility. In an example, combined multivariate analysis of data from both the first and second energy pathways can provide more accurate measurement of body joint motion than data from either the first energy pathway or the second energy pathway alone. In an example, data from a more-flexible energy pathway can provide more accurate measurement of body joint motion over a first range of motion and data from a less-flexible energy pathway can provide more accurate measurement of body joint motion over a second range of motion. When analyzed together, data from the more-flexible and less-flexible energy pathways reduce error in measuring the full range of joint motion.

In an example, first and second energy pathways which span a body member which contains a body joint can differ in elasticity. In an example, combined multivariate analysis of data from both the first and second energy pathways can provide more accurate measurement of body joint motion than data from either the first energy pathway or the second energy pathway alone. In an example, data from a more-elastic energy pathway can provide more accurate measurement of body joint motion over a first range of motion and data from a less-elastic energy pathway can provide more accurate measurement of body joint motion over a second range of motion. When analyzed together, data from the more-elastic and less-elastic energy pathways reduce error in measuring the full range of joint motion.

In an example, first and second energy pathways which span a body member which contains a body joint can differ in electrical resistance or impedance. In an example, combined multivariate analysis of data from both the first and second energy pathways can provide more accurate measurement of body joint motion than data from either the first energy pathway or the second energy pathway alone. In an example, data from a higher resistance or impedance energy pathway can provide more accurate measurement of body joint motion over a first range of motion and data from a lower resistance or impedance energy pathway can provide more accurate measurement of body joint motion over a second range of motion. When analyzed together, data from the higher resistance or impedance and the lower resistance or impedance pathways reduce error in measuring the full range of joint motion.

In an example, first and second energy pathways which span a body member which contains a body joint can differ in cross-sectional shape. In an example, combined multivariate analysis of data from both the first and second energy pathways can provide more accurate measurement of body joint motion than data from either the first energy pathway or the second energy pathway alone. In an example, data from a first energy pathway with a first cross-sectional shape can provide more accurate measurement of body joint motion over a first range of motion and data from a second energy pathway with a second cross-sectional shape can provide more accurate measurement of body joint motion over a second range of motion. When analyzed together, data from the first and second energy pathways reduce error in measuring the full range of joint motion.

In an example, a first energy pathway and a second energy pathway which both span the same body member which contains a body joint can differ by one or more parameters selected from the group consisting of: the angle at which they span the body joint; length; longitudinal curvature or convolution; longitudinal waveform; flexibility; elasticity; electrical resistance or impedance; transparency; and cross-sectional shape. In an example, combined multivariate analysis of data from both the first and second energy pathways can provide more accurate measurement of body joint motion than analysis of data from either the first energy pathway or the second energy pathway alone. In an example, data from the first energy pathway can provide more accurate measurement of body joint motion over a first range of motion and data from the second energy pathway can provide more accurate measurement of body joint motion over a second range of motion. When analyzed together, data from the first and second energy pathways reduce error in measuring the full range of joint motion.

In an example, combined, joint, or integrated multivariate analysis of data from multiple energy pathways spanning the same body joint yields measurement of the motion and/or configuration of a body joint with a statistically-significant lower error rate or error range than analysis of data from a single energy pathway spanning that body joint. In an example, combined, joint, or integrated multivariate analysis of data from multiple energy pathways spanning the same body joint yields measurement of the motion and/or configuration of a body joint with a statistically-significant lower error rate or error range than separate analysis of data from those energy pathways. In an example, the statistical significance of error reduction is at the $p<0.05$ level. In an example, statistical significance of error reduction is at the $p<0.01$ level. In an example, estimating the motion and/or configuration of a body joint angle using combined, joint, or integrated multivariate analysis of data from multiple energy pathways spanning that joint can yield an over-determined system of equations for joint angle estimation. This can help to reduce measurement error from factors such as: shifting or sliding of the energy pathways and/or a garment containing the energy pathways over the surface of the body; material fatigue and variability in the energy pathways; and interference between an external object or field and one side of the body member.

In an example, the relationship between energy flow in an energy pathway and the configuration of a body joint spanned by that energy pathway can be nonlinear and/or stochastic. In an example, the relationship between energy flow in an energy pathway and the configuration of a body joint spanned by that energy pathway can be analyzed using one or more multivariate statistical methods. In an example, data from multiple energy pathways can be jointly analyzed using one or more statistical methods selected from the group consisting of: multivariate linear regression or least squares estimation; factor analysis; Fourier Transformation; mean; median; multivariate logit; principal components analysis; spline function; auto-regression; centroid analysis; correlation; covariance; decision tree analysis; kinematic modeling; Kalman filter; linear discriminant analysis; linear transform; logarithmic function; logit analysis; Markov model; multivariate parametric classifiers; non-linear programming; orthogonal transformation; pattern recognition; random forest analysis; spectroscopic analysis; variance; artificial neural network; Bayesian filter or other Bayesian statistical method; chi-squared; eigenvalue decomposition; logit model; machine learning; power spectral density; power spectrum analysis; probit model; and time-series analysis.

In an example, repeated or cyclical patterns of movement such as walking or running can be identified and analyzed using Fourier analysis. In an example, the speed of repeated movement cycles can influence the functional relationship between the flow of energy through an energy pathway and the angle of a joint. In an example, the speed of repeated cycles can especially influence this functional relationship at the end-points of a cycle wherein joint movement reverses direction. In an example, analyzing and identifying the speed of repeated or cyclical patterns of movement using Fourier transform methods can improve the accuracy of measuring joint motion and configuration.

In an example, data from different energy pathways spanning the same body joint can be averaged together in order to improve accuracy and reduce error in the measurement of the motion and/or configuration of that joint. In an example, data from different energy pathways spanning the same body joint can be given different weights during different portions of the joint range of motion in order to improve accuracy and reduce error in the measurement of the motion and/or configuration of that joint. In an example, data from different energy pathways spanning the same body joint can be given different weights during different directions of joint motion (e.g. flexion vs. extension) in order to improve accuracy and reduce error in the measurement of the motion and/or configuration of that joint. In an example, data from different energy pathways spanning the same body joint can be given different weights during different movement speeds (e.g. fast movement vs. slow movement) of joint motion in order to improve accuracy and reduce error in the measurement of the motion and/or configuration of that joint. In an example, data from different energy pathways spanning the same body joint can be given different weights during different numbers of cycle repetition of joint motion in order to improve accuracy and reduce error in the measurement of the motion and/or configuration of that joint.

In an example, data from an energy pathway with anomalous results can be given less weight in order to improve accuracy and reduce error in the measurement of the motion and/or configuration of that joint. In an example, data from different energy pathways can analyzed to identify probable shifting of energy pathway location over the surface of the body (e.g. by shifting of a garment into which the pathways are integrated) and to compensate for this shifting when interpreting data from multiple energy pathways. In an example, data from different energy pathways can analyzed to identify probable loss of mechanical or electromagnetic communication between an energy pathway and the body and to compensate for this loss when interpreting data from multiple energy pathways. In an example, data from different energy pathways can analyzed to identify probable interference by an external object or field and to compensate for this interference when interpreting data from multiple energy pathways.

In an example, this device can be recalibrated in order to maintain accurate measurement of joint motion and/or configuration. In an example, recalibration can comprise comparing the results from using the energy pathways of the device to estimate the motion and/or configuration of a selected body joint or joints with parallel results from an alternative method of estimating joint motion and/or configuration of the body joint or joints. In an example, this device can be recalibrated when it is first worn by a specific person in order to be custom matched to that person's specific anatomy and/or body kinetics. In an example, this device can be recalibrated each time that it is worn in order to control for: changing environmental conditions; incorporation into different articles of clothing; changes or shifts in how an article of clothing is worn over a person's body;

changes in the anatomy or kinetics of a person's body over time; or other factors. In an example, this device can be recalibrated each time that a particular sequence of movements occurs in order to control for: possible shifts in how the energy pathways span a body member containing a body joint; changes in how material responses to bending, stretching, or elongation with repeated motions; changes in temperature; or other factors. In an example, this device can be recalibrated after a selected number of joint extension and contraction cycles. In an example, this device can be recalibrated after a selected number of movement sequences have occurred. In an example, this device can be recalibrated at selected usage time intervals. In an example, this device can be recalibrated each time that a significant change in environmental factors (such as temperature, humidity, GPS location, or atmospheric pressure) is detected.

In an example, changes in the flows of electromagnetic energy can be measured by one or more parameters selected from the group consisting of: voltage, resistance, impedance, amperage, current, phase, and wave pattern. In an example, an electromagnetic energy pathway can be comprised of electroconductive fibers, yarns, threads, strands, substrates, layers, or textiles. In an example, an electromagnetic energy sensor can be selected from the group consisting of: voltmeter, impedance sensor, magnetic field sensor, piezoelectric sensor, piezomechanical sensor, potentiometer, resistive bend sensor, variable-resistance sensor, electromyography (EMG) sensor, and Hall-effect sensor.

In an example, an electromagnetic energy pathway can be piezoelectric and/or piezoresistive. In an example, an electromagnetic energy pathway can generate electromagnetic energy when it is bent, stretched, elongated, and/or twisted and an electromagnetic energy sensor can measure generated electricity. In an example, the source of energy which flows through or from an energy pathway can be selected from the group consisting of: energy from a power source internal to the device; energy from a power source that is external to the device; and energy which is generated, transduced, or harvested by the device.

In an example, electromagnetic energy can be directed into an energy pathway at a first location and electromagnetic energy from the energy pathway can be measured from the energy pathway at a second location. In an example, wearable energy pathways can comprise non-conductive or less-conductive fibers, traces, yarns, strands, or textiles which are coated, impregnated, or otherwise integrated with conductive material or particles. In an example, a non-conductive or less-conductive fiber, trace, yarn, strand, or textile can be selected from the group consisting of: acetate, acrylic, cotton, denim, elastane, Kevlar, latex, linen, Lycra, neoprene, nylon, nylon, polyester, wool, silicon rubber, silk, spandex, Danconn or rayon. In an example, conductive material or particles used for coating or impregnation can be selected from the group consisting of: aluminum or aluminum alloy; carbon nanotubes, graphene, or other carbon-based material; magnesium; ceramic particles; copper or copper alloy; gold; nickel; polyaniline; silver; and steel.

In an example, an electronically-functional textile, fabric, garment, or wearable accessory can comprise one or more of the following: array of electroconductive members woven using a plain weave, rib weave, basket weave, twill weave, satin weave, leno weave, mock leno weave, or conan weave; array of fiber optic members woven using a plain weave, rib weave, basket weave, twill weave, satin weave, leno weave, mock leno weave, or conan weave; array of light-emitting fibers, threads, or yarns; array of sound-conducting members woven using a plain weave, rib weave, basket weave, twill weave, satin weave, leno weave, mock leno weave, leno and conan weave; array or mesh of electroconductive fibers; bendable fibers, threads, or yarns; bendable layer, trace, or substrate; elastic fibers, threads, or yarns; elastic layer, trace, or substrate; electroconductive fibers, threads, or yarns; electronically-functional bandage; electronically-functional tattoo; integrated array of electroconductive members; integrated array of fiber optic members; integrated array of sound-conducting members; interlaced electricity-conducting fibers, threads, or yarns; interlaced light-conducting fibers, threads, or yarns; interlaced sound-conducting fibers, threads, or yarns; light-emitting fibers, threads, or yarns; nonconductive fibers, threads, or yarns; nonconductive layer, substrate, or material; plaited fibers, threads, or yarns; sinusoidal fibers, threads, or yarns; stretchable fibers, threads, or yarns; stretchable layer, trace, or substrate; textile-based light display matrix; variable-resistance electroconductive fiber, thread, or yarn; variable-translucence fiber, thread, or yarn; water-resistant fibers, threads, or yarns; a layer or coating of metallic nanoparticles; a graphene layer; and water-resistant layer, trace, or substrate.

In an example, an array of energy pathways can be incorporated into an article of clothing which is, in turn, worn over a body member containing a body joint. Changes in energy conducted through these pathways can be used to estimate joint motion and/or configuration. In an example, an array of energy pathways can be directly attached to a body member containing a body joint. In an example, energy pathways can be incorporated into an article of clothing or directly attached to a body member using one or more means selected from the group consisting of: adhesion, armband, article of clothing, bangle, belt, bracelet, buckle, button, clasp, clip, elastic band, elastic garment, eyewear, fabric layer, garment channel, garment pocket, gluing, hook, hook-and-eye attachment mechanism, incorporation into a bandage, incorporation into a tattoo, knitting, loop, magnetism, melting, metal fibers, nanoscale fibers, necklace, pin, polymer fibers, sewing, skin-adhesive patch, smart watch, snap, strands, strap, tape, textile channel, textile fibers, thermal bonding, tubular garment, waist band, weaving, wrist band, yarn, and zipper.

In an example, energy pathways which measure the motion and/or configuration of one or more body joints can be incorporated into an article of clothing or clothing accessory selected from the group consisting of: an upper body garment such as a shirt, t-shirt, blouse, jacket, hoodie, sweatshirt, undershirt, brassier, girdle, blouse, or glove; a lower body garment such as a pair of pants, sweatpants, trousers, slacks, leggings, tights, underpants, pantyhose, shorts, or sock; a full-body garment such as a union suit, jump suit, pair of overalls, or dress; a clothing accessory such as shoe, boot, insole, hat, cap, headband, armband, strap, torso band, tubular accessory, wristband, other band, knee or elbow brace, back brace, knee or elbow pad, belt, bandage, electronic tattoo, or wearable patch.

In various examples, an array of energy pathways can measure one or more joint configurations and/or motions selected from the group consisting of: eversion, extension, flexion, and/or inversion of the ankle; abduction, extension, flexion, lateral bending, and/or rotation of the spine; eversion, extension, flexion, and/or inversion of the elbow; extension and/or flexion of the finger or thumb; pronation, rotation, and/or supination of the forearm; abduction, adduction, extension, flexion, and/or rotation of the hip; extension and/or flexion of the jaw; abduction, adduction, extension, and/or flexion of the knee; eversion and/or inversion of the mid-tarsal; abduction, extension, flexion, and/or rotation of the neck; abduction, adduction, extension, flexion, and/or rotation of the shoulder; extension and/or flexion of the toe; and abduction, extension, flexion, and/or ulnar deviation or radial deviation of the wrist.

In an example, this device can span the surface of the portion of the body containing one or more body joints selected from the group consisting of: ankle, elbow, finger, forearm, hip, jaw, knee, mid-tarsal, neck, shoulder, spine, thumb, toe, and wrist. In an example, this device can span the surface of a body member containing the finger and thumb. In an example, this device can span the surface of a body member containing the finger, forearm, thumb and wrist. In an example, this device can span the surface of a body member containing the elbow, forearm and wrist. In an example, this device can span the surface of a body member containing the elbow. In an example, this device can span the surface of the body containing the elbow, forearm, shoulder and spine. In an example, this device can span the surface of a body member containing the hip and knee. In an example, this device can span the surface of a body member containing the spine. In an example, this device can span the surface of a body member containing the ankle, mid-tarsal and toe. In an example, this device can span the surface of the portion of the body containing the neck, shoulder and spine.

In an example, Motion Recognition Clothing™ can also include a data control unit which further comprises one or more components selected from the group consisting of: a data processing component, a data communication component, a power source, a human-to-computer user interface, a computer-to-human interface, and a digital memory. In an example, a data control unit can be temporarily detached so that the remaining wearable portion of the invention can be washed.

In an example, a data processing component can perform one or more functions selected from the group consisting of: amplify sensor signals, analyze data, analyze sensor information, convert analog signals to digital signals, determine a functional relationship between signal variation and joint angle variation, estimate joint angle, filter signals, model joint configuration, record data, run software applications, run software programs, and store data in memory. In an example, a data communication component can perform one or more functions selected from the group consisting of: transmit and receive data via Bluetooth, WiFi, Zigbee, or other wireless communication modality; transmit and receive data to and from a mobile electronic device such as a cellular phone, mobile phone, smart phone, electronic tablet; transmit and receive data to and from a separate wearable device such as a smart watch or electronically-functional eyewear; transmit and receive data to and from the internet; send and receive phone calls and electronic messages; transmit and receive data to and from a home appliance and/or home control system; and transmit and receive data to and from an implantable medical device.

In an example, a power source can be selected from the group consisting of: a rechargeable or replaceable battery; an energy harvesting member which harvests, transduces, or generates energy from body motion or kinetic energy, body thermal energy, or body biochemical energy; an energy harvesting member which harvests, transduces, or generates energy from ambient light energy or ambient electromagnetic energy. In an example, a human-to-computer interface can further comprise one or more members selected from the group consisting of: a button, knob, or dial; a display screen; a gesture-recognition interface; a holographic user interface; a microphone; a physical keypad or keyboard; a pressure-sensitive textile array; a spectroscopic sensor; a speech or voice recognition interface; a touch screen; a virtual keypad or keyboard; an electronically-functional textile interface; and an eye gaze tracker. In an example, a computer-to-human interface can further comprise one or more members selected from the group consisting of: a coherent-light image projector; a display screen; a holographic user interface; a laser; a myostimulating member; a neurostimulating member; a non-coherent-light image projector; a speaker or other sound-emitting member; a speech or voice recognition interface; a synthesized voice; a vibrating or other tactile sensation creating member; an electromagnetic energy emitter; an electronically-functional textile interface; an infrared light emitter; an infrared light projector; and an LED or LED array.

In an example, Motion Recognition Clothing™ can further comprise one or more motion-related sensors selected from the group consisting of: dual-axial accelerometer, tri-axial accelerometer, other multi-axial accelerometer, gyroscope, inclinometer or tilt sensor, goniometer, GPS or other location sensor, other inertial or motion sensor, goniometer, and kinematic sensor. In an example, Motion Recognition Clothing™ can further comprise one or more electromagnetic energy sensors selected from the group consisting of: electroencephalography (EEG) sensor, peripheral neurosensor, electromyography (EMG) sensor, Hall-effect sensor, electromagnetic field sensor, electrocardiogram (ECG) sensor, cardiac monitor, EOG sensor, galvanic skin response (GSR) sensor, impedance sensor, compass, magnometer, magnetic sensor, potentiometer, variable-resistance sensor, resistive bend sensor, piezoelectric sensor, piezomechanical sensor, piezoresistive sensor, and other electromagnetic sensor.

In an example, Motion Recognition Clothing™ can further comprise one or more force-related sensors selected from the group consisting of: blood pressure sensor, heart rate monitor, capacitive sensor, force sensor, particulate force transducer, electromagnetic pressure sensor, other pressure sensor, torque sensor, and torsion sensor. In an example, Motion Recognition Clothing™ can further comprise one or more biochemical sensors selected from the group consisting of: electrochemical sensor, biochemical sensor, glucose sensor, chemoreceptor sensor, gas sensor, microbial sensor, micro-sampling tissue or body fluid sensor, pH level sensor, and photochemical sensor. In an example, Motion Recognition Clothing™ can further comprise one or more small-scale sensors selected from the group consisting of: Micro-Electro-Mechanical System (MEMS) sensor, nanoscale sensor, nanotube sensor, and nanoparticle sensor. In an example, Motion Recognition Clothing™ can further comprise one or more additional sensors selected from the group consisting of: humidity sensor, moisture sensor, thermometer, temperature sensor, flow sensor, differential transducer sensor, elastomeric sensor, vibration sensor, helical sensor, revolute joint sensor, ionizing radiation sensor, neurosensor, food consumption sensor, and eye-tracking sensor.

In various examples, Motion Recognition Clothing™ can further comprise one or more additional wearable sensors. In various examples, these one or more additional wearable sensors can be in kinetic, electromagnetic, optical, sonic, fluid, and/or chemical communication with a person's body. In various examples, one or more additional wearable sensors can be selected from the group consisting of: dual-axial accelerometer, tri-axial accelerometer, other multi-axial accelerometer, gyroscope, inclinometer or tilt sensor, goniometer, GPS or other location sensor, other inertial or motion sensor, goniometer, kinematic sensor; electroencephalography (EEG) sensor, peripheral neurosensor, electromyography (EMG) sensor, Hall-effect sensor, electromagnetic field sensor, electrocardiogram (ECG) sensor, cardiac monitor, EOG sensor, galvanic skin response (GSR) sensor, impedance sensor, compass, magnetometer, magnetic sensor, potentiometer, variable-resistance sensor, resistive bend sensor, piezoelectric sensor, piezomechanical sensor, piezoresistive sensor, other electromagnetic sensor; camera, other imaging member, photoelectric sensor, light intensity sensor, infrared light sensor, ultraviolet light sensor, spectroscopy sensor, near-infrared spectroscopy sensor, Raman spectroscopy sensor, spectral analysis sensor, spectrometry sensor, spectrophotometer sensor, chromatography sensor, other light-spectrum-analyzing sensor, fluorescence sensor, blood oximetry sensor, optoelectronic sensor, optical code scanner, laser sensor, optical strain detector, variable-translucence sensor; microphone, ultrasonic sensor, acoustic sensor, heart rate sensor, respiration or pulmonary function monitor, respiratory rate sensor, CPAP monitor; blood pressure sensor, heart rate monitor, capacitive sensor, force sensor, particulate force transducer, electromagnetic pressure sensor, other pressure sensor, torque sensor, torsion sensor; electrochemical sensor, biochemical sensor, glucose sensor, chemoreceptor sensor, gas sensor, microbial sensor, micro-sampling tissue or body fluid sensor, pH level sensor, photochemical sensor; Micro-Electro-Mechanical System (MEMS) sensor, nanoscale sensor, nanotube sensor, nanoparticle sensor; humidity sensor, moisture sensor; thermometer, temperature sensor; flow sensor; differential transducer sensor, elastomeric sensor, vibration sensor, helical sensor, revolute joint sensor, ionizing radiation sensor, neurosensor; food consumption sensor, and eye tracking sensor.

In an example, Motion Recognition Clothing™ can further comprise one or more actuators selected from the group consisting of: brushless DC motor, brush-type DC motor, electric motor, electromagnetic actuator, hydraulic actuator, induction motor, MEMS actuator, piezoelectric actuator, pneumatic actuator, and stepper motor. In an example, one or more actuators can adjust the fit and/or elasticity of a garment containing energy pathways in order to improve its ability to measure joint motion and/or configuration.

In an example, Motion Recognition Clothing™ can be used for athletic training, sports performance analysis, sports motion capture, and fan engagement. In an example, Motion Recognition Clothing™ can be useful for training and motion capture for sports which involve extensive and/or complex lower-body motion (such as soccer, bicycling, and running) which are not well measured by single-location (wrist-worn) accelerometers. In an example, Motion Recognition Clothing™ can be useful for training and motion capture for sports which involve complex upper-body motion (such as basketball, tennis, golf, baseball, Frisbee, and fencing) which are not well measured by single-location accelerometers.

In an example, Motion Recognition Clothing™ can be used for health, fitness, and medical applications. In an example, Motion Recognition Clothing™ can be used for caloric expenditure measurement, energy balance management, weight management, and caloric intake monitoring applications. In an example, Motion Recognition Clothing™ can be used for virtual exercise. In an example, Motion Recognition Clothing™ can be used for real-time avoidance of repeated motion injuries, injuries due to poor posture, and stress-related injuries including back injuries and carpal tunnel syndrome. In an example, Motion Recognition Clothing™ can be used for diagnostic and therapy-evaluation purposes including: range of motion assessment, gait analysis, biomechanical analysis, posture evaluation and correction, ergonomic assessment, fall prevention and detection, spinal motion assessment, rehabilitation assessment, biofeedback, pulse monitoring, respiratory function assessment, plethysmography, cardiac function monitoring, orthopedic therapy, physical therapy, orthotic design and fitting, and pronation analysis. In an example, Motion Recognition Clothing™ can be used for telemedicine and/or telesurgery applications.

In an example, Motion Recognition Clothing™ can be used for entertainment, gaming, and artistic purposes. In an example, Motion Recognition Clothing™ can be used for animation of an avatar in virtual reality and/or computer gaming. In an example, Motion Recognition Clothing™ can be used for animation of an animated character in motion picture making or other visual animation applications. In an example, Motion Recognition Clothing™ can be used for dance instruction, dance performance, and other performance art applications. In an example, Motion Recognition Clothing™ can be used for instruction and motion capture for playing musical instruments.

In an example, Motion Recognition Clothing™ can be used for communication and computer interface purposes. In an example, Motion Recognition Clothing™ can be used for telepresence, teleconferencing, telecommunication, avatar animation, and virtual commerce. In an example, Motion Recognition Clothing™ can be used as part of a gesture recognition human-to-computer user interface. In an example, Motion Recognition Clothing™ be can be used for telerobotics to enable remote control of the actions of a robot.

In various examples, one or more applications for Motion Recognition Clothing™ can be selected from group consisting of: athletic training and motion capture for sports which involve extensive lower-body motion (such as bicycling and soccer), extensive arm motion (such as tennis and golf), extensive lower-body motion (such as bicycling and running), extensive spinal motion, extensive forearm motion (such as tennis and golf), wrist motion (such as tennis, golf, and Frisbee), ankle motion (such as running and soccer), finger and hand motion (such as tennis, golf, baseball, and fencing), athletic performance measurement and improvement; and entertainment, gaming, and artistic applications (such as animated pictures, avatar animation, computer animation, computer gaming, dance instruction, dance performance, gaming input devices, graphical animation, motion capture, motion picture animation, motion pictures, movie making, performance arts, training and motion capture for playing musical instruments, virtual gaming, virtual reality); and health, fitness, and medical applications (such as avoidance of repeated motion injuries, biofeedback, biomechanical analysis, caloric expenditure measurement, caloric intake monitoring, cardiac function monitoring, congestive heart failure assessment, energy balance, ergonomic evaluation, fall prevention and detection, gait analysis, medical diagnosis, medical therapy, nutritional monitoring and improvement, orthopedic therapy, orthotic design and fitting, physical therapy, plethysmography, post-operative therapy, posture correction, pronation analysis, pulse monitoring, range of motion assessment, rehabilitation assessment, repetitive stress injury avoidance, respiratory function analysis, spinal injury avoidance, spinal motion assessment, telemedicine, telesurgery, virtual exercise, weight management); and human-computer interface and telecommunication (such as gesture recognition, telerobotics, telesurgery, telepresence, notifications, telecommunication, teleconferencing, telepresence, telerobotics, virtual commerce, and virtual reality interaction).

In an example, a wearable device for measuring the configuration or motion of a human body joint can comprise: (a) a joint-spanning triangular-element mesh which is comprised of linked triangular elements and which is configured to span the surface of a portion of the human body which contains a human body joint; and (b) a plurality of electromagnetic energy sensors which measure electromagnetic energy from different locations on the joint-spanning triangular-element mesh, wherein changes in the configuration or motion of the joint-spanning mesh change the pattern of electromagnetic energy which is measured by the plurality of electromagnetic energy sensors, and wherein data from the plurality of electromagnetic energy sensors are jointly analyzed to estimate the configuration or motion of the human body joint.

In an example, a wearable device for measuring the configuration or motion of a human body joint can comprise: (a) a joint-spanning hexagonal-element mesh which is comprised of linked hexagonal elements and which is configured to span the surface of a portion of the human body which contains a human body joint; and (b) a plurality of electromagnetic energy sensors which measure electromagnetic energy from different locations on the joint-spanning hexagonal-element mesh, wherein changes in the configuration or motion of the joint-spanning mesh change the pattern of electromagnetic energy which is measured by the plurality of electromagnetic energy sensors, and wherein data from the plurality of electromagnetic energy sensors are jointly analyzed to estimate the configuration or motion of the human body joint.

In an example, a wearable device for measuring the configuration or motion of a human body joint can comprise: (a) a joint-spanning spiral member which is configured to spiral around the surface of a portion of the human body which contains a human body joint; and (b) a plurality of electromagnetic energy sensors which measure electromagnetic energy from different locations on the joint-spanning spiral member, wherein changes in the configuration or motion of the joint-spanning mesh change the pattern of electromagnetic energy which is measured by the plurality of electromagnetic energy sensors, and wherein data from the plurality of electromagnetic energy sensors are jointly analyzed to estimate the configuration or motion of the human body joint.

In an example, a first energy pathway and a second energy pathway can be part of a mesh which is an array of one or more element shapes selected from the group consisting of: square elements; rectangular elements; diamond elements; rhomboid elements; parallelogram elements; triangular elements; hexagonal elements; circular elements; and elliptical elements. In an example, the shape of a first energy pathway and a shape of the second energy pathway can be selected from the group consisting of: straight; arcuate; simple sinusoidal wave; compound sinusoidal wave; saw-tooth wave; square wave; conic section; helix; spiral; and chain of loops. In an example, the shape of a first energy pathway can change when it changes from the first configuration to the second configuration in one or more of the following ways: longitudinal axis length changes; curvature of longitudinal axis changes; angle formed by two portions of the longitudinal axis changes; frequency length of wavelength of longitudinal axis with a repeating pattern changes; lateral thickness changes; and cross-sectional diameter changes.

In an example, an article of clothing or clothing accessory for capturing body motion can comprise: an article of clothing or clothing accessory worn by a person which is configured to span at least one body joint, wherein this article of clothing or clothing accessory further comprises: a mid joint perimeter portion which is configured around the cross-section of the person's body which includes the center of the joint; a proximal perimeter portion which is configured around a cross-section of the person's body which is proximal relative to the mid-joint perimeter portion, wherein proximal is defined as being closer to the person's heart along the circulatory system; a distal perimeter portion which is configured around a cross-section of the person's body which is distal relative to the mid joint perimeter portion, wherein distal is defined as being further from the person's heart along the circulatory system; a first flexible energy pathway, wherein this energy pathway spans from the proximal perimeter portion to the distal perimeter portion, wherein movement of the joint changes the configuration of this pathway, wherein changes in the configuration of this pathway change a flow of energy through this pathway, and wherein changes in the flow of energy through this pathway can be used alone to estimate movement of the joint with a first level of accuracy; a second flexible energy pathway, wherein this energy pathway spans from the proximal perimeter portion to the distal perimeter portion, wherein movement of the joint changes the configuration of this pathway, wherein changes in the configuration of this pathway change a flow of energy through this pathway, wherein changes in the flow of energy through this pathway can be used alone to estimate movement of the joint with a second level of accuracy, wherein changes in the flows of energy through the first and second flexible energy pathways can be jointly used to estimate movement of the joint with a third level of accuracy, and wherein the third level is greater than either the first level or the second level; at least one energy emitter which emits energy into one or both of the flexible energy pathways; and at least one energy sensor which senses energy from and/or through one or both of the flexible energy pathways, wherein the flow of energy through the one or both of the flexible energy pathways is measured by the at least one energy sensor.

In an example, an article of clothing or clothing accessory for capturing body motion can comprise: an article of clothing or clothing accessory worn by a person which is configured to span at least one body joint, wherein this article of clothing or clothing accessory further comprises: a mid joint perimeter portion which is configured around the cross-section of the person's body which includes the center of the joint; a first proximal perimeter portion which is configured around a cross-section of the person's body which is proximal relative to the mid-joint perimeter portion, wherein proximal is defined as being closer to the person's heart along the circulatory system; a second proximal perimeter portion which is configured around a cross-section of the person's body which is proximal relative to the mid joint perimeter; a first distal perimeter portion which is configured around a cross-section of the person's body which is distal relative to the mid-joint perimeter portion, wherein distal is defined as being further from the person's heart along the circulatory system; a second distal perimeter portion around a cross-section of the person's body which is distal relative to the mid joint perimeter; a first flexible energy pathway, wherein this energy pathway spans from the first proximal perimeter portion to the first distal perimeter portion, wherein movement of the joint changes the configuration of this pathway, wherein changes in the configuration of this pathway change a flow of energy through this pathway, and wherein changes in the flow of energy through this pathway can be used alone to estimate movement of the joint with a first level of accuracy; a second flexible energy pathway, wherein this energy pathway spans from the second proximal perimeter portion to the second distal perimeter portion, wherein movement of the joint changes the configuration of this pathway, wherein changes in the configuration of this pathway change a flow of energy through this pathway, wherein changes in the flow of energy through this pathway can be used alone to estimate movement of the joint with a second level of accuracy, wherein changes in the flows of energy through the first and second flexible energy pathways can be jointly used to estimate movement of the joint with a third level of accuracy, and wherein the third level is greater than either the first level or the second level; at least one energy emitter which emits energy into one or both of the flexible energy pathways; and at least one energy sensor which senses energy from and/or through one or both of the flexible energy pathways, wherein the flow of energy through the one or both of the flexible energy pathways is measured by the at least one energy sensor.

In an example, a wearable device for measuring human joint configuration and/or motion can comprise: a first energy pathway which is configured to span a portion of a person's body which contains a joint, wherein the first energy pathway is moved from a first configuration to a second configuration by movement of the joint, and wherein the first energy pathway has a first energy flow when the pathway is in the first configuration and a second energy flow when the pathway is in the second configuration; a first energy sensor which measures energy flow through or from the first energy pathway; a second energy pathway which is configured to span the portion of the person's body which contains the joint, wherein the second energy pathway is moved from a third configuration to a fourth configuration by movement of the joint, and wherein the second energy pathway has a third energy flow when the pathway is in the third configuration and a fourth energy flow when the pathway is in the fourth configuration; and a second energy sensor which measures energy flow through or from the second energy pathway, wherein data from the first energy sensor and the second energy sensor are analyzed to determine the configuration and/or motion of the joint.

In an example, an article of clothing or wearable accessory can be selected from the group consisting of: ankle band, ankle tube, arm band, arm tube, belt, bra, collar, elbow pad, elbow tube, finger tube, girdle, glove, hip pad, hoodie, knee pad, knee tube, neck band, other wearable top, pair of pants, shirt, shoe, shorts, shoulder pad, shoulder tube, sock, suit, torso band, torso tube, underwear, union suit, waist band, and waist tube. In an example, an article of clothing or clothing accessory can be selected from the group consisting of: a shirt, a pair of shorts, a pair of pants, and a full-body suit.

In an example, energy flows through a first flexible energy pathway with different flow parameters than energy flow through a second flexible energy pathway, wherein these parameters are selected from the group consisting of: rate, level, amplitude, resistance, impedance, filter, frequency, and spectrum. In an example, energy flow through or from the first configuration of the first energy pathway and energy flow through or from the second configuration of the first energy pathway can differ in one or more parameters selected from the group consisting of: total energy; energy flow per time period; energy power; wave amplitude; wave frequency; wave phase; waveform; frequency range; spectral distribution; resistance; voltage; current; impedance; and interval pattern.

In an example, energy pathway can be connected to an article of clothing or wearable accessory by a means selected from the group consisting of: weaving, knitting, and/or sewing; adhesion and/or gluing; hook-and-eye attachment mechanisms; snaps, buckles, straps, or clips; magnetic force; integration with threads, strands, yarns, elastic bands, textile fibers, polymer fibers, metal fibers, and/or nanoscale fibers; and connection by threads, strands, yarns, elastic bands, textile fibers, polymer fibers, metal fibers, and/or nanoscale fibers.

In an example, energy pathways can be part of a mesh which is an array of one or more element shapes selected from the group consisting of: square elements; rectangular elements; diamond elements; rhomboid elements; parallelogram elements; triangular elements; hexagonal elements; circular elements; and elliptical elements. In an example, the shapes of one or more energy pathways can be selected from the group consisting of: straight; arcuate; simple sinusoidal wave; compound sinusoidal wave; saw-tooth wave; square wave; conic section; helix; spiral; and chain of loops.

Having provided the introduction and generic variations above, FIGS. 1 through 7 are now discussed in detail. Variations discussed thus far in this disclosure or in priority-linked disclosures can be applied to the examples shown in FIGS. 1 through 7 where relevant.

FIG. 1 shows an example of a device or system for capturing human motion comprising: an article of clothing 103 worn by a person 101, wherein a portion 104 of the article of clothing has a longitudinal axis which is configured to span a body joint 102, wherein the portion has a first cross-sectional circumference 105 which is proximal relative to the body joint, wherein the portion has a second cross-sectional circumference 106 which is distal relative to the body joint, and wherein proximal means closer to and distal means farther from the person's heart when the person is in Vitruvian Man configuration (shown in FIG. 1); a first inertial motion sensor 107 which is incorporated into the portion at the first cross-sectional circumference; a second inertial motion sensor 108 which is incorporated into the portion at the second cross-sectional circumference; a first stretch (or bend) sensor 109 which is incorporated into the portion and spans the body joint between the first cross-sectional circumference and the second cross-sectional circumference, wherein the first stretch sensor collects data concerning the transmission of electromagnetic energy through the first stretch sensor; a second stretch (or bend) sensor 110 which is incorporated into the portion and spans the body joint between the first cross-sectional circumference and the second cross-sectional circumference, wherein the second stretch sensor collects data concerning the transmission of electromagnetic energy through the second stretch sensor; and a data processor 111 which analyzes data from the first inertial motion sensor, the second inertial motion sensor, the first stretch sensor, and the second stretch sensor to measure a configuration and/or motion of the body joint.

In the example shown in FIG. 1: the article of clothing is a shirt, the portion is a sleeve, the body joint is an elbow, the first cross-sectional circumference is around the person's upper arm, the second cross-sectional circumference is around the person's lower arm, and the data processor is worn by the person. In another example, the data processor can be at a remote location with which the wearable components are in electromagnetic communication.

In an example, a device or system for capturing human motion can comprise: an article of clothing worn by a person, wherein a portion of the article of clothing has a longitudinal axis which is configured to span a body joint, wherein the portion has a first cross-sectional circumference which is proximal relative to the body joint, wherein the portion has a second cross-sectional circumference which is distal relative to the body joint, and wherein proximal means closer to and distal means farther from the person's heart when the person is in Vitruvian Man configuration; a first inertial motion sensor which is incorporated into the portion at the first cross-sectional circumference; a second inertial motion sensor which is incorporated into the portion at the second cross-sectional circumference; a first stretch sensor which is incorporated into the portion and spans the body joint between the first cross-sectional circumference and the second cross-sectional circumference, wherein the first stretch sensor collects data concerning the transmission of electromagnetic energy through the first stretch sensor; a second stretch sensor which is incorporated into the portion and spans the body joint between the first cross-sectional circumference and the second cross-sectional circumference, wherein the second stretch sensor collects data concerning the transmission of electromagnetic energy through the second stretch sensor; a stretch (or bend) sensor which is incorporated into the portion and is in electromagnetic communication with a muscle which moves the body joint and/or with nerves which innervate the muscle, and wherein the stretch (or bend) sensor collects data concerning electromagnetic energy emitted by the muscle and/or the nerves; and a data processor which analyzes data from the first inertial motion sensor, the second inertial motion sensor, the first stretch sensor, the second stretch sensor, and the stretch (or bend) sensor to measure a configuration and/or motion of the body joint. Variations discussed elsewhere in this disclosure or in priority-linked disclosures can be applied to the example in this figure where relevant.

Figure 2:
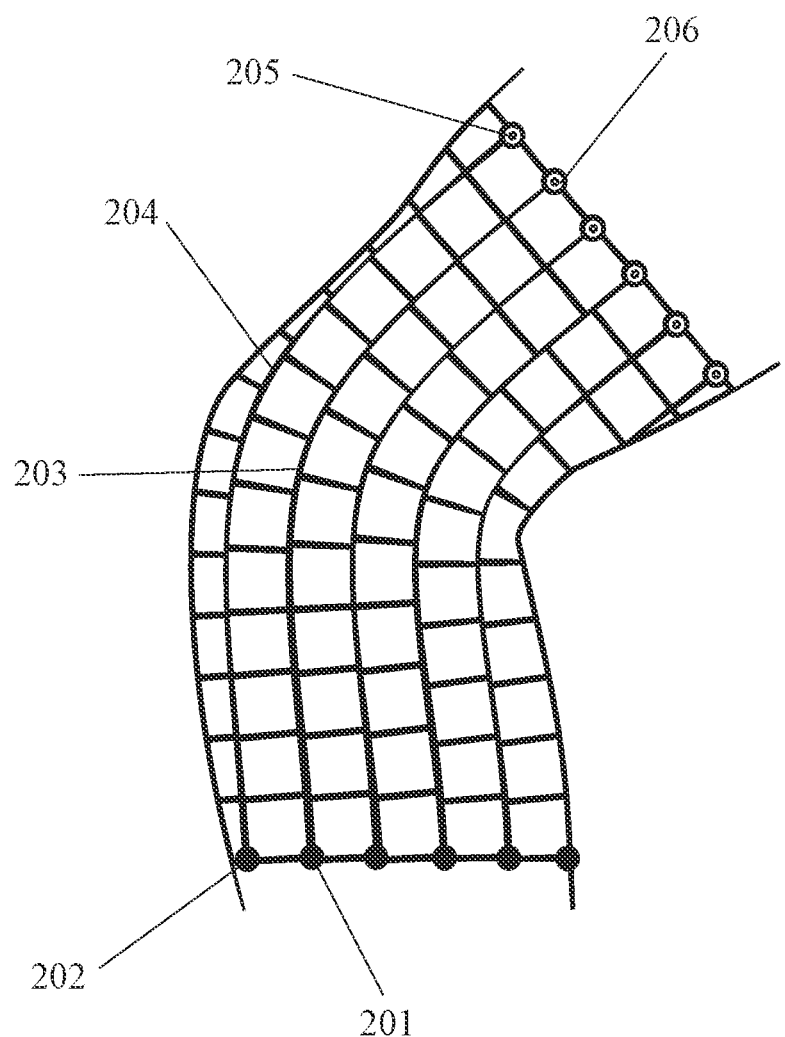
FIG. 2 shows an example with a wearable energy-conducting lattice, mesh, grid, or matrix with longitudinal energy pathways.

FIG. 2 shows an example of how Motion Recognition Clothing™ can be embodied in a wearable device to measure the motion and/or configuration of a body joint comprising—a wearable energy-conducting lattice, mesh, grid, or matrix that is configured to span the surface of a person's body which contains a joint, wherein this lattice, mesh, grid, or matrix further comprises: a plurality of energy pathways including 203 and 204 which are configured to span that portion of the body in a longitudinal manner (from a proximal portion of the joint to a distal portion of the joint, or vice versa); and a plurality of energy sensors including 205 and 206 which measure energy flow through these energy pathways, wherein data from these sensors are analyzed together using multivariate analysis in order to measure the motion and/or configuration of the body joint.

The example in FIG. 2 further comprises energy input components 201 and 202 which direct energy into the lattice, mesh, grid, or matrix. In an example, there can be a single energy input location rather than a plurality of energy input components. In this example, the energy pathways are substantially parallel. In this example, the energy pathways are substantially evenly-spaced around the circumference of the body member containing the joint. In this example, there are gaps and/or elements in the lattice, mesh, grid, or matrix which are substantially the same in size and are shaped like squares, rhombuses, diamonds, trapezoids, or parallelograms.

In an example, the energy sensors and/or energy input components can be modular and/or moveable. In an example, energy sensors and/or energy input components can be snapped or otherwise removably-connected to the lattice, mesh, grid, or matrix at different locations in order to create different energy pathways. In an example, modular and/or moveable energy sensors and/or energy input components can allow the device to be customized to span different joints and/or be customized to a person's specific body contours. In an example, having removably-connected electronic components can also make it easier to wash the device.

In an example, a plurality of wearable energy pathways can form a mesh, grid, lattice, or matrix with square, rectangular, rhomboid, or trapezoid shaped elements. In an example, a plurality of wearable energy pathways can form a mesh, grid, lattice, or matrix with interlocking and/or repeating square, rectangular, rhomboid, or trapezoid shaped elements. In an example, a plurality of wearable energy pathways can form a mesh, grid, lattice, or matrix with diamond-shaped elements. In an example, a plurality of wearable energy pathways can form a mesh, grid, lattice, or matrix with interlocking and/or repeating diamond-shaped elements. In an example, a plurality of wearable energy pathways can form a hexagonal mesh, grid, lattice, or matrix (e.g. a honeycomb mesh or grid).

In an example, a plurality of wearable energy pathways can form a mesh, grid, lattice, or matrix with a chain of loops. In an example, a plurality of wearable energy pathways can form a mesh, grid, lattice, or matrix with a chain of knitted loops. In an example, a plurality of wearable energy pathways can form a mesh, grid, lattice, or matrix with circular or elliptical elements. In an example, a plurality of wearable energy pathways can form a mesh, grid, lattice, or matrix with interlocking and/or repeating circular or elliptical elements. In an example, a plurality of wearable energy pathways can form a mesh, grid, lattice, or matrix with triangular elements. In an example, a plurality of wearable energy pathways can form a mesh, grid, lattice, or matrix with interlocking and/or repeating triangular elements.

In an example, a plurality of wearable energy pathways in a wearable energy-conducting mesh, grid, lattice, or matrix can be straight. In an example, a plurality of wearable energy pathways in a wearable energy-conducting mesh, grid, lattice, or matrix can be sinusoidal. In an example, a plurality of wearable energy pathways in a wearable energy-conducting mesh, grid, lattice, or matrix can have saw-tooth wave or square-wave shapes. In an example, a plurality of wearable energy pathways in a wearable energy-conducting mesh, grid, lattice, or matrix can have conic section shapes, wherein examples of conic sections include circles, ellipses, parabolas, and hyperbolas. In an example, a plurality of wearable energy pathways in a wearable energy-conducting mesh, grid, lattice, or matrix can have helical or spiral shapes.

In an example, a wearable energy-conducting mesh, grid, lattice, or matrix can comprise square elements, rectangular elements, diamond elements, rhomboid elements, parallelogram elements, trapezoidal elements, triangular elements, hexagonal elements, circular elements, or elliptical elements. In an example, a wearable energy-conducting mesh, grid, lattice, or matrix can comprise interlocking and/or repeating square elements, rectangular elements, diamond elements, rhomboid elements, parallelogram elements, trapezoidal elements, triangular elements, hexagonal elements, circular elements, or elliptical elements.

In an example, a wearable energy-conducting mesh, grid, lattice, or matrix can comprise a repeating pattern of quadrilateral (e.g. square, rectangular, trapezoidal, parallelogram, or diamond shaped) elements. In an example, a wearable energy-conducting mesh, grid, lattice, or matrix can comprise a repeating pattern of hexagonal elements (e.g. a honeycomb mesh). In an example, a wearable energy-conducting mesh, grid, lattice, or matrix can comprise a repeating pattern of arcuate elements created by parallel, different-phase sinusoidal curves. In an example, a wearable energy-conducting mesh, grid, lattice, or matrix can comprise a repeating pattern of arcuate elements created by intersecting sinusoidal curves.

In an example, geometric relationships between energy pathways in a wearable energy-conducting mesh, grid, lattice, or matrix can be selected from the group consisting of: substantially parallel; separated by a substantially-constant distance; separated by a substantially-constant number of radial degrees of the cross-sectional perimeter of a body member; separated by a substantially-constant percentage of the cross-sectional perimeter of a body member; forming vectors which intersect in 3D space at a right angle; substantially-parallel as they span a distal portion of a joint and diverging as they span a proximal portion of a joint; substantially-parallel as they span a proximal portion of a joint and diverging as they span a distal portion of a joint; substantially perpendicular; intersecting at an acute angle; forming vectors which intersect in 3D space at an acute angle; substantially diagonal to each other; plaited together; woven together; braided together; combining to form a 3D lattice, mesh, or grid; differing in length; nested; forming a rainbow arc configuration; radial vectors with a common point of convergence; straight vectors with a common convergence point; and arcuate elements with a common convergence point.

In an example, energy pathways in a wearable energy-conducting mesh, grid, lattice, or matrix can differ in the angles at which they span the longitudinal axis of a body member which contains a body joint. In an example, different energy pathways in a wearable energy-conducting mesh, grid, lattice, or matrix can span a body joint at different angles. In an example, having different energy pathways span a body joint at different angles can be especially useful for measuring the motion and/or configuration of ball-and-socket or other complex motion joints. In an example, energy pathways in a wearable energy-conducting mesh, grid, lattice, or matrix can have longitudinal axes which intersect each other in an orthogonal manner. In an example, energy pathways in a wearable energy-conducting mesh, grid, lattice, or matrix can have longitudinal axes which intersect each other at acute angles.

In an example, energy pathways in a wearable energy-conducting mesh, grid, lattice, or matrix can form inter-pathway areas which, when projected from 3D space onto a 2D plane, are squares or rectangles. In an example, one or more aspects of the geometric relationship between energy pathways in a wearable energy-conducting mesh, grid, lattice, or matrix can be selected from the group consisting of: substantially parallel; separated by a substantially-constant distance; intersecting at an acute angle; forming vectors which intersect in 3D space at an acute angle; combining to form a 3D mesh, grid, lattice, or matrix; differing in length; substantially concentric; nested; differing in diameter; knitted together in loops; and tangential.

In an example, one or more aspects of the geometric relationship between energy pathways in a wearable energy-conducting mesh, grid, lattice, or matrix can be selected from the group consisting of: substantially perpendicular; intersecting at a right angle; intersecting at an acute angle; defining square-shaped spaces (when projected onto a 2D plane) as they intersect; defining rhomboid-shaped spaces (when projected onto a 2D plane) as they intersect; defining trapezoid-shaped spaces (when projected onto a 2D plane) as they intersect; plaited together; woven together; braided together; combining to form a 3D mesh, grid, lattice, or matrix; overlapping; and tangential.

In an example, energy pathways in a wearable energy-conducting mesh, grid, lattice, or matrix can have substantially straight configurations when a joint is fully extended. In an example, energy pathways in a wearable energy-conducting mesh, grid, lattice, or matrix can have arcuate shapes, even when a joint is fully extended. In an example, a wearable energy-conducting mesh, grid, lattice, or matrix can have a repeating pattern or waveform selected from the group consisting of: simple sinusoidal wave; composite sinusoidal wave; saw-tooth wave or zigzag; and square wave. In an example, an energy pathway can have a shape which is a conic section. In an example, an energy pathway can have a shape which is a spiral or helix. In an example, an energy pathway can have a shape which is a chain of loops.

In an example, the flows of energy through energy pathways in a wearable energy-conducting mesh, grid, lattice, or matrix can be independent and/or separate. In an example, the flows of energy through energy pathways in a wearable energy-conducting mesh, grid, lattice, or matrix can interact and/or combine with each other. In an example, energy pathways in a wearable energy-conducting mesh, grid, lattice, or matrix can be in electromagnetic communication with each other.

In an example, energy pathways in a wearable energy-conducting mesh, grid, lattice, or matrix can differ by one or more parameters selected from the group consisting of: the angle at which they span the body joint; length; longitudinal curvature or convolution; longitudinal waveform; flexibility; elasticity; electrical resistance or impedance; transparency; and cross-sectional shape. In an example, energy pathways in a wearable energy-conducting mesh, grid, lattice, or matrix can differ in the angles at which they span the body member. In an example, energy pathways in a wearable energy-conducting mesh, grid, lattice, or matrix can differ in length. In an example, energy pathways in a wearable energy-conducting mesh, grid, lattice, or matrix can differ in longitudinal curvature or convolution.

In an example, energy pathways in a wearable energy-conducting mesh, grid, lattice, or matrix can differ in flexibility. In an example, energy pathways in a wearable energy-conducting mesh, grid, lattice, or matrix can differ in elasticity. In an example, energy pathways in a wearable energy-conducting mesh, grid, lattice, or matrix can differ in electrical resistance or impedance. In an example, energy pathways in a wearable energy-conducting mesh, grid, lattice, or matrix can differ in cross-sectional shape.

In an example, energy pathways in a wearable energy-conducting mesh, grid, lattice, or matrix can be woven together in a substantially-perpendicular manner to form a textile. In an example, energy pathways in a wearable energy-conducting mesh, grid, lattice, or matrix can be knitted together. In an example, energy pathways in a wearable energy-conducting mesh, grid, lattice, or matrix can be knitted together in a chain of loops. In an example, energy pathways in a wearable energy-conducting mesh, grid, lattice, or matrix can be plaited, knitted, woven together, or braided together.

In an example, the relationship between energy flow in an energy pathway and the configuration of a body joint spanned by that energy pathway can be nonlinear and/or stochastic. In an example, data from multiple energy pathways can be jointly analyzed using one or more statistical methods selected from the group consisting of: multivariate linear regression or least squares estimation; factor analysis; Fourier Transformation; mean; median; multivariate logit; principal components analysis; spline function; auto-regression; carlavian curve analysis, centroid analysis; correlation; covariance; decision tree analysis; kinematic modeling; Kalman filter; linear discriminant analysis; linear transform; logarithmic function; logit analysis; Markov model; multivariate parametric classifiers; non-linear programming; orthogonal transformation; pattern recognition; random forest analysis; spectroscopic analysis; variance; artificial neural network; Bayesian filter or other Bayesian statistical method; chi-squared; eigenvalue decomposition; logit model; machine learning; power spectral density; power spectrum analysis; probit model; and time-series analysis.

In an example, repeated or cyclical patterns of movement such as walking or running can be identified and analyzed using Fourier analysis. In an example, the speed of repeated movement cycles can influence the functional relationship between the flow of energy through an energy pathway and the angle of a joint. In an example, the speed of repeated cycles can especially influence this functional relationship at the end-points of a cycle wherein joint movement reverses direction. In an example, analyzing and identifying the speed of repeated or cyclical patterns of movement using Fourier transform methods can improve the accuracy of measuring joint motion and configuration.

In an example, data from different energy pathways in a wearable energy-conducting mesh, grid, lattice, or matrix can be given different weights during different portions of the joint range of motion in order to improve accuracy and reduce error in the measurement of the motion and/or configuration of that joint. In an example, data from different energy pathways in a wearable energy-conducting mesh, grid, lattice, or matrix can be given different weights during different directions of joint motion (e.g. flexion vs. extension) in order to improve accuracy and reduce error in the measurement of the motion and/or configuration of that joint. In an example, data from different energy pathways in a wearable energy-conducting mesh, grid, lattice, or matrix can be given different weights during different movement speeds (e.g. fast movement vs. slow movement) of joint motion in order to improve accuracy and reduce error in the measurement of the motion and/or configuration of that joint.

In an example, changes in the flows of electromagnetic energy can be measured by one or more parameters selected from the group consisting of: voltage, resistance, impedance, amperage, current, phase, and wave pattern. In an example, an electromagnetic energy pathway can be comprised of electroconductive fibers, yarns, threads, strands, substrates, layers, or textiles. In an example, an electromagnetic energy sensor can be selected from the group consisting of: voltmeter, impedance sensor, magnetic field sensor, piezoelectric sensor, piezomechanical sensor, potentiometer, resistive bend sensor, variable-resistance sensor, electromyography (EMG) sensor, and Hall-effect sensor.

In an example, electromagnetic energy can be directed into an energy pathway at a first location and electromagnetic energy from the energy pathway can be measured from the energy pathway at a second location. In an example, electromagnetic energy can be directed into a wearable mesh, grid, lattice, or matrix of conductive pathways at a first location and received out from the mesh, grid, lattice, or matrix at a second location. In an example, electromagnetic energy can be directed into a wearable mesh, grid, lattice, or matrix of conductive pathways at a first vertex (or juncture of energy-conducting pathways) and received out from the mesh, grid, lattice, or matrix at a second vertex (or juncture of energy-conducting pathways). In an example, electromagnetic energy can be directed into a wearable mesh, grid, lattice, or matrix of conductive pathways at a first set of multiple location, vertexes, and/or pathway junctures and received out from the mesh, grid, lattice, or matrix at a second set of multiple location, vertexes, and/or pathway junctures In an example, electromagnetic energy can be transmitted into an energy pathway at a first location and electromagnetic energy from the energy pathway can be measured from the energy pathway at a second location. In an example, electromagnetic energy can be transmitted into a wearable mesh, grid, lattice, or matrix of conductive pathways at a first location and measured from the mesh, grid, lattice, or matrix at a second location. In an example, electromagnetic energy can be transmitted into a wearable mesh, grid, lattice, or matrix of conductive pathways at a first vertex (or juncture of energy-conducting pathways) and measured from the mesh, grid, lattice, or matrix at a second vertex (or juncture of energy-conducting pathways). In an example, electromagnetic energy can be transmitted into a wearable mesh, grid, lattice, or matrix of conductive pathways at a first set of multiple location, vertexes, and/or pathway junctures and measured from the mesh, grid, lattice, or matrix at a second set of multiple location, vertexes, and/or pathway junctures In an example, wearable energy pathways in a wearable mesh, grid, lattice, or matrix can comprise non-conductive or less-conductive fibers, traces, yarns, strands, or textiles which are coated, impregnated, or otherwise integrated with conductive material or particles. In an example, a non-conductive or less-conductive fiber, trace, yarn, strand, or textile can be selected from the group consisting of: acetate, acrylic, cotton, denim, elastane, Kevlar, latex, linen, Lycra, neoprene, nylon, nylon, polyester, wool, silicon rubber, silk, spandex, Danconn or rayon. In an example, conductive material or particles used for coating or impregnation can be selected from the group consisting of: aluminum or aluminum alloy; carbon nanotubes, graphene, or other carbon-based material; magnesium; ceramic particles; copper or copper alloy; gold; nickel; polyaniline; silver; and steel.

In an example, a wearable energy-conducting mesh, grid, lattice, or matrix can comprise one or more of the following: array of electroconductive members woven using a plain weave, rib weave, basket weave, twill weave, satin weave, leno weave, mock leno weave, or conan weave; array of fiber optic members woven using a plain weave, rib weave, basket weave, twill weave, satin weave, leno weave, mock leno weave; array of light-emitting fibers, threads, or yarns; array of sound-conducting members woven using a plain weave, rib weave, basket weave, twill weave, satin weave, leno weave, mock leno weave; array or mesh of electroconductive fibers; bendable fibers, threads, or yarns; bendable layer, trace, or substrate; elastic fibers, threads, or yarns; elastic layer, trace, or substrate; electroconductive fibers, threads, or yarns; electronically-functional bandage; electronically-functional tattoo; integrated array of electroconductive members; integrated array of fiber optic members; integrated array of sound-conducting members; interlaced electricity-conducting fibers, threads, or yarns; interlaced light-conducting fibers, threads, or yarns; interlaced sound-conducting fibers, threads, or yarns; light-emitting fibers, threads, or yarns; nonconductive fibers, threads, or yarns;

nonconductive layer, substrate, or material; plaited fibers, threads, or yarns; sinusoidal fibers, threads, or yarns; stretchable fibers, threads, or yarns; stretchable layer, trace, or substrate; textile-based light display matrix; variable-resistance electroconductive fiber, thread, or yarn; variable-translucence fiber, thread, or yarn; water-resistant fibers, threads, or yarns; a layer or coating of metallic nanoparticles; a graphene layer; and water-resistant layer, trace, or substrate.

In an example, a wearable energy-conducting mesh, grid, lattice, or matrix can be incorporated into an article of clothing which is, in turn, worn over a body member containing a body joint. Changes in energy conducted through these pathways can be used to estimate joint motion and/or configuration. In an example, an array of energy pathways can be directly attached to a body member containing a body joint. In an example, energy pathways can be incorporated into an article of clothing or directly attached to a body member using one or more means selected from the group consisting of: adhesion, armband, article of clothing, bangle, belt, bracelet, buckle, button, clasp, clip, elastic band, elastic garment, eyewear, fabric layer, garment channel, garment pocket, gluing, hook, hook-and-eye attachment mechanism, incorporation into a bandage, incorporation into a tattoo, knitting, loop, magnetism, melting, metal fibers, nanoscale fibers, necklace, pin, polymer fibers, sewing, skin-adhesive patch, smart watch, snap, strands, strap, tape, textile channel, textile fibers, thermal bonding, tubular garment, waist band, weaving, wrist band, yarn, and zipper.

In an example, a wearable energy-conducting mesh, grid, lattice, or matrix can be incorporated into an article of clothing or clothing accessory selected from the group consisting of: an upper body garment such as a shirt, t-shirt, blouse, jacket, hoodie, sweatshirt, undershirt, brassier, girdle, blouse, or glove; a lower body garment such as a pair of pants, sweatpants, trousers, slacks, leggings, tights, underpants, pantyhose, shorts, or sock; a full-body garment such as a union suit, jump suit, pair of overalls, or dress; a clothing accessory such as shoe, boot, insole, hat, cap, headband, armband, strap, torso band, tubular accessory, wristband, other band, knee or elbow brace, back brace, knee or elbow pad, belt, bandage, electronic tattoo, or wearable patch.

In various examples, a wearable energy-conducting mesh, grid, lattice, or matrix can measure one or more joint configurations and/or motions selected from the group consisting of: eversion, extension, flexion, and/or inversion of the ankle; abduction, extension, flexion, lateral bending, and/or rotation of the spine; eversion, extension, flexion, and/or inversion of the elbow; extension and/or flexion of the finger or thumb; pronation, rotation, and/or supination of the forearm; abduction, adduction, extension, flexion, and/or rotation of the hip; extension and/or flexion of the jaw; abduction, adduction, extension, and/or flexion of the knee; eversion and/or inversion of the mid-tarsal; abduction, extension, flexion, and/or rotation of the neck; abduction, adduction, extension, flexion, and/or rotation of the shoulder; extension and/or flexion of the toe; and abduction, extension, flexion, and/or ulnar deviation or radial deviation of the wrist.

In an example, a wearable energy-conducting mesh, grid, lattice, or matrix can span the surface of the portion of the body containing one or more body joints selected from the group consisting of: ankle, elbow, finger, forearm, hip, jaw, knee, mid-tarsal, neck, shoulder, spine, thumb, toe, and wrist. In an example, a wearable energy-conducting mesh, grid, lattice, or matrix can span the surface of a body member containing the finger and thumb. In an example, a wearable energy-conducting mesh, grid, lattice, or matrix can span the surface of a body member containing the finger, forearm, thumb and wrist. In an example, a wearable energy-conducting mesh, grid, lattice, or matrix can span the surface of a body member containing the elbow, forearm and wrist.

In an example, a wearable energy-conducting mesh, grid, lattice, or matrix can span the surface of a body member containing an elbow. In an example, a wearable energy-conducting mesh, grid, lattice, or matrix can span the surface of the body containing an elbow, forearm, shoulder and spine. In an example, a wearable energy-conducting mesh, grid, lattice, or matrix can span the surface of a body member containing a hip and knee. In an example, a wearable energy-conducting mesh, grid, lattice, or matrix can span the surface of a body member containing the spine. In an example, a wearable energy-conducting mesh, grid, lattice, or matrix can span the surface of a body member containing an ankle, mid-tarsal and toe. In an example, a wearable energy-conducting mesh, grid, lattice, or matrix can span the surface of the portion of the body containing the neck, shoulder and spine.

In an example, an article of clothing or clothing accessory can be selected from the group consisting of: a shirt, a pair of shorts, a pair of pants, and a full-body suit. In an example, an article of clothing or wearable accessory can be selected from the group consisting of: ankle band, ankle tube, arm band, arm tube, belt, bra, collar, elbow pad, elbow tube, finger tube, girdle, glove, hip pad, hoodie, knee pad, knee tube, neck band, other wearable top, pair of pants, shirt, shoe, shorts, shoulder pad, shoulder tube, sock, suit, torso band, torso tube, underwear, union suit, waist band, and waist tube. In an example, energy pathway can be connected to an article of clothing or wearable accessory by a means selected from the group consisting of: weaving, knitting, and/or sewing; adhesion and/or gluing; hook-and-eye attachment mechanisms; snaps, buckles, straps, or clips; magnetic force; integration with threads, strands, yarns, elastic bands, textile fibers, polymer fibers, metal fibers, and/or nanoscale fibers; and connection by threads, strands, yarns, elastic bands, textile fibers, polymer fibers, metal fibers, and/or nanoscale fibers.

In an example, energy flow through or from different energy pathways in a wearable energy-conducting mesh, grid, lattice, or matrix can differ in one or more parameters selected from the group consisting of: total energy; energy flow per time period; energy power; wave amplitude; wave frequency; wave phase; waveform; frequency range; spectral distribution; resistance; voltage; current; impedance; and interval pattern.

In an example, Motion Recognition Clothing™ can also include a data control unit which further comprises one or more components selected from the group consisting of: a data processing component, a data communication component, a power source, a human-to-computer user interface, a computer-to-human interface, and a digital memory. In an example, a data control unit can be temporarily detached so that the remaining wearable portion of the invention can be washed. In an example, a data processing component can perform one or more functions selected from the group consisting of: amplify sensor signals, analyze data, analyze sensor information, convert analog signals to digital signals, determine a functional relationship between signal variation and joint angle variation, estimate joint angle, filter signals, model joint configuration, record data, run software applications, run software programs, and store data in memory.

In an example, a data communication component can perform one or more functions selected from the group consisting of: transmit and receive data via Bluetooth, WiFi, Zigbee, or other wireless communication modality; transmit and receive data to and from a mobile electronic device such as a cellular phone, mobile phone, smart phone, electronic tablet; transmit and receive data to and from a separate wearable device such as a smart watch or electronically-functional eyewear; transmit and receive data to and from the internet; send and receive phone calls and electronic messages; transmit and receive data to and from a home appliance and/or home control system; and transmit and receive data to and from an implantable medical device.

In an example, Motion Recognition Clothing™ can further comprise one or more motion-related sensors selected from the group consisting of: dual-axial accelerometer, tri-axial accelerometer, other multi-axial accelerometer, gyroscope, inclinometer or tilt sensor, goniometer, GPS or other location sensor, other inertial or motion sensor, goniometer, and kinematic sensor. In an example, Motion Recognition Clothing™ can further comprise one or more electromagnetic energy sensors selected from the group consisting of: electroencephalography (EEG) sensor, peripheral neurosensor, electromyography (EMG) sensor, Hall-effect sensor, electromagnetic field sensor, electrocardiogram (ECG) sensor, cardiac monitor, EOG sensor, galvanic skin response (GSR) sensor, impedance sensor, compass, magnometer, magnetic sensor, potentiometer, variable-resistance sensor, resistive bend sensor, piezoelectric sensor, piezomechanical sensor, piezoresistive sensor, and other electromagnetic sensor. Variations discussed elsewhere in this disclosure or in priority-linked disclosures can be applied to the example in this figure where relevant.

Figure 3:
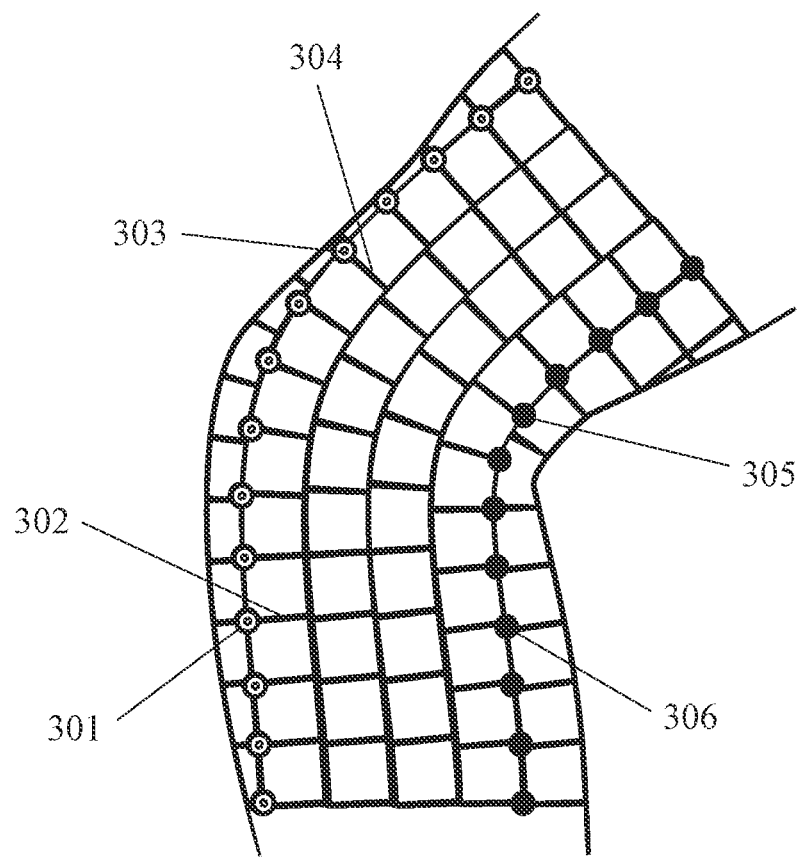
FIG. 3 shows an example with a wearable energy-conducting lattice, mesh, grid, or matrix with circumferential energy pathways.

FIG. 3 shows an example of how Motion Recognition Clothing™ can be embodied in a wearable device to measure the motion and/or configuration of a body joint comprising—a wearable energy-conducting lattice, mesh, grid, or matrix that is configured to span the surface of a person's body which contains a joint, wherein this lattice, mesh, grid, or matrix further comprises: a plurality of energy pathways including 302 and 304 which are configured to span that portion of the body in a (partial) circumferential manner; and a plurality of energy sensors including 301 and 303 which measure energy flow through these energy pathways, wherein data from these sensors are analyzed together using multivariate analysis in order to measure the motion and/or configuration of the body joint.

The example in FIG. 3 further comprises energy input components 305 and 306 which direct energy into the lattice, mesh, grid, or matrix. In an example, there can be a single energy input location rather than a plurality of energy input components. In this example, the energy pathways follow vectors which converge at a point outside the volume of the device. In this example, the energy pathways are substantially evenly-spaced along the longitudinal axis of the body member containing the joint. In this example, there are gaps and/or elements in the lattice, mesh, grid, or matrix which are substantially the same in size and are shaped like squares, rhombuses, diamonds, trapezoids, or parallelograms.

In an example, the energy sensors and/or energy input components can be modular and/or moveable. In an example, energy sensors and/or energy input components can be snapped or otherwise removably-connected to the lattice, mesh, grid, or matrix at different locations in order to create different energy pathways. In an example, modular and/or moveable energy sensors and/or energy input components can allow the device to be customized to span different joints and/or be customized to a person's specific body contours. In an example, having removably-connected electronic components can also make it easier to wash the device.

In an example, a plurality of wearable energy pathways can form a mesh, grid, lattice, or matrix with square, rectangular, rhomboid, or trapezoid shaped elements. In an example, a plurality of wearable energy pathways can form a mesh, grid, lattice, or matrix with interlocking and/or repeating square, rectangular, rhomboid, or trapezoid shaped elements. In an example, a plurality of wearable energy pathways can form a mesh, grid, lattice, or matrix with diamond-shaped elements. In an example, a plurality of wearable energy pathways can form a mesh, grid, lattice, or matrix with interlocking and/or repeating diamond-shaped elements. In an example, a plurality of wearable energy pathways can form a hexagonal mesh, grid, lattice, or matrix (e.g. a honeycomb mesh or grid).

In an example, a plurality of wearable energy pathways can form a mesh, grid, lattice, or matrix with a chain of loops. In an example, a plurality of wearable energy pathways can form a mesh, grid, lattice, or matrix with a chain of knitted loops. In an example, a plurality of wearable energy pathways can form a mesh, grid, lattice, or matrix with circular or elliptical elements. In an example, a plurality of wearable energy pathways can form a mesh, grid, lattice, or matrix with interlocking and/or repeating circular or elliptical elements. In an example, a plurality of wearable energy pathways can form a mesh, grid, lattice, or matrix with triangular elements. In an example, a plurality of wearable energy pathways can form a mesh, grid, lattice, or matrix with interlocking and/or repeating triangular elements.

In an example, a plurality of wearable energy pathways in a wearable energy-conducting mesh, grid, lattice, or matrix can be straight. In an example, a plurality of wearable energy pathways in a wearable energy-conducting mesh, grid, lattice, or matrix can be sinusoidal. In an example, a plurality of wearable energy pathways in a wearable energy-conducting mesh, grid, lattice, or matrix can have saw-tooth wave or square-wave shapes. In an example, a plurality of wearable energy pathways in a wearable energy-conducting mesh, grid, lattice, or matrix can have conic section shapes, wherein examples of conic sections include circles, ellipses, parabolas, and hyperbolas. In an example, a plurality of wearable energy pathways in a wearable energy-conducting mesh, grid, lattice, or matrix can have helical or spiral shapes.

In an example, a wearable energy-conducting mesh, grid, lattice, or matrix can comprise square elements, rectangular elements, diamond elements, rhomboid elements, parallelogram elements, trapezoidal elements, triangular elements, hexagonal elements, circular elements, or elliptical elements. In an example, a wearable energy-conducting mesh, grid, lattice, or matrix can comprise interlocking and/or repeating square elements, rectangular elements, diamond elements, rhomboid elements, parallelogram elements, trapezoidal elements, triangular elements, hexagonal elements, circular elements, or elliptical elements.

In an example, a wearable energy-conducting mesh, grid, lattice, or matrix can comprise a repeating pattern of quadrilateral (e.g. square, rectangular, trapezoidal, parallelogram, or diamond shaped) elements. In an example, a wearable energy-conducting mesh, grid, lattice, or matrix can comprise a repeating pattern of hexagonal elements (e.g. a honeycomb mesh). In an example, a wearable energy-conducting mesh, grid, lattice, or matrix can comprise a repeating pattern of arcuate elements created by parallel, different-phase sinusoidal curves. In an example, a wearable energy-conducting mesh, grid, lattice, or matrix can comprise a repeating pattern of arcuate elements created by intersecting sinusoidal curves.

In an example, geometric relationships between energy pathways in a wearable energy-conducting mesh, grid, lattice, or matrix can be selected from the group consisting of: substantially parallel; separated by a substantially-constant distance; separated by a substantially-constant number of radial degrees of the cross-sectional perimeter of a body member; separated by a substantially-constant percentage of the cross-sectional perimeter of a body member; forming vectors which intersect in 3D space at a right angle; substantially-parallel as they span a distal portion of a joint and diverging as they span a proximal portion of a joint; substantially-parallel as they span a proximal portion of a joint and diverging as they span a distal portion of a joint; substantially perpendicular; intersecting at an acute angle; forming vectors which intersect in 3D space at an acute angle; substantially diagonal to each other; plaited together; woven together; braided together; combining to form a 3D lattice, mesh, or grid; differing in length; nested; forming a rainbow arc configuration; radial vectors with a common point of convergence; straight vectors with a common convergence point; and arcuate elements with a common convergence point.

In an example, energy pathways in a wearable energy-conducting mesh, grid, lattice, or matrix can differ in the angles at which they span the longitudinal axis of a body member which contains a body joint. In an example, different energy pathways in a wearable energy-conducting mesh, grid, lattice, or matrix can span a body joint at different angles. In an example, having different energy pathways span a body joint at different angles can be especially useful for measuring the motion and/or configuration of ball-and-socket or other complex motion joints. In an example, energy pathways in a wearable energy-conducting mesh, grid, lattice, or matrix can have longitudinal axes which intersect each other in an orthogonal manner. In an example, energy pathways in a wearable energy-conducting mesh, grid, lattice, or matrix can have longitudinal axes which intersect each other at acute angles.

In an example, energy pathways in a wearable energy-conducting mesh, grid, lattice, or matrix can form inter-pathway areas which, when projected from 3D space onto a 2D plane, are squares or rectangles. In an example, one or more aspects of the geometric relationship between energy pathways in a wearable energy-conducting mesh, grid, lattice, or matrix can be selected from the group consisting of: substantially parallel; separated by a substantially-constant distance; intersecting at an acute angle; forming vectors which intersect in 3D space at an acute angle; combining to form a 3D mesh, grid, lattice, or matrix; differing in length; substantially concentric; nested; differing in diameter; knitted together in loops; and tangential.

In an example, one or more aspects of the geometric relationship between energy pathways in a wearable energy-conducting mesh, grid, lattice, or matrix can be selected from the group consisting of: substantially perpendicular; intersecting at a right angle; intersecting at an acute angle; defining square-shaped spaces (when projected onto a 2D plane) as they intersect; defining rhomboid-shaped spaces (when projected onto a 2D plane) as they intersect; defining trapezoid-shaped spaces (when projected onto a 2D plane) as they intersect; plaited together; woven together; braided together; combining to form a 3D mesh, grid, lattice, or matrix; overlapping; and tangential.

In an example, energy pathways in a wearable energy-conducting mesh, grid, lattice, or matrix can have substantially straight configurations when a joint is fully extended. In an example, energy pathways in a wearable energy-conducting mesh, grid, lattice, or matrix can have arcuate shapes, even when a joint is fully extended. In an example, a wearable energy-conducting mesh, grid, lattice, or matrix can have a repeating pattern or waveform selected from the group consisting of: simple sinusoidal wave; composite sinusoidal wave; saw-tooth wave or zigzag; and square wave. In an example, an energy pathway can have a shape which is a conic section. In an example, an energy pathway can have a shape which is a spiral or helix. In an example, an energy pathway can have a shape which is a chain of loops.

In an example, the flows of energy through energy pathways in a wearable energy-conducting mesh, grid, lattice, or matrix can be independent and/or separate. In an example, the flows of energy through energy pathways in a wearable energy-conducting mesh, grid, lattice, or matrix can interact and/or combine with each other. In an example, energy pathways in a wearable energy-conducting mesh, grid, lattice, or matrix can be in electromagnetic communication with each other.

In an example, energy pathways in a wearable energy-conducting mesh, grid, lattice, or matrix can differ by one or more parameters selected from the group consisting of: the angle at which they span the body joint; length; longitudinal curvature or convolution; longitudinal waveform; flexibility; elasticity; electrical resistance or impedance; transparency; and cross-sectional shape. In an example, energy pathways in a wearable energy-conducting mesh, grid, lattice, or matrix can differ in the angles at which they span the body member. In an example, energy pathways in a wearable energy-conducting mesh, grid, lattice, or matrix can differ in length. In an example, energy pathways in a wearable energy-conducting mesh, grid, lattice, or matrix can differ in longitudinal curvature or convolution.

In an example, energy pathways in a wearable energy-conducting mesh, grid, lattice, or matrix can differ in flexibility. In an example, energy pathways in a wearable energy-conducting mesh, grid, lattice, or matrix can differ in elasticity. In an example, energy pathways in a wearable energy-conducting mesh, grid, lattice, or matrix can differ in electrical resistance or impedance. In an example, energy pathways in a wearable energy-conducting mesh, grid, lattice, or matrix can differ in cross-sectional shape.

In an example, energy pathways in a wearable energy-conducting mesh, grid, lattice, or matrix can be woven together in a substantially-perpendicular manner to form a textile. In an example, energy pathways in a wearable energy-conducting mesh, grid, lattice, or matrix can be knitted together. In an example, energy pathways in a wearable energy-conducting mesh, grid, lattice, or matrix can be knitted together in a chain of loops. In an example, energy pathways in a wearable energy-conducting mesh, grid, lattice, or matrix can be plaited, knitted, woven together, or braided together.

In an example, the relationship between energy flow in an energy pathway and the configuration of a body joint spanned by that energy pathway can be nonlinear and/or stochastic. In an example, data from multiple energy pathways can be jointly analyzed using one or more statistical methods selected from the group consisting of: multivariate linear regression or least squares estimation; factor analysis;

Fourier Transformation; mean; median; multivariate logit; principal components analysis; spline function; auto-regression; carlavian curve analysis, centroid analysis; correlation; covariance; decision tree analysis; kinematic modeling; Kalman filter; linear discriminant analysis; linear transform; logarithmic function; logit analysis; Markov model; multivariate parametric classifiers; non-linear programming; orthogonal transformation; pattern recognition; random forest analysis; spectroscopic analysis; variance; artificial neural network; Bayesian filter or other Bayesian statistical method; chi-squared; eigenvalue decomposition; logit model; machine learning; power spectral density; power spectrum analysis; probit model; and time-series analysis.

In an example, repeated or cyclical patterns of movement such as walking or running can be identified and analyzed using Fourier analysis. In an example, the speed of repeated movement cycles can influence the functional relationship between the flow of energy through an energy pathway and the angle of a joint. In an example, the speed of repeated cycles can especially influence this functional relationship at the end-points of a cycle wherein joint movement reverses direction. In an example, analyzing and identifying the speed of repeated or cyclical patterns of movement using Fourier transform methods can improve the accuracy of measuring joint motion and configuration.

In an example, data from different energy pathways in a wearable energy-conducting mesh, grid, lattice, or matrix can be given different weights during different portions of the joint range of motion in order to improve accuracy and reduce error in the measurement of the motion and/or configuration of that joint. In an example, data from different energy pathways in a wearable energy-conducting mesh, grid, lattice, or matrix can be given different weights during different directions of joint motion (e.g. flexion vs. extension) in order to improve accuracy and reduce error in the measurement of the motion and/or configuration of that joint. In an example, data from different energy pathways in a wearable energy-conducting mesh, grid, lattice, or matrix can be given different weights during different movement speeds (e.g. fast movement vs. slow movement) of joint motion in order to improve accuracy and reduce error in the measurement of the motion and/or configuration of that joint.

In an example, changes in the flows of electromagnetic energy can be measured by one or more parameters selected from the group consisting of: voltage, resistance, impedance, amperage, current, phase, and wave pattern. In an example, an electromagnetic energy pathway can be comprised of electroconductive fibers, yarns, threads, strands, substrates, layers, or textiles. In an example, an electromagnetic energy sensor can be selected from the group consisting of: voltmeter, impedance sensor, magnetic field sensor, piezoelectric sensor, piezomechanical sensor, potentiometer, resistive bend sensor, variable-resistance sensor, electromyography (EMG) sensor, and Hall-effect sensor.

In an example, electromagnetic energy can be directed into an energy pathway at a first location and electromagnetic energy from the energy pathway can be measured from the energy pathway at a second location. In an example, electromagnetic energy can be directed into a wearable mesh, grid, lattice, or matrix of conductive pathways at a first location and received out from the mesh, grid, lattice, or matrix at a second location. In an example, electromagnetic energy can be directed into a wearable mesh, grid, lattice, or matrix of conductive pathways at a first vertex (or juncture of energy-conducting pathways) and received out from the mesh, grid, lattice, or matrix at a second vertex (or juncture of energy-conducting pathways). In an example, electromagnetic energy can be directed into a wearable mesh, grid, lattice, or matrix of conductive pathways at a first set of multiple location, vertexes, and/or pathway junctures and received out from the mesh, grid, lattice, or matrix at a second set of multiple location, vertexes, and/or pathway junctures In an example, electromagnetic energy can be transmitted into an energy pathway at a first location and electromagnetic energy from the energy pathway can be measured from the energy pathway at a second location. In an example, electromagnetic energy can be transmitted into a wearable mesh, grid, lattice, or matrix of conductive pathways at a first location and measured from the mesh, grid, lattice, or matrix at a second location. In an example, electromagnetic energy can be transmitted into a wearable mesh, grid, lattice, or matrix of conductive pathways at a first vertex (or juncture of energy-conducting pathways) and measured from the mesh, grid, lattice, or matrix at a second vertex (or juncture of energy-conducting pathways). In an example, electromagnetic energy can be transmitted into a wearable mesh, grid, lattice, or matrix of conductive pathways at a first set of multiple location, vertexes, and/or pathway junctures and measured from the mesh, grid, lattice, or matrix at a second set of multiple location, vertexes, and/or pathway junctures In an example, wearable energy pathways in a wearable mesh, grid, lattice, or matrix can comprise non-conductive or less-conductive fibers, traces, yarns, strands, or textiles which are coated, impregnated, or otherwise integrated with conductive material or particles. In an example, a non-conductive or less-conductive fiber, trace, yarn, strand, or textile can be selected from the group consisting of: acetate, acrylic, cotton, denim, elastane, Kevlar, latex, linen, Lycra, neoprene, nylon, nylon, polyester, wool, silicon rubber, silk, spandex, Danconn or rayon. In an example, conductive material or particles used for coating or impregnation can be selected from the group consisting of: aluminum or aluminum alloy; carbon nanotubes, graphene, or other carbon-based material; magnesium; ceramic particles; copper or copper alloy; gold; nickel; polyaniline; silver; and steel.

In an example, a wearable energy-conducting mesh, grid, lattice, or matrix can comprise one or more of the following: array of electroconductive members woven using a plain weave, rib weave, basket weave, twill weave, satin weave, leno weave, mock leno weave, or conan weave; array of fiber optic members woven using a plain weave, rib weave, basket weave, twill weave, satin weave, leno weave, mock leno weave; array of light-emitting fibers, threads, or yarns; array of sound-conducting members woven using a plain weave, rib weave, basket weave, twill weave, satin weave, leno weave, mock leno weave; array or mesh of electroconductive fibers; bendable fibers, threads, or yarns; bendable layer, trace, or substrate; elastic fibers, threads, or yarns; elastic layer, trace, or substrate; electroconductive fibers, threads, or yarns; electronically-functional bandage; electronically-functional tattoo; integrated array of electroconductive members; integrated array of fiber optic members; integrated array of sound-conducting members; interlaced electricity-conducting fibers, threads, or yarns; interlaced light-conducting fibers, threads, or yarns; interlaced sound-conducting fibers, threads, or yarns; light-emitting fibers, threads, or yarns; nonconductive fibers, threads, or yarns; nonconductive layer, substrate, or material; plaited fibers, threads, or yarns; sinusoidal fibers, threads, or yarns; stretchable fibers, threads, or yarns; stretchable layer, trace, or substrate; textile-based light display matrix; variable-resistance electroconductive fiber, thread, or yarn; variable-translucence fiber, thread, or yarn; water-resistant fibers, threads, or yarns; a layer or coating of metallic nanoparticles; a graphene layer; and water-resistant layer, trace, or substrate.

In an example, a wearable energy-conducting mesh, grid, lattice, or matrix can be incorporated into an article of clothing which is, in turn, worn over a body member containing a body joint. Changes in energy conducted through these pathways can be used to estimate joint motion and/or configuration. In an example, an array of energy pathways can be directly attached to a body member containing a body joint. In an example, energy pathways can be incorporated into an article of clothing or directly attached to a body member using one or more means selected from the group consisting of: adhesion, armband, article of clothing, bangle, belt, bracelet, buckle, button, clasp, clip, elastic band, elastic garment, eyewear, fabric layer, garment channel, garment pocket, gluing, hook, hook-and-eye attachment mechanism, incorporation into a bandage, incorporation into a tattoo, knitting, loop, magnetism, melting, metal fibers, nanoscale fibers, necklace, pin, polymer fibers, sewing, skin-adhesive patch, smart watch, snap, strands, strap, tape, textile channel, textile fibers, thermal bonding, tubular garment, waist band, weaving, wrist band, yarn, and zipper.

In an example, a wearable energy-conducting mesh, grid, lattice, or matrix can be incorporated into an article of clothing or clothing accessory selected from the group consisting of: an upper body garment such as a shirt, t-shirt, blouse, jacket, hoodie, sweatshirt, undershirt, brassier, girdle, blouse, or glove; a lower body garment such as a pair of pants, sweatpants, trousers, slacks, leggings, tights, underpants, pantyhose, shorts, or sock; a full-body garment such as a union suit, jump suit, pair of overalls, or dress; a clothing accessory such as shoe, boot, insole, hat, cap, headband, armband, strap, torso band, tubular accessory, wristband, other band, knee or elbow brace, back brace, knee or elbow pad, belt, bandage, electronic tattoo, or wearable patch.

In various examples, a wearable energy-conducting mesh, grid, lattice, or matrix can measure one or more joint configurations and/or motions selected from the group consisting of: eversion, extension, flexion, and/or inversion of the ankle; abduction, extension, flexion, lateral bending, and/or rotation of the spine; eversion, extension, flexion, and/or inversion of the elbow; extension and/or flexion of the finger or thumb; pronation, rotation, and/or supination of the forearm; abduction, adduction, extension, flexion, and/or rotation of the hip; extension and/or flexion of the jaw; abduction, adduction, extension, and/or flexion of the knee; eversion and/or inversion of the mid-tarsal; abduction, extension, flexion, and/or rotation of the neck; abduction, adduction, extension, flexion, and/or rotation of the shoulder; extension and/or flexion of the toe; and abduction, extension, flexion, and/or ulnar deviation or radial deviation of the wrist.

In an example, a wearable energy-conducting mesh, grid, lattice, or matrix can span the surface of the portion of the body containing one or more body joints selected from the group consisting of: ankle, elbow, finger, forearm, hip, jaw, knee, mid-tarsal, neck, shoulder, spine, thumb, toe, and wrist. In an example, a wearable energy-conducting mesh, grid, lattice, or matrix can span the surface of a body member containing the finger and thumb. In an example, a wearable energy-conducting mesh, grid, lattice, or matrix can span the surface of a body member containing the finger, forearm, thumb and wrist. In an example, a wearable energy-conducting mesh, grid, lattice, or matrix can span the surface of a body member containing the elbow, forearm and wrist.

In an example, a wearable energy-conducting mesh, grid, lattice, or matrix can span the surface of a body member containing an elbow. In an example, a wearable energy-conducting mesh, grid, lattice, or matrix can span the surface of the body containing an elbow, forearm, shoulder and spine. In an example, a wearable energy-conducting mesh, grid, lattice, or matrix can span the surface of a body member containing a hip and knee. In an example, a wearable energy-conducting mesh, grid, lattice, or matrix can span the surface of a body member containing the spine. In an example, a wearable energy-conducting mesh, grid, lattice, or matrix can span the surface of a body member containing an ankle, mid-tarsal and toe. In an example, a wearable energy-conducting mesh, grid, lattice, or matrix can span the surface of the portion of the body containing the neck, shoulder and spine.

In an example, an article of clothing or clothing accessory can be selected from the group consisting of: a shirt, a pair of shorts, a pair of pants, and a full-body suit. In an example, an article of clothing or wearable accessory can be selected from the group consisting of: ankle band, ankle tube, arm band, arm tube, belt, bra, collar, elbow pad, elbow tube, finger tube, girdle, glove, hip pad, hoodie, knee pad, knee tube, neck band, other wearable top, pair of pants, shirt, shoe, shorts, shoulder pad, shoulder tube, sock, suit, torso band, torso tube, underwear, union suit, waist band, and waist tube. In an example, energy pathway can be connected to an article of clothing or wearable accessory by a means selected from the group consisting of: weaving, knitting, and/or sewing; adhesion and/or gluing; hook-and-eye attachment mechanisms; snaps, buckles, straps, or clips; magnetic force; integration with threads, strands, yarns, elastic bands, textile fibers, polymer fibers, metal fibers, and/or nanoscale fibers; and connection by threads, strands, yarns, elastic bands, textile fibers, polymer fibers, metal fibers, and/or nanoscale fibers.

In an example, energy flow through or from different energy pathways in a wearable energy-conducting mesh, grid, lattice, or matrix can differ in one or more parameters selected from the group consisting of: total energy; energy flow per time period; energy power; wave amplitude; wave frequency; wave phase; waveform; frequency range; spectral distribution; resistance; voltage; current; impedance; and interval pattern.

In an example, Motion Recognition Clothing™ can also include a data control unit which further comprises one or more components selected from the group consisting of: a data processing component, a data communication component, a power source, a human-to-computer user interface, a computer-to-human interface, and a digital memory. In an example, a data control unit can be temporarily detached so that the remaining wearable portion of the invention can be washed. In an example, a data processing component can perform one or more functions selected from the group consisting of: amplify sensor signals, analyze data, analyze sensor information, convert analog signals to digital signals, determine a functional relationship between signal variation and joint angle variation, estimate joint angle, filter signals, model joint configuration, record data, run software applications, run software programs, and store data in memory.

In an example, a data communication component can perform one or more functions selected from the group consisting of: transmit and receive data via Bluetooth, WiFi, Zigbee, or other wireless communication modality; transmit and receive data to and from a mobile electronic device such as a cellular phone, mobile phone, smart phone, electronic tablet; transmit and receive data to and from a separate wearable device such as a smart watch or electronically-functional eyewear; transmit and receive data to and from the internet; send and receive phone calls and electronic messages; transmit and receive data to and from a home appliance and/or home control system; and transmit and receive data to and from an implantable medical device.

In an example, Motion Recognition Clothing™ can further comprise one or more motion-related sensors selected from the group consisting of: dual-axial accelerometer, tri-axial accelerometer, other multi-axial accelerometer, gyroscope, inclinometer or tilt sensor, goniometer, GPS or other location sensor, other inertial or motion sensor, goniometer, and kinematic sensor. In an example, Motion Recognition Clothing™ can further comprise one or more electromagnetic energy sensors selected from the group consisting of: electroencephalography (EEG) sensor, peripheral neurosensor, electromyography (EMG) sensor, Hall-effect sensor, electromagnetic field sensor, electrocardiogram (ECG) sensor, cardiac monitor, EOG sensor, galvanic skin response (GSR) sensor, impedance sensor, compass, magnometer, magnetic sensor, potentiometer, variable-resistance sensor, resistive bend sensor, piezoelectric sensor, piezomechanical sensor, piezoresistive sensor, and other electromagnetic sensor. Variations discussed elsewhere in this disclosure or in priority-linked disclosures can be applied to the example in this figure where relevant.

Figure 4:
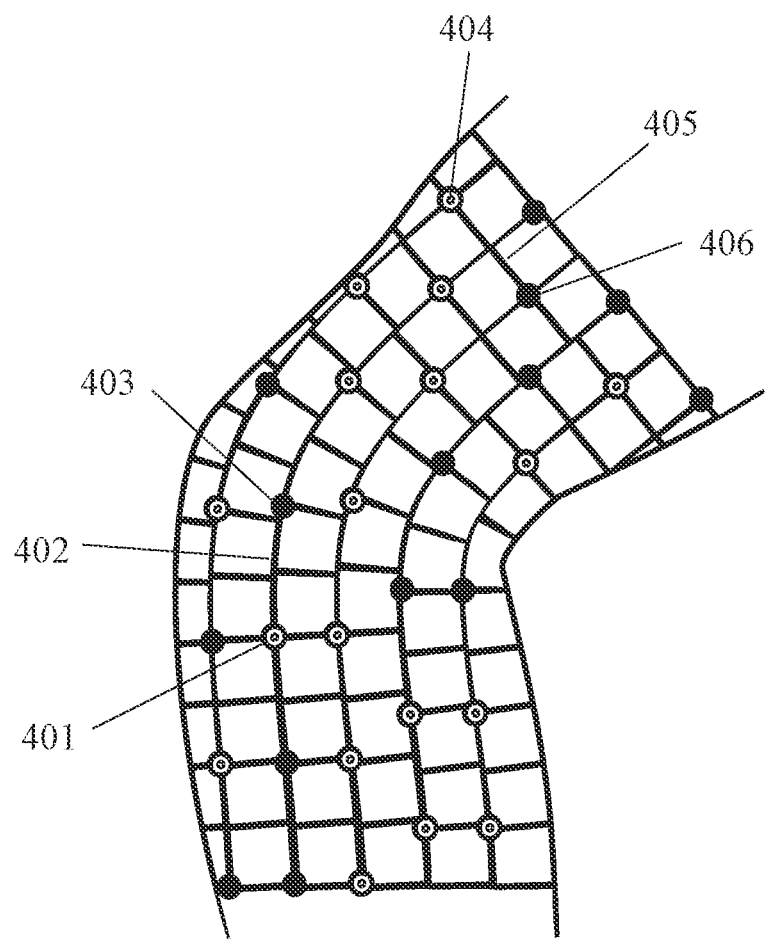
FIG. 4 shows an example with a wearable energy-conducting lattice, mesh, grid, or matrix with multi-directional energy pathways.

FIG. 4 shows an example of how Motion Recognition Clothing™ can be embodied in a wearable device to measure the motion and/or configuration of a body joint comprising—a wearable energy-conducting lattice, mesh, grid, or matrix that is configured to span the surface of a person's body which contains a joint, wherein this lattice, mesh, grid, or matrix further comprises: a plurality of energy pathways including 402 which are configured to span that portion of the body in a longitudinal manner; a plurality of energy pathways including 405 which are configured to span that portion of the body in a (partial) circumferential manner; and a plurality of energy sensors including 401 and 404 which measure energy flow through these energy pathways, wherein data from these sensors are analyzed together using multivariate analysis in order to measure the motion and/or configuration of the body joint.

The example in FIG. 4 further comprises energy input components 403 and 406 which direct energy into the lattice, mesh, grid, or matrix. In an example, there can be a single energy input location rather than a plurality of energy input components. In this example, the longitudinal energy pathways are substantially evenly-spaced around the circumference of the body member containing the joint and the circumferential energy pathways are substantially-evenly spaced along the longitudinal axis of the body member containing the joint. In this example, there are gaps and/or elements in the lattice, mesh, grid, or matrix which are substantially the same in size and are shaped like squares, rhombuses, diamonds, trapezoids, or parallelograms.

In an example, the energy sensors and/or energy input components can be modular and/or moveable. In an example, energy sensors and/or energy input components can be snapped or otherwise removably-connected to the lattice, mesh, grid, or matrix at different locations in order to create different energy pathways. In an example, modular and/or moveable energy sensors and/or energy input components can allow the device to be customized to span different joints and/or be customized to a person's specific body contours. In an example, having removably-connected electronic components can also make it easier to wash the device.

In an example, a plurality of wearable energy pathways can form a mesh, grid, lattice, or matrix with square, rectangular, rhomboid, or trapezoid shaped elements. In an example, a plurality of wearable energy pathways can form a mesh, grid, lattice, or matrix with interlocking and/or repeating square, rectangular, rhomboid, or trapezoid shaped elements. In an example, a plurality of wearable energy pathways can form a mesh, grid, lattice, or matrix with diamond-shaped elements. In an example, a plurality of wearable energy pathways can form a mesh, grid, lattice, or matrix with interlocking and/or repeating diamond-shaped elements. In an example, a plurality of wearable energy pathways can form a hexagonal mesh, grid, lattice, or matrix (e.g. a honeycomb mesh or grid).

In an example, a plurality of wearable energy pathways can form a mesh, grid, lattice, or matrix with a chain of loops. In an example, a plurality of wearable energy pathways can form a mesh, grid, lattice, or matrix with a chain of knitted loops. In an example, a plurality of wearable energy pathways can form a mesh, grid, lattice, or matrix with circular or elliptical elements. In an example, a plurality of wearable energy pathways can form a mesh, grid, lattice, or matrix with interlocking and/or repeating circular or elliptical elements. In an example, a plurality of wearable energy pathways can form a mesh, grid, lattice, or matrix with triangular elements. In an example, a plurality of wearable energy pathways can form a mesh, grid, lattice, or matrix with interlocking and/or repeating triangular elements.

In an example, a plurality of wearable energy pathways in a wearable energy-conducting mesh, grid, lattice, or matrix can be straight. In an example, a plurality of wearable energy pathways in a wearable energy-conducting mesh, grid, lattice, or matrix can be sinusoidal. In an example, a plurality of wearable energy pathways in a wearable energy-conducting mesh, grid, lattice, or matrix can have saw-tooth wave or square-wave shapes. In an example, a plurality of wearable energy pathways in a wearable energy-conducting mesh, grid, lattice, or matrix can have conic section shapes, wherein examples of conic sections include circles, ellipses, parabolas, and hyperbolas. In an example, a plurality of wearable energy pathways in a wearable energy-conducting mesh, grid, lattice, or matrix can have helical or spiral shapes.

In an example, a wearable energy-conducting mesh, grid, lattice, or matrix can comprise square elements, rectangular elements, diamond elements, rhomboid elements, parallelogram elements, trapezoidal elements, triangular elements, hexagonal elements, circular elements, or elliptical elements. In an example, a wearable energy-conducting mesh, grid, lattice, or matrix can comprise interlocking and/or repeating square elements, rectangular elements, diamond elements, rhomboid elements, parallelogram elements, trapezoidal elements, triangular elements, hexagonal elements, circular elements, or elliptical elements.

In an example, a wearable energy-conducting mesh, grid, lattice, or matrix can comprise a repeating pattern of quadrilateral (e.g. square, rectangular, trapezoidal, parallelogram, or diamond shaped) elements. In an example, a wearable energy-conducting mesh, grid, lattice, or matrix can comprise a repeating pattern of hexagonal elements (e.g. a honeycomb mesh). In an example, a wearable energy-conducting mesh, grid, lattice, or matrix can comprise a repeating pattern of arcuate elements created by parallel, different-phase sinusoidal curves. In an example, a wearable energy-conducting mesh, grid, lattice, or matrix can comprise a repeating pattern of arcuate elements created by intersecting sinusoidal curves.

In an example, geometric relationships between energy pathways in a wearable energy-conducting mesh, grid, lattice, or matrix can be selected from the group consisting of: substantially parallel; separated by a substantially-constant distance; separated by a substantially-constant number of radial degrees of the cross-sectional perimeter of a body member; separated by a substantially-constant percentage of the cross-sectional perimeter of a body member; forming vectors which intersect in 3D space at a right angle; substantially-parallel as they span a distal portion of a joint and diverging as they span a proximal portion of a joint; substantially-parallel as they span a proximal portion of a joint and diverging as they span a distal portion of a joint; substantially perpendicular; intersecting at an acute angle; forming vectors which intersect in 3D space at an acute angle; substantially diagonal to each other; plaited together; woven together; braided together; combining to form a 3D lattice, mesh, or grid; differing in length; nested; forming a rainbow arc configuration; radial vectors with a common point of convergence; straight vectors with a common convergence point; and arcuate elements with a common convergence point.

In an example, energy pathways in a wearable energy-conducting mesh, grid, lattice, or matrix can differ in the angles at which they span the longitudinal axis of a body member which contains a body joint. In an example, different energy pathways in a wearable energy-conducting mesh, grid, lattice, or matrix can span a body joint at different angles. In an example, having different energy pathways span a body joint at different angles can be especially useful for measuring the motion and/or configuration of ball-and-socket or other complex motion joints. In an example, energy pathways in a wearable energy-conducting mesh, grid, lattice, or matrix can have longitudinal axes which intersect each other in an orthogonal manner. In an example, energy pathways in a wearable energy-conducting mesh, grid, lattice, or matrix can have longitudinal axes which intersect each other at acute angles.

In an example, energy pathways in a wearable energy-conducting mesh, grid, lattice, or matrix can form interpathway areas which, when projected from 3D space onto a 2D plane, are squares or rectangles. In an example, one or more aspects of the geometric relationship between energy pathways in a wearable energy-conducting mesh, grid, lattice, or matrix can be selected from the group consisting of: substantially parallel; separated by a substantially-constant distance; intersecting at an acute angle; forming vectors which intersect in 3D space at an acute angle; combining to form a 3D mesh, grid, lattice, or matrix; differing in length; substantially concentric; nested; differing in diameter; knitted together in loops; and tangential.

In an example, one or more aspects of the geometric relationship between energy pathways in a wearable energy-conducting mesh, grid, lattice, or matrix can be selected from the group consisting of: substantially perpendicular; intersecting at a right angle; intersecting at an acute angle; defining square-shaped spaces (when projected onto a 2D plane) as they intersect; defining rhomboid-shaped spaces (when projected onto a 2D plane) as they intersect; defining trapezoid-shaped spaces (when projected onto a 2D plane) as they intersect; plaited together; woven together; braided together; combining to form a 3D mesh, grid, lattice, or matrix; overlapping; and tangential.

In an example, energy pathways in a wearable energy-conducting mesh, grid, lattice, or matrix can have substantially straight configurations when a joint is fully extended. In an example, energy pathways in a wearable energy-conducting mesh, grid, lattice, or matrix can have arcuate shapes, even when a joint is fully extended. In an example, a wearable energy-conducting mesh, grid, lattice, or matrix can have a repeating pattern or waveform selected from the group consisting of: simple sinusoidal wave; composite sinusoidal wave; saw-tooth wave or zigzag; and square wave. In an example, an energy pathway can have a shape which is a conic section. In an example, an energy pathway can have a shape which is a spiral or helix. In an example, an energy pathway can have a shape which is a chain of loops.

In an example, the flows of energy through energy pathways in a wearable energy-conducting mesh, grid, lattice, or matrix can be independent and/or separate. In an example, the flows of energy through energy pathways in a wearable energy-conducting mesh, grid, lattice, or matrix can interact and/or combine with each other. In an example, energy pathways in a wearable energy-conducting mesh, grid, lattice, or matrix can be in electromagnetic communication with each other.

In an example, energy pathways in a wearable energy-conducting mesh, grid, lattice, or matrix can differ by one or more parameters selected from the group consisting of: the angle at which they span the body joint; length; longitudinal curvature or convolution; longitudinal waveform; flexibility; elasticity; electrical resistance or impedance; transparency; and cross-sectional shape. In an example, energy pathways in a wearable energy-conducting mesh, grid, lattice, or matrix can differ in the angles at which they span the body member. In an example, energy pathways in a wearable energy-conducting mesh, grid, lattice, or matrix can differ in length. In an example, energy pathways in a wearable energy-conducting mesh, grid, lattice, or matrix can differ in longitudinal curvature or convolution.

In an example, energy pathways in a wearable energy-conducting mesh, grid, lattice, or matrix can differ in flexibility. In an example, energy pathways in a wearable energy-conducting mesh, grid, lattice, or matrix can differ in elasticity. In an example, energy pathways in a wearable energy-conducting mesh, grid, lattice, or matrix can differ in electrical resistance or impedance. In an example, energy pathways in a wearable energy-conducting mesh, grid, lattice, or matrix can differ in cross-sectional shape.

In an example, energy pathways in a wearable energy-conducting mesh, grid, lattice, or matrix can be woven together in a substantially-perpendicular manner to form a textile. In an example, energy pathways in a wearable energy-conducting mesh, grid, lattice, or matrix can be knitted together. In an example, energy pathways in a wearable energy-conducting mesh, grid, lattice, or matrix can be knitted together in a chain of loops. In an example, energy pathways in a wearable energy-conducting mesh, grid, lattice, or matrix can be plaited, knitted, woven together, or braided together.

In an example, the relationship between energy flow in an energy pathway and the configuration of a body joint spanned by that energy pathway can be nonlinear and/or stochastic. In an example, data from multiple energy pathways can be jointly analyzed using one or more statistical methods selected from the group consisting of: multivariate linear regression or least squares estimation; factor analysis; Fourier Transformation; mean; median; multivariate logit; principal components analysis; spline function; auto-regression; carlavian curve analysis, centroid analysis; correlation; covariance; decision tree analysis; kinematic modeling; Kalman filter; linear discriminant analysis; linear transform; logarithmic function; logit analysis; Markov model; multi-variate parametric classifiers; non-linear programming; orthogonal transformation; pattern recognition; random forest analysis; spectroscopic analysis; variance; artificial neural network; Bayesian filter or other Bayesian statistical method; chi-squared; eigenvalue decomposition; logit model; machine learning; power spectral density; power spectrum analysis; probit model; and time-series analysis.

In an example, repeated or cyclical patterns of movement such as walking or running can be identified and analyzed using Fourier analysis. In an example, the speed of repeated movement cycles can influence the functional relationship between the flow of energy through an energy pathway and the angle of a joint. In an example, the speed of repeated cycles can especially influence this functional relationship at the end-points of a cycle wherein joint movement reverses direction. In an example, analyzing and identifying the speed of repeated or cyclical patterns of movement using Fourier transform methods can improve the accuracy of measuring joint motion and configuration.

In an example, data from different energy pathways in a wearable energy-conducting mesh, grid, lattice, or matrix can be given different weights during different portions of the joint range of motion in order to improve accuracy and reduce error in the measurement of the motion and/or configuration of that joint. In an example, data from different energy pathways in a wearable energy-conducting mesh, grid, lattice, or matrix can be given different weights during different directions of joint motion (e.g. flexion vs. extension) in order to improve accuracy and reduce error in the measurement of the motion and/or configuration of that joint. In an example, data from different energy pathways in a wearable energy-conducting mesh, grid, lattice, or matrix can be given different weights during different movement speeds (e.g. fast movement vs. slow movement) of joint motion in order to improve accuracy and reduce error in the measurement of the motion and/or configuration of that joint.

In an example, changes in the flows of electromagnetic energy can be measured by one or more parameters selected from the group consisting of: voltage, resistance, impedance, amperage, current, phase, and wave pattern. In an example, an electromagnetic energy pathway can be comprised of electroconductive fibers, yarns, threads, strands, substrates, layers, or textiles. In an example, an electromagnetic energy sensor can be selected from the group consisting of: voltmeter, impedance sensor, magnetic field sensor, piezoelectric sensor, piezomechanical sensor, potentiometer, resistive bend sensor, variable-resistance sensor, electromyography (EMG) sensor, and Hall-effect sensor.

In an example, electromagnetic energy can be directed into an energy pathway at a first location and electromagnetic energy from the energy pathway can be measured from the energy pathway at a second location. In an example, electromagnetic energy can be directed into a wearable mesh, grid, lattice, or matrix of conductive pathways at a first location and received out from the mesh, grid, lattice, or matrix at a second location. In an example, electromagnetic energy can be directed into a wearable mesh, grid, lattice, or matrix of conductive pathways at a first vertex (or juncture of energy-conducting pathways) and received out from the mesh, grid, lattice, or matrix at a second vertex (or juncture of energy-conducting pathways). In an example, electromagnetic energy can be directed into a wearable mesh, grid, lattice, or matrix of conductive pathways at a first set of multiple location, vertexes, and/or pathway junctures and received out from the mesh, grid, lattice, or matrix at a second set of multiple location, vertexes, and/or pathway junctures In an example, electromagnetic energy can be transmitted into an energy pathway at a first location and electromagnetic energy from the energy pathway can be measured from the energy pathway at a second location. In an example, electromagnetic energy can be transmitted into a wearable mesh, grid, lattice, or matrix of conductive pathways at a first location and measured from the mesh, grid, lattice, or matrix at a second location. In an example, electromagnetic energy can be transmitted into a wearable mesh, grid, lattice, or matrix of conductive pathways at a first vertex (or juncture of energy-conducting pathways) and measured from the mesh, grid, lattice, or matrix at a second vertex (or juncture of energy-conducting pathways). In an example, electromagnetic energy can be transmitted into a wearable mesh, grid, lattice, or matrix of conductive pathways at a first set of multiple location, vertexes, and/or pathway junctures and measured from the mesh, grid, lattice, or matrix at a second set of multiple location, vertexes, and/or pathway junctures In an example, wearable energy pathways in a wearable mesh, grid, lattice, or matrix can comprise non-conductive or less-conductive fibers, traces, yarns, strands, or textiles which are coated, impregnated, or otherwise integrated with conductive material or particles. In an example, a non-conductive or less-conductive fiber, trace, yarn, strand, or textile can be selected from the group consisting of: acetate, acrylic, cotton, denim, elastane, Kevlar, latex, linen, Lycra, neoprene, nylon, nylon, polyester, wool, silicon rubber, silk, spandex, Danconn or rayon. In an example, conductive material or particles used for coating or impregnation can be selected from the group consisting of: aluminum or aluminum alloy; carbon nanotubes, graphene, or other carbon-based material; magnesium; ceramic particles; copper or copper alloy; gold; nickel; polyaniline; silver; and steel.

In an example, a wearable energy-conducting mesh, grid, lattice, or matrix can comprise one or more of the following: array of electroconductive members woven using a plain weave, rib weave, basket weave, twill weave, satin weave, leno weave, mock leno weave, or conan weave; array of fiber optic members woven using a plain weave, rib weave, basket weave, twill weave, satin weave, leno weave, mock leno weave; array of light-emitting fibers, threads, or yarns; array of sound-conducting members woven using a plain weave, rib weave, basket weave, twill weave, satin weave, leno weave, mock leno weave; array or mesh of electroconductive fibers; bendable fibers, threads, or yarns; bendable layer, trace, or substrate; elastic fibers, threads, or yarns; elastic layer, trace, or substrate; electroconductive fibers, threads, or yarns; electronically-functional bandage; electronically-functional tattoo; integrated array of electroconductive members; integrated array of fiber optic members; integrated array of sound-conducting members; interlaced electricity-conducting fibers, threads, or yarns; interlaced light-conducting fibers, threads, or yarns; interlaced sound-conducting fibers, threads, or yarns; light-emitting fibers, threads, or yarns; nonconductive fibers, threads, or yarns; nonconductive layer, substrate, or material; plaited fibers, threads, or yarns; sinusoidal fibers, threads, or yarns; stretchable fibers, threads, or yarns; stretchable layer, trace, or substrate; textile-based light display matrix; variable-resistance electroconductive fiber, thread, or yarn; variable-translucence fiber, thread, or yarn; water-resistant fibers, threads, or yarns; a layer or coating of metallic nanoparticles; a graphene layer; and water-resistant layer, trace, or substrate.

In an example, a wearable energy-conducting mesh, grid, lattice, or matrix can be incorporated into an article of clothing which is, in turn, worn over a body member containing a body joint. Changes in energy conducted through these pathways can be used to estimate joint motion and/or configuration. In an example, an array of energy pathways can be directly attached to a body member containing a body joint. In an example, energy pathways can be incorporated into an article of clothing or directly attached to a body member using one or more means selected from the group consisting of: adhesion, armband, article of clothing, bangle, belt, bracelet, buckle, button, clasp, clip, elastic band, elastic garment, eyewear, fabric layer, garment channel, garment pocket, gluing, hook, hook-and-eye attachment mechanism, incorporation into a bandage, incorporation into a tattoo, knitting, loop, magnetism, melting, metal fibers, nanoscale fibers, necklace, pin, polymer fibers, sewing, skin-adhesive patch, smart watch, snap, strands, strap, tape, textile channel, textile fibers, thermal bonding, tubular garment, waist band, weaving, wrist band, yarn, and zipper.

In an example, a wearable energy-conducting mesh, grid, lattice, or matrix can be incorporated into an article of clothing or clothing accessory selected from the group consisting of: an upper body garment such as a shirt, t-shirt, blouse, jacket, hoodie, sweatshirt, undershirt, brassier, girdle, blouse, or glove; a lower body garment such as a pair of pants, sweatpants, trousers, slacks, leggings, tights, underpants, pantyhose, shorts, or sock; a full-body garment such as a union suit, jump suit, pair of overalls, or dress; a clothing accessory such as shoe, boot, insole, hat, cap, headband, armband, strap, torso band, tubular accessory, wristband, other band, knee or elbow brace, back brace, knee or elbow pad, belt, bandage, electronic tattoo, or wearable patch.

In various examples, a wearable energy-conducting mesh, grid, lattice, or matrix can measure one or more joint configurations and/or motions selected from the group consisting of: eversion, extension, flexion, and/or inversion of the ankle; abduction, extension, flexion, lateral bending, and/or rotation of the spine; eversion, extension, flexion, and/or inversion of the elbow; extension and/or flexion of the finger or thumb; pronation, rotation, and/or supination of the forearm; abduction, adduction, extension, flexion, and/or rotation of the hip; extension and/or flexion of the jaw; abduction, adduction, extension, and/or flexion of the knee; eversion and/or inversion of the mid-tarsal; abduction, extension, flexion, and/or rotation of the neck; abduction, adduction, extension, flexion, and/or rotation of the shoulder; extension and/or flexion of the toe; and abduction, extension, flexion, and/or ulnar deviation or radial deviation of the wrist.

In an example, a wearable energy-conducting mesh, grid, lattice, or matrix can span the surface of the portion of the body containing one or more body joints selected from the group consisting of: ankle, elbow, finger, forearm, hip, jaw, knee, mid-tarsal, neck, shoulder, spine, thumb, toe, and wrist. In an example, a wearable energy-conducting mesh, grid, lattice, or matrix can span the surface of a body member containing the finger and thumb. In an example, a wearable energy-conducting mesh, grid, lattice, or matrix can span the surface of a body member containing the finger, forearm, thumb and wrist. In an example, a wearable energy-conducting mesh, grid, lattice, or matrix can span the surface of a body member containing the elbow, forearm and wrist.

In an example, a wearable energy-conducting mesh, grid, lattice, or matrix can span the surface of a body member containing an elbow. In an example, a wearable energy-conducting mesh, grid, lattice, or matrix can span the surface of the body containing an elbow, forearm, shoulder and spine. In an example, a wearable energy-conducting mesh, grid, lattice, or matrix can span the surface of a body member containing a hip and knee. In an example, a wearable energy-conducting mesh, grid, lattice, or matrix can span the surface of a body member containing the spine. In an example, a wearable energy-conducting mesh, grid, lattice, or matrix can span the surface of a body member containing an ankle, mid-tarsal and toe. In an example, a wearable energy-conducting mesh, grid, lattice, or matrix can span the surface of the portion of the body containing the neck, shoulder and spine.

In an example, an article of clothing or clothing accessory can be selected from the group consisting of: a shirt, a pair of shorts, a pair of pants, and a full-body suit. In an example, an article of clothing or wearable accessory can be selected from the group consisting of: ankle band, ankle tube, arm band, arm tube, belt, bra, collar, elbow pad, elbow tube, finger tube, girdle, glove, hip pad, hoodie, knee pad, knee tube, neck band, other wearable top, pair of pants, shirt, shoe, shorts, shoulder pad, shoulder tube, sock, suit, torso band, torso tube, underwear, union suit, waist band, and waist tube. In an example, energy pathway can be connected to an article of clothing or wearable accessory by a means selected from the group consisting of: weaving, knitting, and/or sewing; adhesion and/or gluing; hook-and-eye attachment mechanisms; snaps, buckles, straps, or clips; magnetic force; integration with threads, strands, yarns, elastic bands, textile fibers, polymer fibers, metal fibers, and/or nanoscale fibers; and connection by threads, strands, yarns, elastic bands, textile fibers, polymer fibers, metal fibers, and/or nanoscale fibers.

In an example, energy flow through or from different energy pathways in a wearable energy-conducting mesh, grid, lattice, or matrix can differ in one or more parameters selected from the group consisting of: total energy; energy flow per time period; energy power; wave amplitude; wave frequency; wave phase; waveform; frequency range; spectral distribution; resistance; voltage; current; impedance; and interval pattern.

In an example, Motion Recognition Clothing™ can also include a data control unit which further comprises one or more components selected from the group consisting of: a data processing component, a data communication component, a power source, a human-to-computer user interface, a computer-to-human interface, and a digital memory. In an example, a data control unit can be temporarily detached so that the remaining wearable portion of the invention can be washed. In an example, a data processing component can perform one or more functions selected from the group consisting of: amplify sensor signals, analyze data, analyze sensor information, convert analog signals to digital signals, determine a functional relationship between signal variation and joint angle variation, estimate joint angle, filter signals, model joint configuration, record data, run software applications, run software programs, and store data in memory.

In an example, a data communication component can perform one or more functions selected from the group consisting of: transmit and receive data via Bluetooth, WiFi, Zigbee, or other wireless communication modality; transmit and receive data to and from a mobile electronic device such as a cellular phone, mobile phone, smart phone, electronic tablet; transmit and receive data to and from a separate wearable device such as a smart watch or electronically-functional eyewear; transmit and receive data to and from the internet; send and receive phone calls and electronic messages; transmit and receive data to and from a home appliance and/or home control system; and transmit and receive data to and from an implantable medical device.

In an example, Motion Recognition Clothing™ can further comprise one or more motion-related sensors selected from the group consisting of: dual-axial accelerometer, tri-axial accelerometer, other multi-axial accelerometer, gyroscope, inclinometer or tilt sensor, goniometer, GPS or other location sensor, other inertial or motion sensor, goniometer, and kinematic sensor. In an example, Motion Recognition Clothing™ can further comprise one or more electromagnetic energy sensors selected from the group consisting of: electroencephalography (EEG) sensor, peripheral neurosensor, electromyography (EMG) sensor, Hall-effect sensor, electromagnetic field sensor, electrocardiogram (ECG) sensor, cardiac monitor, EOG sensor, galvanic skin response (GSR) sensor, impedance sensor, compass, magnometer, magnetic sensor, potentiometer, variable-resistance sensor, resistive bend sensor, piezoelectric sensor, piezomechanical sensor, piezoresistive sensor, and other electromagnetic sensor. Variations discussed elsewhere in this disclosure or in priority-linked disclosures can be applied to the example in this figure where relevant.

Figure 5:
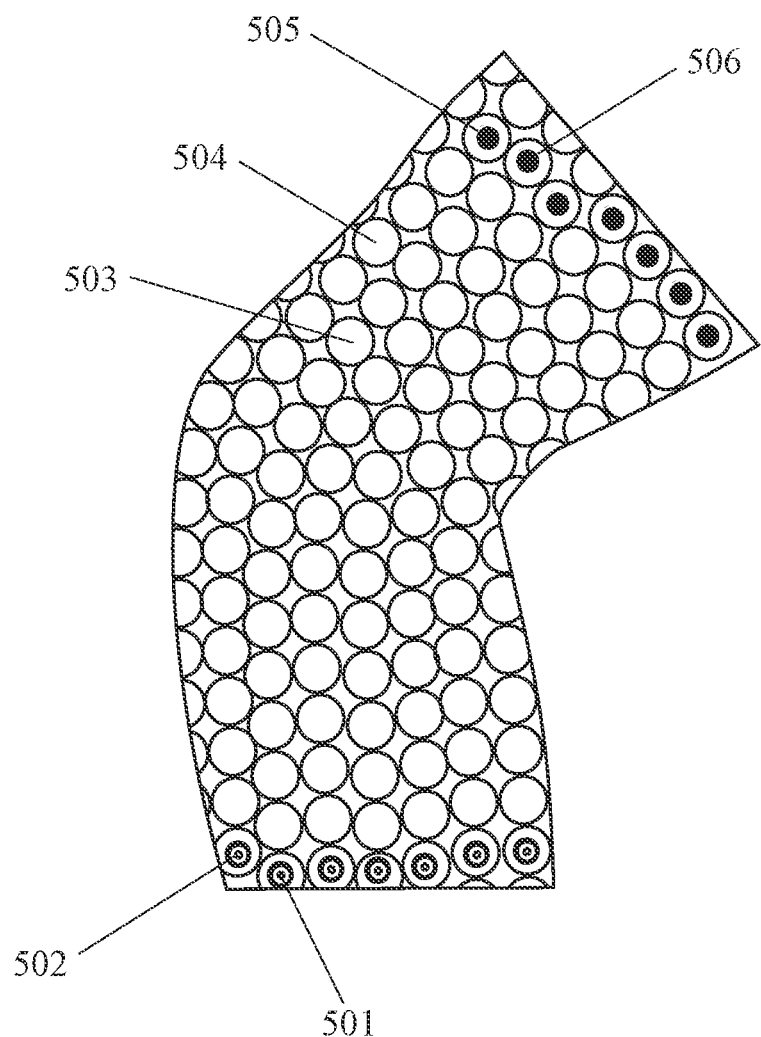
FIG. 5 shows an example with a wearable energy-conducting lattice, mesh, grid, or matrix of arcuate elements and longitudinal energy pathways.

FIG. 5 shows an example of how Motion Recognition Clothing™ can be embodied in a wearable device to measure the motion and/or configuration of a body joint comprising—a wearable energy-conducting lattice, mesh, grid, or matrix that is configured to span the surface of a person's body which contains a joint, wherein this lattice, mesh, grid, or matrix further comprises: a plurality of arcuate energy-conducting elements including 503 and 504; a plurality of energy pathways spanning multiple arcuate energy-conducting elements which are configured to span that portion of the body in a longitudinal manner (from a proximal portion of the joint to a distal portion of the joint, or vice versa); and a plurality of energy sensors including 501 and 502 which measure energy flow through these energy pathways, wherein data from these sensors are analyzed together using multivariate analysis in order to measure the motion and/or configuration of the body joint.

The example in FIG. 5 further comprises energy input components 505 and 506 which direct energy into the lattice, mesh, grid, or matrix. In an example, there can be a single energy input location rather than a plurality of energy input components. In this example, the energy pathways are substantially parallel. In this example, the energy pathways are substantially evenly-spaced around the circumference of the body member containing the joint. In this example, the arcuate elements are substantially the same in size and are circular, oval, or elliptical in shape.

In an example, the energy sensors and/or energy input components can be modular and/or moveable. In an example, energy sensors and/or energy input components can be snapped or otherwise removably-connected to the lattice, mesh, grid, or matrix at different locations in order to create different energy pathways. In an example, modular and/or moveable energy sensors and/or energy input components can allow the device to be customized to span different joints and/or be customized to a person's specific body contours. In an example, having removably-connected electronic components can also make it easier to wash the device.

In an example, a plurality of wearable energy pathways can form a mesh, grid, lattice, or matrix with square, rectangular, rhomboid, or trapezoid shaped elements. In an example, a plurality of wearable energy pathways can form a mesh, grid, lattice, or matrix with interlocking and/or repeating square, rectangular, rhomboid, or trapezoid shaped elements. In an example, a plurality of wearable energy pathways can form a mesh, grid, lattice, or matrix with diamond-shaped elements. In an example, a plurality of wearable energy pathways can form a mesh, grid, lattice, or matrix with interlocking and/or repeating diamond-shaped elements. In an example, a plurality of wearable energy pathways can form a hexagonal mesh, grid, lattice, or matrix (e.g. a honeycomb mesh or grid).

In an example, a plurality of wearable energy pathways can form a mesh, grid, lattice, or matrix with a chain of loops. In an example, a plurality of wearable energy pathways can form a mesh, grid, lattice, or matrix with a chain of knitted loops. In an example, a plurality of wearable energy pathways can form a mesh, grid, lattice, or matrix with circular or elliptical elements. In an example, a plurality of wearable energy pathways can form a mesh, grid, lattice, or matrix with interlocking and/or repeating circular or elliptical elements. In an example, a plurality of wearable energy pathways can form a mesh, grid, lattice, or matrix with triangular elements. In an example, a plurality of wearable energy pathways can form a mesh, grid, lattice, or matrix with interlocking and/or repeating triangular elements.

In an example, a plurality of wearable energy pathways in a wearable energy-conducting mesh, grid, lattice, or matrix can be straight. In an example, a plurality of wearable energy pathways in a wearable energy-conducting mesh, grid, lattice, or matrix can be sinusoidal. In an example, a plurality of wearable energy pathways in a wearable energy-conducting mesh, grid, lattice, or matrix can have saw-tooth wave or square-wave shapes. In an example, a plurality of wearable energy pathways in a wearable energy-conducting mesh, grid, lattice, or matrix can have conic section shapes, wherein examples of conic sections include circles, ellipses, parabolas, and hyperbolas. In an example, a plurality of wearable energy pathways in a wearable energy-conducting mesh, grid, lattice, or matrix can have helical or spiral shapes.

In an example, a wearable energy-conducting mesh, grid, lattice, or matrix can comprise square elements, rectangular elements, diamond elements, rhomboid elements, parallelogram elements, trapezoidal elements, triangular elements, hexagonal elements, circular elements, or elliptical elements. In an example, a wearable energy-conducting mesh, grid, lattice, or matrix can comprise interlocking and/or repeating square elements, rectangular elements, diamond elements, rhomboid elements, parallelogram elements, trapezoidal elements, triangular elements, hexagonal elements, circular elements, or elliptical elements.

In an example, a wearable energy-conducting mesh, grid, lattice, or matrix can comprise a repeating pattern of quadrilateral (e.g. square, rectangular, trapezoidal, parallelogram, or diamond shaped) elements. In an example, a wearable energy-conducting mesh, grid, lattice, or matrix can comprise a repeating pattern of hexagonal elements (e.g. a honeycomb mesh). In an example, a wearable energy-conducting mesh, grid, lattice, or matrix can comprise a repeating pattern of arcuate elements created by parallel, different-phase sinusoidal curves. In an example, a wearable energy-conducting mesh, grid, lattice, or matrix can comprise a repeating pattern of arcuate elements created by intersecting sinusoidal curves.

In an example, geometric relationships between energy pathways in a wearable energy-conducting mesh, grid, lattice, or matrix can be selected from the group consisting of: substantially parallel; separated by a substantially-constant distance; separated by a substantially-constant number of radial degrees of the cross-sectional perimeter of a body member; separated by a substantially-constant percentage of the cross-sectional perimeter of a body member; forming vectors which intersect in 3D space at a right angle; substantially-parallel as they span a distal portion of a joint and diverging as they span a proximal portion of a joint; substantially-parallel as they span a proximal portion of a joint and diverging as they span a distal portion of a joint; substantially perpendicular; intersecting at an acute angle; forming vectors which intersect in 3D space at an acute angle; substantially diagonal to each other; plaited together; woven together; braided together; combining to form a 3D lattice, mesh, or grid; differing in length; nested; forming a rainbow arc configuration; radial vectors with a common point of convergence; straight vectors with a common convergence point; and arcuate elements with a common convergence point.

In an example, energy pathways in a wearable energy-conducting mesh, grid, lattice, or matrix can differ in the angles at which they span the longitudinal axis of a body member which contains a body joint. In an example, different energy pathways in a wearable energy-conducting mesh, grid, lattice, or matrix can span a body joint at different angles. In an example, having different energy pathways span a body joint at different angles can be especially useful for measuring the motion and/or configuration of ball-and-socket or other complex motion joints. In an example, energy pathways in a wearable energy-conducting mesh, grid, lattice, or matrix can have longitudinal axes which intersect each other in an orthogonal manner. In an example, energy pathways in a wearable energy-conducting mesh, grid, lattice, or matrix can have longitudinal axes which intersect each other at acute angles.

In an example, energy pathways in a wearable energy-conducting mesh, grid, lattice, or matrix can form inter-pathway areas which, when projected from 3D space onto a 2D plane, are squares or rectangles. In an example, one or more aspects of the geometric relationship between energy pathways in a wearable energy-conducting mesh, grid, lattice, or matrix can be selected from the group consisting of: substantially parallel; separated by a substantially-constant distance; intersecting at an acute angle; forming vectors which intersect in 3D space at an acute angle; combining to form a 3D mesh, grid, lattice, or matrix; differing in length; substantially concentric; nested; differing in diameter; knitted together in loops; and tangential.

In an example, one or more aspects of the geometric relationship between energy pathways in a wearable energy-conducting mesh, grid, lattice, or matrix can be selected from the group consisting of: substantially perpendicular; intersecting at a right angle; intersecting at an acute angle; defining square-shaped spaces (when projected onto a 2D plane) as they intersect; defining rhomboid-shaped spaces (when projected onto a 2D plane) as they intersect; defining trapezoid-shaped spaces (when projected onto a 2D plane) as they intersect; plaited together; woven together; braided together; combining to form a 3D mesh, grid, lattice, or matrix; overlapping; and tangential.

In an example, energy pathways in a wearable energy-conducting mesh, grid, lattice, or matrix can have substantially straight configurations when a joint is fully extended. In an example, energy pathways in a wearable energy-conducting mesh, grid, lattice, or matrix can have arcuate shapes, even when a joint is fully extended. In an example, a wearable energy-conducting mesh, grid, lattice, or matrix can have a repeating pattern or waveform selected from the group consisting of: simple sinusoidal wave; composite sinusoidal wave; saw-tooth wave or zigzag; and square wave. In an example, an energy pathway can have a shape which is a conic section. In an example, an energy pathway can have a shape which is a spiral or helix. In an example, an energy pathway can have a shape which is a chain of loops.

In an example, the flows of energy through energy pathways in a wearable energy-conducting mesh, grid, lattice, or matrix can be independent and/or separate. In an example, the flows of energy through energy pathways in a wearable energy-conducting mesh, grid, lattice, or matrix can interact and/or combine with each other. In an example, energy pathways in a wearable energy-conducting mesh, grid, lattice, or matrix can be in electromagnetic communication with each other.

In an example, energy pathways in a wearable energy-conducting mesh, grid, lattice, or matrix can differ by one or more parameters selected from the group consisting of: the angle at which they span the body joint; length; longitudinal curvature or convolution; longitudinal waveform; flexibility; elasticity; electrical resistance or impedance; transparency; and cross-sectional shape. In an example, energy pathways in a wearable energy-conducting mesh, grid, lattice, or matrix can differ in the angles at which they span the body member. In an example, energy pathways in a wearable energy-conducting mesh, grid, lattice, or matrix can differ in length. In an example, energy pathways in a wearable energy-conducting mesh, grid, lattice, or matrix can differ in longitudinal curvature or convolution.

In an example, energy pathways in a wearable energy-conducting mesh, grid, lattice, or matrix can differ in flexibility. In an example, energy pathways in a wearable energy-conducting mesh, grid, lattice, or matrix can differ in elasticity. In an example, energy pathways in a wearable energy-conducting mesh, grid, lattice, or matrix can differ in electrical resistance or impedance. In an example, energy pathways in a wearable energy-conducting mesh, grid, lattice, or matrix can differ in cross-sectional shape.

In an example, energy pathways in a wearable energy-conducting mesh, grid, lattice, or matrix can be woven together in a substantially-perpendicular manner to form a textile. In an example, energy pathways in a wearable energy-conducting mesh, grid, lattice, or matrix can be knitted together. In an example, energy pathways in a wearable energy-conducting mesh, grid, lattice, or matrix can be knitted together in a chain of loops. In an example, energy pathways in a wearable energy-conducting mesh, grid, lattice, or matrix can be plaited, knitted, woven together, or braided together.

In an example, the relationship between energy flow in an energy pathway and the configuration of a body joint spanned by that energy pathway can be nonlinear and/or stochastic. In an example, data from multiple energy pathways can be jointly analyzed using one or more statistical methods selected from the group consisting of: multivariate linear regression or least squares estimation; factor analysis; Fourier Transformation; mean; median; multivariate logit; principal components analysis; spline function; auto-regression; carlavian curve analysis, centroid analysis; correlation; covariance; decision tree analysis; kinematic modeling; Kalman filter; linear discriminant analysis; linear transform; logarithmic function; logit analysis; Markov model; multivariate parametric classifiers; non-linear programming; orthogonal transformation; pattern recognition; random forest analysis; spectroscopic analysis; variance; artificial neural network; Bayesian filter or other Bayesian statistical method; chi-squared; eigenvalue decomposition; logit model; machine learning; power spectral density; power spectrum analysis; probit model; and time-series analysis.

In an example, repeated or cyclical patterns of movement such as walking or running can be identified and analyzed using Fourier analysis. In an example, the speed of repeated movement cycles can influence the functional relationship between the flow of energy through an energy pathway and the angle of a joint. In an example, the speed of repeated cycles can especially influence this functional relationship at the end-points of a cycle wherein joint movement reverses direction. In an example, analyzing and identifying the speed of repeated or cyclical patterns of movement using Fourier transform methods can improve the accuracy of measuring joint motion and configuration.

In an example, data from different energy pathways in a wearable energy-conducting mesh, grid, lattice, or matrix can be given different weights during different portions of the joint range of motion in order to improve accuracy and reduce error in the measurement of the motion and/or configuration of that joint. In an example, data from different energy pathways in a wearable energy-conducting mesh, grid, lattice, or matrix can be given different weights during different directions of joint motion (e.g. flexion vs. extension) in order to improve accuracy and reduce error in the measurement of the motion and/or configuration of that joint. In an example, data from different energy pathways in a wearable energy-conducting mesh, grid, lattice, or matrix can be given different weights during different movement speeds (e.g. fast movement vs. slow movement) of joint motion in order to improve accuracy and reduce error in the measurement of the motion and/or configuration of that joint.

In an example, changes in the flows of electromagnetic energy can be measured by one or more parameters selected from the group consisting of: voltage, resistance, impedance, amperage, current, phase, and wave pattern. In an example, an electromagnetic energy pathway can be comprised of electroconductive fibers, yarns, threads, strands, substrates, layers, or textiles. In an example, an electromagnetic energy sensor can be selected from the group consisting of: voltmeter, impedance sensor, magnetic field sensor, piezoelectric sensor, piezomechanical sensor, potentiometer, resistive bend sensor, variable-resistance sensor, electromyography (EMG) sensor, and Hall-effect sensor.

In an example, electromagnetic energy can be directed into an energy pathway at a first location and electromagnetic energy from the energy pathway can be measured from the energy pathway at a second location. In an example, electromagnetic energy can be directed into a wearable mesh, grid, lattice, or matrix of conductive pathways at a first location and received out from the mesh, grid, lattice, or matrix at a second location. In an example, electromagnetic energy can be directed into a wearable mesh, grid, lattice, or matrix of conductive pathways at a first vertex (or juncture of energy-conducting pathways) and received out from the mesh, grid, lattice, or matrix at a second vertex (or juncture of energy-conducting pathways). In an example, electromagnetic energy can be directed into a wearable mesh, grid, lattice, or matrix of conductive pathways at a first set of multiple location, vertexes, and/or pathway junctures and received out from the mesh, grid, lattice, or matrix at a second set of multiple location, vertexes, and/or pathway junctures In an example, electromagnetic energy can be transmitted into an energy pathway at a first location and electromagnetic energy from the energy pathway can be measured from the energy pathway at a second location. In an example, electromagnetic energy can be transmitted into a wearable mesh, grid, lattice, or matrix of conductive pathways at a first location and measured from the mesh, grid, lattice, or matrix at a second location. In an example, electromagnetic energy can be transmitted into a wearable mesh, grid, lattice, or matrix of conductive pathways at a first vertex (or juncture of energy-conducting pathways) and measured from the mesh, grid, lattice, or matrix at a second vertex (or juncture of energy-conducting pathways). In an example, electromagnetic energy can be transmitted into a wearable mesh, grid, lattice, or matrix of conductive pathways at a first set of multiple location, vertexes, and/or pathway junctures and measured from the mesh, grid, lattice, or matrix at a second set of multiple location, vertexes, and/or pathway junctures In an example, wearable energy pathways in a wearable mesh, grid, lattice, or matrix can comprise non-conductive or less-conductive fibers, traces, yarns, strands, or textiles which are coated, impregnated, or otherwise integrated with conductive material or particles. In an example, a non-conductive or less-conductive fiber, trace, yarn, strand, or textile can be selected from the group consisting of: acetate, acrylic, cotton, denim, elastane, Kevlar, latex, linen, Lycra, neoprene, nylon, nylon, polyester, wool, silicon rubber, silk, spandex, Danconn or rayon. In an example, conductive material or particles used for coating or impregnation can be selected from the group consisting of: aluminum or aluminum alloy; carbon nanotubes, graphene, or other carbon-based material; magnesium; ceramic particles; copper or copper alloy; gold; nickel; polyaniline; silver; and steel.

In an example, a wearable energy-conducting mesh, grid, lattice, or matrix can comprise one or more of the following: array of electroconductive members woven using a plain weave, rib weave, basket weave, twill weave, satin weave, leno weave, mock leno weave, or conan weave; array of fiber optic members woven using a plain weave, rib weave, basket weave, twill weave, satin weave, leno weave, mock leno weave; array of light-emitting fibers, threads, or yarns; array of sound-conducting members woven using a plain weave, rib weave, basket weave, twill weave, satin weave, leno weave, mock leno weave; array or mesh of electroconductive fibers; bendable fibers, threads, or yarns; bendable layer, trace, or substrate; elastic fibers, threads, or yarns; elastic layer, trace, or substrate; electroconductive fibers, threads, or yarns; electronically-functional bandage; electronically-functional tattoo; integrated array of electroconductive members; integrated array of fiber optic members; integrated array of sound-conducting members; interlaced electricity-conducting fibers, threads, or yarns; interlaced light-conducting fibers, threads, or yarns; interlaced sound-conducting fibers, threads, or yarns; light-emitting fibers, threads, or yarns; nonconductive fibers, threads, or yarns; nonconductive layer, substrate, or material; plaited fibers, threads, or yarns; sinusoidal fibers, threads, or yarns; stretchable fibers, threads, or yarns; stretchable layer, trace, or substrate; textile-based light display matrix; variable-resistance electroconductive fiber, thread, or yarn; variable-translucence fiber, thread, or yarn; water-resistant fibers, threads, or yarns; a layer or coating of metallic nanoparticles; a graphene layer; and water-resistant layer, trace, or substrate.

In an example, a wearable energy-conducting mesh, grid, lattice, or matrix can be incorporated into an article of clothing which is, in turn, worn over a body member containing a body joint. Changes in energy conducted through these pathways can be used to estimate joint motion and/or configuration. In an example, an array of energy pathways can be directly attached to a body member containing a body joint. In an example, energy pathways can be incorporated into an article of clothing or directly attached to a body member using one or more means selected from the group consisting of: adhesion, armband, article of clothing, bangle, belt, bracelet, buckle, button, clasp, clip, elastic band, elastic garment, eyewear, fabric layer, garment channel, garment pocket, gluing, hook, hook-and-eye attachment mechanism, incorporation into a bandage, incorporation into a tattoo, knitting, loop, magnetism, melting, metal fibers, nanoscale fibers, necklace, pin, polymer fibers, sewing, skin-adhesive patch, smart watch, snap, strands, strap, tape, textile channel, textile fibers, thermal bonding, tubular garment, waist band, weaving, wrist band, yarn, and zipper.

In an example, a wearable energy-conducting mesh, grid, lattice, or matrix can be incorporated into an article of clothing or clothing accessory selected from the group consisting of: an upper body garment such as a shirt, t-shirt, blouse, jacket, hoodie, sweatshirt, undershirt, brassier, girdle, blouse, or glove; a lower body garment such as a pair of pants, sweatpants, trousers, slacks, leggings, tights, underpants, pantyhose, shorts, or sock; a full-body garment such as a union suit, jump suit, pair of overalls, or dress; a clothing accessory such as shoe, boot, insole, hat, cap, headband, armband, strap, torso band, tubular accessory, wristband, other band, knee or elbow brace, back brace, knee or elbow pad, belt, bandage, electronic tattoo, or wearable patch.

In various examples, a wearable energy-conducting mesh, grid, lattice, or matrix can measure one or more joint configurations and/or motions selected from the group consisting of: eversion, extension, flexion, and/or inversion of the ankle; abduction, extension, flexion, lateral bending, and/or rotation of the spine; eversion, extension, flexion, and/or inversion of the elbow; extension and/or flexion of the finger or thumb; pronation, rotation, and/or supination of the forearm; abduction, adduction, extension, flexion, and/or rotation of the hip; extension and/or flexion of the jaw; abduction, adduction, extension, and/or flexion of the knee; eversion and/or inversion of the mid-tarsal; abduction, extension, flexion, and/or rotation of the neck; abduction, adduction, extension, flexion, and/or rotation of the shoulder; extension and/or flexion of the toe; and abduction, extension, flexion, and/or ulnar deviation or radial deviation of the wrist.

In an example, a wearable energy-conducting mesh, lattice, or matrix can span the surface of the portion of the body containing one or more body joints selected from the group consisting of: ankle, elbow, finger, forearm, hip, jaw, knee, mid-tarsal, neck, shoulder, spine, thumb, toe, and wrist. In an example, a wearable energy-conducting mesh, grid, lattice, or matrix can span the surface of a body member containing the finger and thumb. In an example, a wearable energy-conducting mesh, grid, lattice, or matrix can span the surface of a body member containing the finger, forearm, thumb and wrist. In an example, a wearable energy-conducting mesh, grid, lattice, or matrix can span the surface of a body member containing the elbow, forearm and wrist.

In an example, a wearable energy-conducting mesh, grid, lattice, or matrix can span the surface of a body member containing an elbow. In an example, a wearable energy-conducting mesh, grid, lattice, or matrix can span the surface of the body containing an elbow, forearm, shoulder and spine. In an example, a wearable energy-conducting mesh, grid, lattice, or matrix can span the surface of a body member containing a hip and knee. In an example, a wearable energy-conducting mesh, grid, lattice, or matrix can span the surface of a body member containing the spine. In an example, a wearable energy-conducting mesh, grid, lattice, or matrix can span the surface of a body member containing an ankle, mid-tarsal and toe. In an example, a wearable energy-conducting mesh, grid, lattice, or matrix can span the surface of the portion of the body containing the neck, shoulder and spine.

In an example, an article of clothing or clothing accessory can be selected from the group consisting of: a shirt, a pair of shorts, a pair of pants, and a full-body suit. In an example, an article of clothing or wearable accessory can be selected from the group consisting of: ankle band, ankle tube, arm band, arm tube, belt, bra, collar, elbow pad, elbow tube, finger tube, girdle, glove, hip pad, hoodie, knee pad, knee tube, neck band, other wearable top, pair of pants, shirt, shoe, shorts, shoulder pad, shoulder tube, sock, suit, torso band, torso tube, underwear, union suit, waist band, and waist tube. In an example, energy pathway can be connected to an article of clothing or wearable accessory by a means selected from the group consisting of: weaving, knitting, and/or sewing; adhesion and/or gluing; hook-and-eye attachment mechanisms; snaps, buckles, straps, or clips; magnetic force; integration with threads, strands, yarns, elastic bands, textile fibers, polymer fibers, metal fibers, and/or nanoscale fibers; and connection by threads, strands, yarns, elastic bands, textile fibers, polymer fibers, metal fibers, and/or nanoscale fibers.

In an example, energy flow through or from different energy pathways in a wearable energy-conducting mesh, grid, lattice, or matrix can differ in one or more parameters selected from the group consisting of: total energy; energy flow per time period; energy power; wave amplitude; wave frequency; wave phase; waveform; frequency range; spectral distribution; resistance; voltage; current; impedance; and interval pattern.

In an example, Motion Recognition Clothing™ can also include a data control unit which further comprises one or more components selected from the group consisting of: a data processing component, a data communication component, a power source, a human-to-computer user interface, a computer-to-human interface, and a digital memory. In an example, a data control unit can be temporarily detached so that the remaining wearable portion of the invention can be washed. In an example, a data processing component can perform one or more functions selected from the group consisting of: amplify sensor signals, analyze data, analyze sensor information, convert analog signals to digital signals, determine a functional relationship between signal variation and joint angle variation, estimate joint angle, filter signals, model joint configuration, record data, run software applications, run software programs, and store data in memory.

In an example, a data communication component can perform one or more functions selected from the group consisting of: transmit and receive data via Bluetooth, WiFi, Zigbee, or other wireless communication modality; transmit and receive data to and from a mobile electronic device such as a cellular phone, mobile phone, smart phone, electronic tablet; transmit and receive data to and from a separate wearable device such as a smart watch or electronically-functional eyewear; transmit and receive data to and from the internet; send and receive phone calls and electronic messages; transmit and receive data to and from a home appliance and/or home control system; and transmit and receive data to and from an implantable medical device.

In an example, Motion Recognition Clothing™ can further comprise one or more motion-related sensors selected from the group consisting of: dual-axial accelerometer, tri-axial accelerometer, other multi-axial accelerometer, gyroscope, inclinometer or tilt sensor, goniometer, GPS or other location sensor, other inertial or motion sensor, goniometer, and kinematic sensor. In an example, Motion Recognition Clothing™ can further comprise one or more electromagnetic energy sensors selected from the group consisting of: electroencephalography (EEG) sensor, peripheral neurosensor, electromyography (EMG) sensor, Hall-effect sensor, electromagnetic field sensor, electrocardiogram (ECG) sensor, cardiac monitor, EOG sensor, galvanic skin response (GSR) sensor, impedance sensor, compass, magnometer, magnetic sensor, potentiometer, variable-resistance sensor, resistive bend sensor, piezoelectric sensor, piezomechanical sensor, piezoresistive sensor, and other electromagnetic sensor. Variations discussed elsewhere in this disclosure or in priority-linked disclosures can be applied to the example in this figure where relevant.

Figure 6:
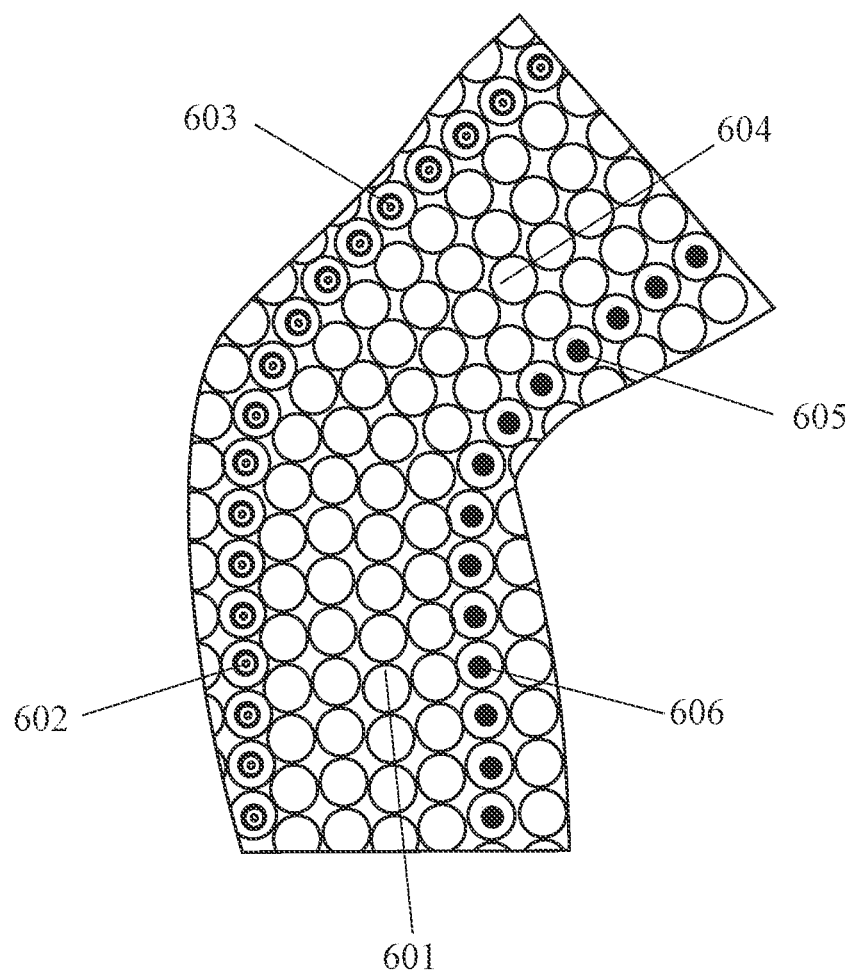
FIG. 6 shows an example with a wearable energy-conducting lattice, mesh, grid, or matrix with arcuate elements and circumferential energy pathways.

FIG. 6 shows an example of how Motion Recognition Clothing™ can be embodied in a wearable device to measure the motion and/or configuration of a body joint comprising—a wearable energy-conducting lattice, mesh, grid, or matrix that is configured to span the surface of a person's body which contains a joint, wherein this lattice, mesh, grid, or matrix further comprises: a plurality of arcuate energy-conducting elements including 6001 and 6004; a plurality of energy pathways spanning multiple arcuate energy-conducting elements which are configured to span that portion of the body in a (partial) circumferential manner; and a plurality of energy sensors including 6002 and 6003 which measure energy flow through these energy pathways, wherein data from these sensors are analyzed together using multivariate analysis in order to measure the motion and/or configuration of the body joint.

The example in FIG. 6 further comprises energy input components 6005 and 6006 which direct energy into the lattice, mesh, grid, or matrix. In an example, there can be a single energy input location rather than a plurality of energy input components. In this example, the energy pathways follow vectors which converge at a point outside the volume of the device. In this example, the energy pathways are substantially evenly-spaced along the longitudinal axis of the body member containing the joint. In this example, the arcuate elements are substantially the same in size and are circular, oval, or elliptical in shape.

In an example, the energy sensors and/or energy input components can be modular and/or moveable. In an example, energy sensors and/or energy input components can be snapped or otherwise removably-connected to the lattice, mesh, grid, or matrix at different locations in order to create different energy pathways. In an example, modular and/or moveable energy sensors and/or energy input components can allow the device to be customized to span different joints and/or be customized to a person's specific body contours. In an example, having removably-connected electronic components can also make it easier to wash the device.

In an example, a plurality of wearable energy pathways can form a mesh, grid, lattice, or matrix with square, rectangular, rhomboid, or trapezoid shaped elements. In an example, a plurality of wearable energy pathways can form a mesh, grid, lattice, or matrix with interlocking and/or repeating square, rectangular, rhomboid, or trapezoid shaped elements. In an example, a plurality of wearable energy pathways can form a mesh, grid, lattice, or matrix with diamond-shaped elements. In an example, a plurality of wearable energy pathways can form a mesh, grid, lattice, or matrix with interlocking and/or repeating diamond-shaped elements. In an example, a plurality of wearable energy pathways can form a hexagonal mesh, grid, lattice, or matrix (e.g. a honeycomb mesh or grid).

In an example, a plurality of wearable energy pathways can form a mesh, grid, lattice, or matrix with a chain of loops. In an example, a plurality of wearable energy pathways can form a mesh, grid, lattice, or matrix with a chain of knitted loops. In an example, a plurality of wearable energy pathways can form a mesh, grid, lattice, or matrix with circular or elliptical elements. In an example, a plurality of wearable energy pathways can form a mesh, grid, lattice, or matrix with interlocking and/or repeating circular or elliptical elements. In an example, a plurality of wearable energy pathways can form a mesh, grid, lattice, or matrix with triangular elements. In an example, a plurality of wearable energy pathways can form a mesh, grid, lattice, or matrix with interlocking and/or repeating triangular elements.

In an example, a plurality of wearable energy pathways in a wearable energy-conducting mesh, grid, lattice, or matrix can be straight. In an example, a plurality of wearable energy pathways in a wearable energy-conducting mesh, grid, lattice, or matrix can be sinusoidal. In an example, a plurality of wearable energy pathways in a wearable energy-conducting mesh, grid, lattice, or matrix can have saw-tooth wave or square-wave shapes. In an example, a plurality of wearable energy pathways in a wearable energy-conducting mesh, grid, lattice, or matrix can have conic section shapes, wherein examples of conic sections include circles, ellipses, parabolas, and hyperbolas. In an example, a plurality of wearable energy pathways in a wearable energy-conducting mesh, grid, lattice, or matrix can have helical or spiral shapes.

In an example, a wearable energy-conducting mesh, grid, lattice, or matrix can comprise square elements, rectangular elements, diamond elements, rhomboid elements, parallelogram elements, trapezoidal elements, triangular elements, hexagonal elements, circular elements, or elliptical elements. In an example, a wearable energy-conducting mesh, grid, lattice, or matrix can comprise interlocking and/or repeating square elements, rectangular elements, diamond elements, rhomboid elements, parallelogram elements, trapezoidal elements, triangular elements, hexagonal elements, circular elements, or elliptical elements.

In an example, a wearable energy-conducting mesh, grid, lattice, or matrix can comprise a repeating pattern of quadrilateral (e.g. square, rectangular, trapezoidal, parallelogram, or diamond shaped) elements. In an example, a wearable energy-conducting mesh, grid, lattice, or matrix can comprise a repeating pattern of hexagonal elements (e.g. a honeycomb mesh). In an example, a wearable energy-conducting mesh, grid, lattice, or matrix can comprise a repeating pattern of arcuate elements created by parallel, different-phase sinusoidal curves. In an example, a wearable energy-conducting mesh, grid, lattice, or matrix can comprise a repeating pattern of arcuate elements created by intersecting sinusoidal curves.

In an example, geometric relationships between energy pathways in a wearable energy-conducting mesh, grid, lattice, or matrix can be selected from the group consisting of: substantially parallel; separated by a substantially-constant distance; separated by a substantially-constant number of radial degrees of the cross-sectional perimeter of a body member; separated by a substantially-constant percentage of the cross-sectional perimeter of a body member; forming vectors which intersect in 3D space at a right angle; substantially-parallel as they span a distal portion of a joint and diverging as they span a proximal portion of a joint; substantially-parallel as they span a proximal portion of a joint and diverging as they span a distal portion of a joint; substantially perpendicular; intersecting at an acute angle; forming vectors which intersect in 3D space at an acute angle; substantially diagonal to each other; plaited together; woven together; braided together; combining to form a 3D lattice, mesh, or grid; differing in length; nested; forming a rainbow arc configuration; radial vectors with a common point of convergence; straight vectors with a common convergence point; and arcuate elements with a common convergence point.

In an example, energy pathways in a wearable energy-conducting mesh, grid, lattice, or matrix can differ in the angles at which they span the longitudinal axis of a body member which contains a body joint. In an example, different energy pathways in a wearable energy-conducting mesh, grid, lattice, or matrix can span a body joint at different angles. In an example, having different energy pathways span a body joint at different angles can be especially useful for measuring the motion and/or configuration of ball-and-socket or other complex motion joints. In an example, energy pathways in a wearable energy-conducting mesh, grid, lattice, or matrix can have longitudinal axes which intersect each other in an orthogonal manner. In an example, energy pathways in a wearable energy-conducting mesh, grid, lattice, or matrix can have longitudinal axes which intersect each other at acute angles.

In an example, energy pathways in a wearable energy-conducting mesh, grid, lattice, or matrix can form interpathway areas which, when projected from 3D space onto a 2D plane, are squares or rectangles. In an example, one or more aspects of the geometric relationship between energy pathways in a wearable energy-conducting mesh, grid, lattice, or matrix can be selected from the group consisting of: substantially parallel; separated by a substantially-constant distance; intersecting at an acute angle; forming vectors which intersect in 3D space at an acute angle; combining to form a 3D mesh, grid, lattice, or matrix; differing in length; substantially concentric; nested; differing in diameter; knitted together in loops; and tangential.

In an example, one or more aspects of the geometric relationship between energy pathways in a wearable energy-conducting mesh, grid, lattice, or matrix can be selected from the group consisting of: substantially perpendicular; intersecting at a right angle; intersecting at an acute angle; defining square-shaped spaces (when projected onto a 2D plane) as they intersect; defining rhomboid-shaped spaces (when projected onto a 2D plane) as they intersect; defining trapezoid-shaped spaces (when projected onto a 2D plane) as they intersect; plaited together; woven together; braided together; combining to form a 3D mesh, grid, lattice, or matrix; overlapping; and tangential.

In an example, energy pathways in a wearable energy-conducting mesh, grid, lattice, or matrix can have substantially straight configurations when a joint is fully extended. In an example, energy pathways in a wearable energy-conducting mesh, grid, lattice, or matrix can have arcuate shapes, even when a joint is fully extended. In an example, a wearable energy-conducting mesh, grid, lattice, or matrix can have a repeating pattern or waveform selected from the group consisting of: simple sinusoidal wave; composite sinusoidal wave; saw-tooth wave or zigzag; and square wave. In an example, an energy pathway can have a shape which is a conic section. In an example, an energy pathway can have a shape which is a spiral or helix. In an example, an energy pathway can have a shape which is a chain of loops.

In an example, the flows of energy through energy pathways in a wearable energy-conducting mesh, grid, lattice, or matrix can be independent and/or separate. In an example, the flows of energy through energy pathways in a wearable energy-conducting mesh, grid, lattice, or matrix can interact and/or combine with each other. In an example, energy pathways in a wearable energy-conducting mesh, grid, lattice, or matrix can be in electromagnetic communication with each other.

In an example, energy pathways in a wearable energy-conducting mesh, grid, lattice, or matrix can differ by one or more parameters selected from the group consisting of: the angle at which they span the body joint; length; longitudinal curvature or convolution; longitudinal waveform; flexibility; elasticity; electrical resistance or impedance; transparency; and cross-sectional shape. In an example, energy pathways in a wearable energy-conducting mesh, grid, lattice, or matrix can differ in the angles at which they span the body member. In an example, energy pathways in a wearable energy-conducting mesh, grid, lattice, or matrix can differ in length. In an example, energy pathways in a wearable energy-conducting mesh, grid, lattice, or matrix can differ in longitudinal curvature or convolution.

In an example, energy pathways in a wearable energy-conducting mesh, grid, lattice, or matrix can differ in flexibility. In an example, energy pathways in a wearable energy-conducting mesh, grid, lattice, or matrix can differ in elasticity. In an example, energy pathways in a wearable energy-conducting mesh, grid, lattice, or matrix can differ in electrical resistance or impedance. In an example, energy pathways in a wearable energy-conducting mesh, grid, lattice, or matrix can differ in cross-sectional shape.

In an example, energy pathways in a wearable energy-conducting mesh, grid, lattice, or matrix can be woven together in a substantially-perpendicular manner to form a textile. In an example, energy pathways in a wearable energy-conducting mesh, grid, lattice, or matrix can be knitted together. In an example, energy pathways in a wearable energy-conducting mesh, grid, lattice, or matrix can be knitted together in a chain of loops. In an example, energy pathways in a wearable energy-conducting mesh, grid, lattice, or matrix can be plaited, knitted, woven together, or braided together.

In an example, the relationship between energy flow in an energy pathway and the configuration of a body joint spanned by that energy pathway can be nonlinear and/or stochastic. In an example, data from multiple energy pathways can be jointly analyzed using one or more statistical methods selected from the group consisting of: multivariate linear regression or least squares estimation; factor analysis; Fourier Transformation; mean; median; multivariate logit; principal components analysis; spline function; auto-regression; carlavian curve analysis, centroid analysis; correlation; covariance; decision tree analysis; kinematic modeling; Kalman filter; linear discriminant analysis; linear transform; logarithmic function; logit analysis; Markov model; multivariate parametric classifiers; non-linear programming; orthogonal transformation; pattern recognition; random forest analysis; spectroscopic analysis; variance; artificial neural network; Bayesian filter or other Bayesian statistical method; chi-squared; eigenvalue decomposition; logit model; machine learning; power spectral density; power spectrum analysis; probit model; and time-series analysis.

In an example, repeated or cyclical patterns of movement such as walking or running can be identified and analyzed using Fourier analysis. In an example, the speed of repeated movement cycles can influence the functional relationship between the flow of energy through an energy pathway and the angle of a joint. In an example, the speed of repeated cycles can especially influence this functional relationship at the end-points of a cycle wherein joint movement reverses direction. In an example, analyzing and identifying the speed of repeated or cyclical patterns of movement using Fourier transform methods can improve the accuracy of measuring joint motion and configuration.

In an example, data from different energy pathways in a wearable energy-conducting mesh, grid, lattice, or matrix can be given different weights during different portions of the joint range of motion in order to improve accuracy and reduce error in the measurement of the motion and/or configuration of that joint. In an example, data from different energy pathways in a wearable energy-conducting mesh, grid, lattice, or matrix can be given different weights during different directions of joint motion (e.g. flexion vs. extension) in order to improve accuracy and reduce error in the measurement of the motion and/or configuration of that joint. In an example, data from different energy pathways in a wearable energy-conducting mesh, grid, lattice, or matrix can be given different weights during different movement speeds (e.g. fast movement vs. slow movement) of joint motion in order to improve accuracy and reduce error in the measurement of the motion and/or configuration of that joint.

In an example, changes in the flows of electromagnetic energy can be measured by one or more parameters selected from the group consisting of: voltage, resistance, impedance, amperage, current, phase, and wave pattern. In an example, an electromagnetic energy pathway can be comprised of electroconductive fibers, yarns, threads, strands, substrates, layers, or textiles. In an example, an electromagnetic energy sensor can be selected from the group consisting of: voltmeter, impedance sensor, magnetic field sensor, piezoelectric sensor, piezomechanical sensor, potentiometer, resistive bend sensor, variable-resistance sensor, electromyography (EMG) sensor, and Hall-effect sensor.

In an example, electromagnetic energy can be directed into an energy pathway at a first location and electromagnetic energy from the energy pathway can be measured from the energy pathway at a second location. In an example, electromagnetic energy can be directed into a wearable mesh, grid, lattice, or matrix of conductive pathways at a first location and received out from the mesh, grid, lattice, or matrix at a second location. In an example, electromagnetic energy can be directed into a wearable mesh, grid, lattice, or matrix of conductive pathways at a first vertex (or juncture of energy-conducting pathways) and received out from the mesh, grid, lattice, or matrix at a second vertex (or juncture of energy-conducting pathways). In an example, electromagnetic energy can be directed into a wearable mesh, grid, lattice, or matrix of conductive pathways at a first set of multiple location, vertexes, and/or pathway junctures and received out from the mesh, grid, lattice, or matrix at a second set of multiple location, vertexes, and/or pathway junctures In an example, electromagnetic energy can be transmitted into an energy pathway at a first location and electromagnetic energy from the energy pathway can be measured from the energy pathway at a second location. In an example, electromagnetic energy can be transmitted into a wearable mesh, grid, lattice, or matrix of conductive pathways at a first location and measured from the mesh, grid, lattice, or matrix at a second location. In an example, electromagnetic energy can be transmitted into a wearable mesh, grid, lattice, or matrix of conductive pathways at a first vertex (or juncture of energy-conducting pathways) and measured from the mesh, grid, lattice, or matrix at a second vertex (or juncture of energy-conducting pathways). In an example, electromagnetic energy can be transmitted into a wearable mesh, grid, lattice, or matrix of conductive pathways at a first set of multiple location, vertexes, and/or pathway junctures and measured from the mesh, grid, lattice, or matrix at a second set of multiple location, vertexes, and/or pathway junctures In an example, wearable energy pathways in a wearable mesh, grid, lattice, or matrix can comprise non-conductive or less-conductive fibers, traces, yarns, strands, or textiles which are coated, impregnated, or otherwise integrated with conductive material or particles. In an example, a non-conductive or less-conductive fiber, trace, yarn, strand, or textile can be selected from the group consisting of: acetate, acrylic, cotton, denim, elastane, Kevlar, latex, linen, Lycra, neoprene, nylon, nylon, polyester, wool, silicon rubber, silk, spandex, Danconn or rayon. In an example, conductive material or particles used for coating or impregnation can be selected from the group consisting of: aluminum or aluminum alloy; carbon nanotubes, graphene, or other carbon-based material; magnesium; ceramic particles; copper or copper alloy; gold; nickel; polyaniline; silver; and steel.

In an example, a wearable energy-conducting mesh, grid, lattice, or matrix can comprise one or more of the following: array of electroconductive members woven using a plain weave, rib weave, basket weave, twill weave, satin weave, leno weave, mock leno weave, or conan weave; array of fiber optic members woven using a plain weave, rib weave, basket weave, twill weave, satin weave, leno weave, mock leno weave; array of light-emitting fibers, threads, or yarns; array of sound-conducting members woven using a plain weave, rib weave, basket weave, twill weave, satin weave, leno weave, mock leno weave; array or mesh of electroconductive fibers; bendable fibers, threads, or yarns; bendable layer, trace, or substrate; elastic fibers, threads, or yarns; elastic layer, trace, or substrate; electroconductive fibers, threads, or yarns; electronically-functional bandage; electronically-functional tattoo; integrated array of electroconductive members; integrated array of fiber optic members; integrated array of sound-conducting members; interlaced electricity-conducting fibers, threads, or yarns; interlaced light-conducting fibers, threads, or yarns; interlaced sound-conducting fibers, threads, or yarns; light-emitting fibers, threads, or yarns; nonconductive fibers, threads, or yarns; nonconductive layer, substrate, or material; plaited fibers, threads, or yarns; sinusoidal fibers, threads, or yarns; stretchable fibers, threads, or yarns; stretchable layer, trace, or substrate; textile-based light display matrix; variable-resistance electroconductive fiber, thread, or yarn; variable-translucence fiber, thread, or yarn; water-resistant fibers, threads, or yarns; a layer or coating of metallic nanoparticles; a graphene layer; and water-resistant layer, trace, or substrate.

In an example, a wearable energy-conducting mesh, grid, lattice, or matrix can be incorporated into an article of clothing which is, in turn, worn over a body member containing a body joint. Changes in energy conducted through these pathways can be used to estimate joint motion and/or configuration. In an example, an array of energy pathways can be directly attached to a body member containing a body joint. In an example, energy pathways can be incorporated into an article of clothing or directly attached to a body member using one or more means selected from the group consisting of: adhesion, armband, article of clothing, bangle, belt, bracelet, buckle, button, clasp, clip, elastic band, elastic garment, eyewear, fabric layer, garment channel, garment pocket, gluing, hook, hook-and-eye attachment mechanism, incorporation into a bandage, incorporation into a tattoo, knitting, loop, magnetism, melting, metal fibers, nanoscale fibers, necklace, pin, polymer fibers, sewing, skin-adhesive patch, smart watch, snap, strands, strap, tape, textile channel, textile fibers, thermal bonding, tubular garment, waist band, weaving, wrist band, yarn, and zipper.

In an example, a wearable energy-conducting mesh, grid, lattice, or matrix can be incorporated into an article of clothing or clothing accessory selected from the group consisting of: an upper body garment such as a shirt, t-shirt, blouse, jacket, hoodie, sweatshirt, undershirt, brassier, girdle, blouse, or glove; a lower body garment such as a pair of pants, sweatpants, trousers, slacks, leggings, tights, underpants, pantyhose, shorts, or sock; a full-body garment such as a union suit, jump suit, pair of overalls, or dress; a clothing accessory such as shoe, boot, insole, hat, cap, headband, armband, strap, torso band, tubular accessory, wristband, other band, knee or elbow brace, back brace, knee or elbow pad, belt, bandage, electronic tattoo, or wearable patch.

In various examples, a wearable energy-conducting mesh, grid, lattice, or matrix can measure one or more joint configurations and/or motions selected from the group consisting of: eversion, extension, flexion, and/or inversion of the ankle; abduction, extension, flexion, lateral bending, and/or rotation of the spine; eversion, extension, flexion, and/or inversion of the elbow; extension and/or flexion of the finger or thumb; pronation, rotation, and/or supination of the forearm; abduction, adduction, extension, flexion, and/or rotation of the hip; extension and/or flexion of the jaw; abduction, adduction, extension, and/or flexion of the knee; eversion and/or inversion of the mid-tarsal; abduction, extension, flexion, and/or rotation of the neck; abduction, adduction, extension, flexion, and/or rotation of the shoulder; extension and/or flexion of the toe; and abduction, extension, flexion, and/or ulnar deviation or radial deviation of the wrist.

In an example, a wearable energy-conducting mesh, grid, lattice, or matrix can span the surface of the portion of the body containing one or more body joints selected from the group consisting of: ankle, elbow, finger, forearm, hip, jaw, knee, mid-tarsal, neck, shoulder, spine, thumb, toe, and wrist. In an example, a wearable energy-conducting mesh, grid, lattice, or matrix can span the surface of a body member containing the finger and thumb. In an example, a wearable energy-conducting mesh, grid, lattice, or matrix can span the surface of a body member containing the finger, forearm, thumb and wrist. In an example, a wearable energy-conducting mesh, grid, lattice, or matrix can span the surface of a body member containing the elbow, forearm and wrist.

In an example, a wearable energy-conducting mesh, grid, lattice, or matrix can span the surface of a body member containing an elbow. In an example, a wearable energy-conducting mesh, grid, lattice, or matrix can span the surface of the body containing an elbow, forearm, shoulder and spine. In an example, a wearable energy-conducting mesh, grid, lattice, or matrix can span the surface of a body member containing a hip and knee. In an example, a wearable energy-conducting mesh, grid, lattice, or matrix can span the surface of a body member containing the spine. In an example, a wearable energy-conducting mesh, grid, lattice, or matrix can span the surface of a body member containing an ankle, mid-tarsal and toe. In an example, a wearable energy-conducting mesh, grid, lattice, or matrix can span the surface of the portion of the body containing the neck, shoulder and spine.

In an example, an article of clothing or clothing accessory can be selected from the group consisting of: a shirt, a pair of shorts, a pair of pants, and a full-body suit. In an example, an article of clothing or wearable accessory can be selected from the group consisting of: ankle band, ankle tube, arm band, arm tube, belt, bra, collar, elbow pad, elbow tube, finger tube, girdle, glove, hip pad, hoodie, knee pad, knee tube, neck band, other wearable top, pair of pants, shirt, shoe, shorts, shoulder pad, shoulder tube, sock, suit, torso band, torso tube, underwear, union suit, waist band, and waist tube. In an example, energy pathway can be connected to an article of clothing or wearable accessory by a means selected from the group consisting of: weaving, knitting, and/or sewing; adhesion and/or gluing; hook-and-eye attachment mechanisms; snaps, buckles, straps, or clips; magnetic force; integration with threads, strands, yarns, elastic bands, textile fibers, polymer fibers, metal fibers, and/or nanoscale fibers; and connection by threads, strands, yarns, elastic bands, textile fibers, polymer fibers, metal fibers, and/or nanoscale fibers.

In an example, energy flow through or from different energy pathways in a wearable energy-conducting mesh, grid, lattice, or matrix can differ in one or more parameters selected from the group consisting of: total energy; energy flow per time period; energy power; wave amplitude; wave frequency; wave phase; waveform; frequency range; spectral distribution; resistance; voltage; current; impedance; and interval pattern.

In an example, Motion Recognition Clothing™ can also include a data control unit which further comprises one or more components selected from the group consisting of: a data processing component, a data communication component, a power source, a human-to-computer user interface, a computer-to-human interface, and a digital memory. In an example, a data control unit can be temporarily detached so that the remaining wearable portion of the invention can be washed. In an example, a data processing component can perform one or more functions selected from the group consisting of: amplify sensor signals, analyze data, analyze sensor information, convert analog signals to digital signals, determine a functional relationship between signal variation and joint angle variation, estimate joint angle, filter signals, model joint configuration, record data, run software applications, run software programs, and store data in memory.

In an example, a data communication component can perform one or more functions selected from the group consisting of: transmit and receive data via Bluetooth, WiFi, Zigbee, or other wireless communication modality; transmit and receive data to and from a mobile electronic device such as a cellular phone, mobile phone, smart phone, electronic tablet; transmit and receive data to and from a separate wearable device such as a smart watch or electronically-functional eyewear; transmit and receive data to and from the internet; send and receive phone calls and electronic messages; transmit and receive data to and from a home appliance and/or home control system; and transmit and receive data to and from an implantable medical device.

In an example, Motion Recognition Clothing™ can further comprise one or more motion-related sensors selected from the group consisting of: dual-axial accelerometer, tri-axial accelerometer, other multi-axial accelerometer, gyroscope, inclinometer or tilt sensor, goniometer, GPS or other location sensor, other inertial or motion sensor, goniometer, and kinematic sensor. In an example, Motion Recognition Clothing™ can further comprise one or more electromagnetic energy sensors selected from the group consisting of: electroencephalography (EEG) sensor, peripheral neurosensor, electromyography (EMG) sensor, Hall-effect sensor, electromagnetic field sensor, electrocardiogram (ECG) sensor, cardiac monitor, EOG sensor, galvanic skin response (GSR) sensor, impedance sensor, compass, magnetometer, magnetic sensor, potentiometer, variable-resistance sensor, resistive bend sensor, piezoelectric sensor, piezomechanical sensor, piezoresistive sensor, and other electromagnetic sensor. Variations discussed elsewhere in this disclosure or in priority-linked disclosures can be applied to the example in this figure where relevant.

Figure 7:
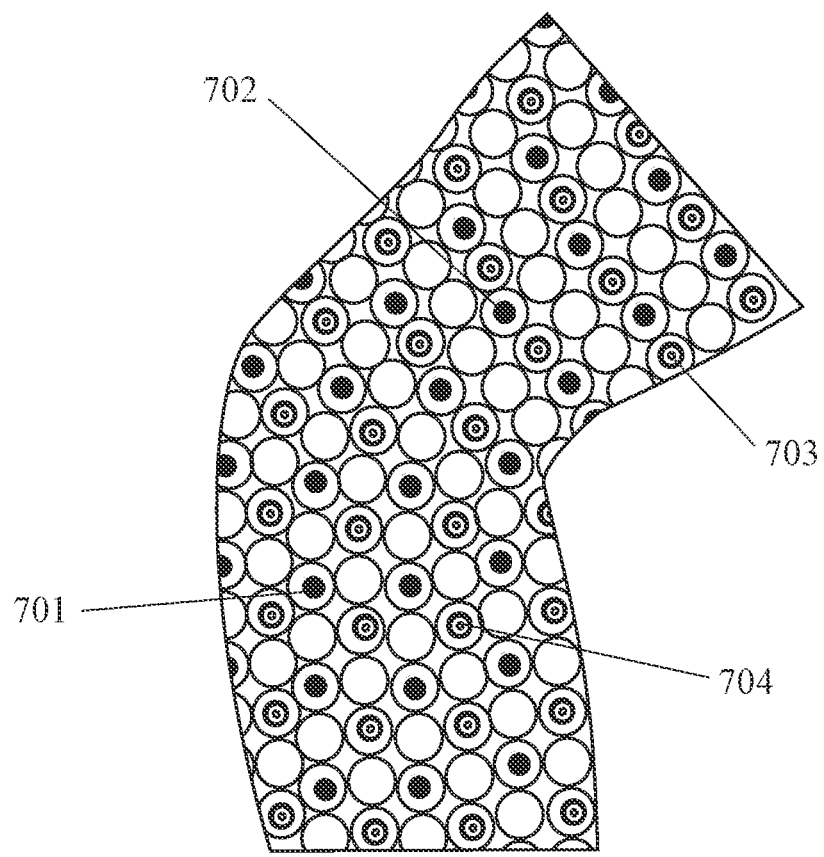
FIG. 7 shows an example with a wearable energy-conducting lattice, mesh, grid, or matrix with arcuate elements and multi-directional energy pathways.

FIG. 7 shows an example of how Motion Recognition Clothing™ can be embodied in a wearable device to measure the motion and/or configuration of a body joint comprising—a wearable energy-conducting lattice, mesh, grid, or matrix that is configured to span the surface of a person's body which contains a joint, wherein this lattice, mesh, grid, or matrix further comprises: a plurality of arcuate energy-conducting elements; a plurality of energy pathways spanning multiple arcuate energy-conducting elements; and a plurality of energy sensors including 703 and 704 which measure energy flow through these energy pathways, wherein data from these sensors are analyzed together using multivariate analysis in order to measure the motion and/or configuration of the body joint.

The example in FIG. 7 further comprises energy input components 701 and 702 which direct energy into the lattice, mesh, grid, or matrix. In an example, there can be a single energy input location rather than a plurality of energy input components. In this example, the arcuate elements are substantially the same in size and are circular, oval, or elliptical in shape. In an example, the energy sensors and/or energy input components can be modular and/or moveable. In an example, energy sensors and/or energy input components can be snapped or otherwise removably-connected to the lattice, mesh, grid, or matrix at different locations in order to create different energy pathways. In an example, modular and/or moveable energy sensors and/or energy input components can allow the device to be customized to span different joints and/or be customized to a person's specific body contours. In an example, having removably-connected electronic components can also make it easier to wash the device.

In an example, an energy pathway can have a shape comprising a repeating waveform selected from the group consisting of: simple sinusoidal wave; composite sinusoidal wave; saw-tooth wave or zigzag; and square wave. In an example, an energy pathway can have a shape which is a conic section. In an example, an energy pathway can have a shape which is a spiral or helix. In an example, an energy pathway can have a shape which is a chain of loops.

In an example, first and second energy pathways which span a body member which contains a body joint can differ in longitudinal curvature or convolution. In an example, combined multivariate analysis of data from both the first and second energy pathways can provide more accurate measurement of body joint motion than data from either the first energy pathway or the second energy pathway alone. In an example, an energy pathway with a sinusoidal, zigzag or sawtooth, or other repeated wave shape can have a higher curvature or convolution if it has a waveform with a larger amplitude or higher wave frequency. In an example, data from a highly curved or convoluted energy pathway can provide more accurate measurement of body joint motion over a first range of motion and data from a less curved or convoluted energy pathway can provide more accurate measurement of body joint motion over a second range of motion. When analyzed together, data from the highly curved or convoluted and the less curved or convoluted energy pathways reduce error in measuring the full range of joint motion.

In an example, a plurality of wearable energy pathways can form a mesh, grid, lattice, or matrix with square, rectangular, rhomboid, or trapezoid shaped elements. In an example, a plurality of wearable energy pathways can form a mesh, grid, lattice, or matrix with interlocking and/or repeating square, rectangular, rhomboid, or trapezoid shaped elements. In an example, a plurality of wearable energy pathways can form a mesh, grid, lattice, or matrix with diamond-shaped elements. In an example, a plurality of wearable energy pathways can form a mesh, grid, lattice, or matrix with interlocking and/or repeating diamond-shaped elements. In an example, a plurality of wearable energy pathways can form a hexagonal mesh, grid, lattice, or matrix (e.g. a honeycomb mesh or grid).

In an example, a plurality of wearable energy pathways can form a mesh, grid, lattice, or matrix with a chain of loops. In an example, a plurality of wearable energy pathways can form a mesh, grid, lattice, or matrix with a chain of knitted loops. In an example, a plurality of wearable energy pathways can form a mesh, grid, lattice, or matrix with circular or elliptical elements. In an example, a plurality of wearable energy pathways can form a mesh, grid, lattice, or matrix with interlocking and/or repeating circular or elliptical elements. In an example, a plurality of wearable energy pathways can form a mesh, grid, lattice, or matrix with triangular elements. In an example, a plurality of wearable energy pathways can form a mesh, grid, lattice, or matrix with interlocking and/or repeating triangular elements.

In an example, a plurality of wearable energy pathways in a wearable energy-conducting mesh, grid, lattice, or matrix can be straight. In an example, a plurality of wearable energy pathways in a wearable energy-conducting mesh, grid, lattice, or matrix can be sinusoidal. In an example, a plurality of wearable energy pathways in a wearable energy-conducting mesh, grid, lattice, or matrix can have saw-tooth wave or square-wave shapes. In an example, a plurality of wearable energy pathways in a wearable energy-conducting mesh, grid, lattice, or matrix can have conic section shapes, wherein examples of conic sections include circles, ellipses, parabolas, and hyperbolas. In an example, a plurality of wearable energy pathways in a wearable energy-conducting mesh, grid, lattice, or matrix can have helical or spiral shapes.

In an example, a wearable energy-conducting mesh, grid, lattice, or matrix can comprise square elements, rectangular elements, diamond elements, rhomboid elements, parallelogram elements, trapezoidal elements, triangular elements, hexagonal elements, circular elements, or elliptical elements. In an example, a wearable energy-conducting mesh, grid, lattice, or matrix can comprise interlocking and/or repeating square elements, rectangular elements, diamond elements, rhomboid elements, parallelogram elements, trapezoidal elements, triangular elements, hexagonal elements, circular elements, or elliptical elements.

In an example, a wearable energy-conducting mesh, grid, lattice, or matrix can comprise a repeating pattern of quadrilateral (e.g. square, rectangular, trapezoidal, parallelogram, or diamond shaped) elements. In an example, a wearable energy-conducting mesh, grid, lattice, or matrix can comprise a repeating pattern of hexagonal elements (e.g. a honeycomb mesh). In an example, a wearable energy-conducting mesh, grid, lattice, or matrix can comprise a repeating pattern of arcuate elements created by parallel, different-phase sinusoidal curves. In an example, a wearable energy-conducting mesh, grid, lattice, or matrix can comprise a repeating pattern of arcuate elements created by intersecting sinusoidal curves.

In an example, geometric relationships between energy pathways in a wearable energy-conducting mesh, grid, lattice, or matrix can be selected from the group consisting of: substantially parallel; separated by a substantially-constant distance; separated by a substantially-constant number of radial degrees of the cross-sectional perimeter of a body member; separated by a substantially-constant percentage of the cross-sectional perimeter of a body member; forming vectors which intersect in 3D space at a right angle; substantially-parallel as they span a distal portion of a joint and diverging as they span a proximal portion of a joint; substantially-parallel as they span a proximal portion of a joint and diverging as they span a distal portion of a joint; substantially perpendicular; intersecting at an acute angle; forming vectors which intersect in 3D space at an acute angle; substantially diagonal to each other; plaited together; woven together; braided together; combining to form a 3D lattice, mesh, or grid; differing in length; nested; forming a rainbow arc configuration; radial vectors with a common point of convergence; straight vectors with a common convergence point; and arcuate elements with a common convergence point.

In an example, energy pathways in a wearable energy-conducting mesh, grid, lattice, or matrix can differ in the angles at which they span the longitudinal axis of a body member which contains a body joint. In an example, different energy pathways in a wearable energy-conducting mesh, grid, lattice, or matrix can span a body joint at different angles. In an example, having different energy pathways span a body joint at different angles can be especially useful for measuring the motion and/or configuration of ball-and-socket or other complex motion joints. In an example, energy pathways in a wearable energy-conducting mesh, grid, lattice, or matrix can have longitudinal axes which intersect each other in an orthogonal manner. In an example, energy pathways in a wearable energy-conducting mesh, grid, lattice, or matrix can have longitudinal axes which intersect each other at acute angles.

In an example, energy pathways in a wearable energy-conducting mesh, grid, lattice, or matrix can form inter-pathway areas which, when projected from 3D space onto a 2D plane, are squares or rectangles. In an example, one or more aspects of the geometric relationship between energy pathways in a wearable energy-conducting mesh, grid, lattice, or matrix can be selected from the group consisting of: substantially parallel; separated by a substantially-constant distance; intersecting at an acute angle; forming vectors which intersect in 3D space at an acute angle; combining to form a 3D mesh, grid, lattice, or matrix; differing in length; substantially concentric; nested; differing in diameter; knitted together in loops; and tangential.

In an example, one or more aspects of the geometric relationship between energy pathways in a wearable energy-conducting mesh, grid, lattice, or matrix can be selected from the group consisting of: substantially perpendicular; intersecting at a right angle; intersecting at an acute angle; defining square-shaped spaces (when projected onto a 2D plane) as they intersect; defining rhomboid-shaped spaces (when projected onto a 2D plane) as they intersect; defining trapezoid-shaped spaces (when projected onto a 2D plane) as they intersect; plaited together; woven together; braided together; combining to form a 3D mesh, grid, lattice, or matrix; overlapping; and tangential.

In an example, energy pathways in a wearable energy-conducting mesh, grid, lattice, or matrix can have substantially straight configurations when a joint is fully extended. In an example, energy pathways in a wearable energy-conducting mesh, grid, lattice, or matrix can have arcuate shapes, even when a joint is fully extended. In an example, a wearable energy-conducting mesh, grid, lattice, or matrix can have a repeating pattern or waveform selected from the group consisting of: simple sinusoidal wave; composite sinusoidal wave; saw-tooth wave or zigzag; and square wave. In an example, an energy pathway can have a shape which is a conic section. In an example, an energy pathway can have a shape which is a spiral or helix. In an example, an energy pathway can have a shape which is a chain of loops.

In an example, the flows of energy through energy pathways in a wearable energy-conducting mesh, grid, lattice, or matrix can be independent and/or separate. In an example, the flows of energy through energy pathways in a wearable energy-conducting mesh, grid, lattice, or matrix can interact and/or combine with each other. In an example, energy pathways in a wearable energy-conducting mesh, grid, lattice, or matrix can be in electromagnetic communication with each other.

In an example, energy pathways in a wearable energy-conducting mesh, grid, lattice, or matrix can differ by one or more parameters selected from the group consisting of: the angle at which they span the body joint; length; longitudinal curvature or convolution; longitudinal waveform; flexibility; elasticity; electrical resistance or impedance; transparency; and cross-sectional shape. In an example, energy pathways in a wearable energy-conducting mesh, grid, lattice, or matrix can differ in the angles at which they span the body member. In an example, energy pathways in a wearable energy-conducting mesh, grid, lattice, or matrix can differ in length. In an example, energy pathways in a wearable energy-conducting mesh, grid, lattice, or matrix can differ in longitudinal curvature or convolution.

In an example, energy pathways in a wearable energy-conducting mesh, grid, lattice, or matrix can differ in flexibility. In an example, energy pathways in a wearable energy-conducting mesh, grid, lattice, or matrix can differ in elasticity. In an example, energy pathways in a wearable energy-conducting mesh, grid, lattice, or matrix can differ in electrical resistance or impedance. In an example, energy pathways in a wearable energy-conducting mesh, grid, lattice, or matrix can differ in cross-sectional shape.

In an example, energy pathways in a wearable energy-conducting mesh, grid, lattice, or matrix can be woven together in a substantially-perpendicular manner to form a textile. In an example, energy pathways in a wearable energy-conducting mesh, grid, lattice, or matrix can be knitted together. In an example, energy pathways in a wearable energy-conducting mesh, grid, lattice, or matrix can be knitted together in a chain of loops. In an example, energy pathways in a wearable energy-conducting mesh, grid, lattice, or matrix can be plaited, knitted, woven together, or braided together.

In an example, the relationship between energy flow in an energy pathway and the configuration of a body joint spanned by that energy pathway can be nonlinear and/or stochastic. In an example, data from multiple energy pathways can be jointly analyzed using one or more statistical methods selected from the group consisting of: multivariate linear regression or least squares estimation; factor analysis; Fourier Transformation; mean; median; multivariate logit; principal components analysis; spline function; auto-regression; carlavian curve analysis, centroid analysis; correlation; covariance; decision tree analysis; kinematic modeling; Kalman filter; linear discriminant analysis; linear transform; logarithmic function; logit analysis; Markov model; multivariate parametric classifiers; non-linear programming; orthogonal transformation; pattern recognition; random forest analysis; spectroscopic analysis; variance; artificial neural network; Bayesian filter or other Bayesian statistical method; chi-squared; eigenvalue decomposition; logit model; machine learning; power spectral density; power spectrum analysis; probit model; and time-series analysis.

In an example, repeated or cyclical patterns of movement such as walking or running can be identified and analyzed using Fourier analysis. In an example, the speed of repeated movement cycles can influence the functional relationship between the flow of energy through an energy pathway and the angle of a joint. In an example, the speed of repeated cycles can especially influence this functional relationship at the end-points of a cycle wherein joint movement reverses direction. In an example, analyzing and identifying the speed of repeated or cyclical patterns of movement using Fourier transform methods can improve the accuracy of measuring joint motion and configuration.

In an example, data from different energy pathways in a wearable energy-conducting mesh, grid, lattice, or matrix can be given different weights during different portions of the joint range of motion in order to improve accuracy and reduce error in the measurement of the motion and/or configuration of that joint. In an example, data from different energy pathways in a wearable energy-conducting mesh, grid, lattice, or matrix can be given different weights during different directions of joint motion (e.g. flexion vs. extension) in order to improve accuracy and reduce error in the measurement of the motion and/or configuration of that joint. In an example, data from different energy pathways in a wearable energy-conducting mesh, grid, lattice, or matrix can be given different weights during different movement speeds (e.g. fast movement vs. slow movement) of joint motion in order to improve accuracy and reduce error in the measurement of the motion and/or configuration of that joint.

In an example, changes in the flows of electromagnetic energy can be measured by one or more parameters selected from the group consisting of: voltage, resistance, impedance, amperage, current, phase, and wave pattern. In an example, an electromagnetic energy pathway can be comprised of electroconductive fibers, yarns, threads, strands, substrates, layers, or textiles. In an example, an electromagnetic energy sensor can be selected from the group consisting of: voltmeter, impedance sensor, magnetic field sensor, piezoelectric sensor, piezomechanical sensor, potentiometer, resistive bend sensor, variable-resistance sensor, electromyography (EMG) sensor, and Hall-effect sensor.

In an example, electromagnetic energy can be directed into an energy pathway at a first location and electromagnetic energy from the energy pathway can be measured from the energy pathway at a second location. In an example, electromagnetic energy can be directed into a wearable mesh, grid, lattice, or matrix of conductive pathways at a first location and received out from the mesh, grid, lattice, or matrix at a second location. In an example, electromagnetic energy can be directed into a wearable mesh, grid, lattice, or matrix of conductive pathways at a first vertex (or juncture of energy-conducting pathways) and received out from the mesh, grid, lattice, or matrix at a second vertex (or juncture of energy-conducting pathways). In an example, electromagnetic energy can be directed into a wearable mesh, grid, lattice, or matrix of conductive pathways at a first set of multiple location, vertexes, and/or pathway junctures and received out from the mesh, grid, lattice, or matrix at a second set of multiple location, vertexes, and/or pathway junctures In an example, electromagnetic energy can be transmitted into an energy pathway at a first location and electromagnetic energy from the energy pathway can be measured from the energy pathway at a second location. In an example, electromagnetic energy can be transmitted into a wearable mesh, grid, lattice, or matrix of conductive pathways at a first location and measured from the mesh, grid, lattice, or matrix at a second location. In an example, electromagnetic energy can be transmitted into a wearable mesh, grid, lattice, or matrix of conductive pathways at a first vertex (or juncture of energy-conducting pathways) and measured from the mesh, grid, lattice, or matrix at a second vertex (or juncture of energy-conducting pathways). In an example, electromagnetic energy can be transmitted into a wearable mesh, grid, lattice, or matrix of conductive pathways at a first set of multiple location, vertexes, and/or pathway junctures and measured from the mesh, grid, lattice, or matrix at a second set of multiple location, vertexes, and/or pathway junctures In an example, wearable energy pathways in a wearable mesh, grid, lattice, or matrix can comprise non-conductive or less-conductive fibers, traces, yarns, strands, or textiles which are coated, impregnated, or otherwise integrated with conductive material or particles. In an example, a non-conductive or less-conductive fiber, trace, yarn, strand, or textile can be selected from the group consisting of: acetate, acrylic, cotton, denim, elastane, Kevlar, latex, linen, Lycra, neoprene, nylon, nylon, polyester, wool, silicon rubber, silk, spandex, Danconn or rayon. In an example, conductive material or particles used for coating or impregnation can be selected from the group consisting of: aluminum or aluminum alloy; carbon nanotubes, graphene, or other carbon-based material; magnesium; ceramic particles; copper or copper alloy; gold; nickel; polyaniline; silver; and steel.

In an example, a wearable energy-conducting mesh, grid, lattice, or matrix can comprise one or more of the following: array of electroconductive members woven using a plain weave, rib weave, basket weave, twill weave, satin weave, leno weave, mock leno weave, or conan weave; array of fiber optic members woven using a plain weave, rib weave, basket weave, twill weave, satin weave, leno weave, mock leno weave; array of light-emitting fibers, threads, or yarns; array of sound-conducting members woven using a plain weave, rib weave, basket weave, twill weave, satin weave, leno weave, mock leno weave; array or mesh of electroconductive fibers; bendable fibers, threads, or yarns; bendable layer, trace, or substrate; elastic fibers, threads, or yarns; elastic layer, trace, or substrate; electroconductive fibers, threads, or yarns; electronically-functional bandage; electronically-functional tattoo; integrated array of electroconductive members; integrated array of fiber optic members; integrated array of sound-conducting members; interlaced electricity-conducting fibers, threads, or yarns; interlaced light-conducting fibers, threads, or yarns; interlaced sound-conducting fibers, threads, or yarns; light-emitting fibers, threads, or yarns; nonconductive fibers, threads, or yarns; nonconductive layer, substrate, or material; plaited fibers, threads, or yarns; sinusoidal fibers, threads, or yarns; stretchable fibers, threads, or yarns; stretchable layer, trace, or substrate; textile-based light display matrix; variable-resistance electroconductive fiber, thread, or yarn; variable-translucence fiber, thread, or yarn; water-resistant fibers, threads, or yarns; a layer or coating of metallic nanoparticles; a graphene layer; and water-resistant layer, trace, or substrate.

In an example, a wearable energy-conducting mesh, grid, lattice, or matrix can be incorporated into an article of clothing which is, in turn, worn over a body member containing a body joint. Changes in energy conducted through these pathways can be used to estimate joint motion and/or configuration. In an example, an array of energy pathways can be directly attached to a body member containing a body joint. In an example, energy pathways can be incorporated into an article of clothing or directly attached to a body member using one or more means selected from the group consisting of: adhesion, armband, article of clothing, bangle, belt, bracelet, buckle, button, clasp, clip, elastic band, elastic garment, eyewear, fabric layer, garment channel, garment pocket, gluing, hook, hook-and-eye attachment mechanism, incorporation into a bandage, incorporation into a tattoo, knitting, loop, magnetism, melting, metal fibers, nanoscale fibers, necklace, pin, polymer fibers, sewing, skin-adhesive patch, smart watch, snap, strands, strap, tape, textile channel, textile fibers, thermal bonding, tubular garment, waist band, weaving, wrist band, yarn, and zipper.

In an example, a wearable energy-conducting mesh, grid, lattice, or matrix can be incorporated into an article of clothing or clothing accessory selected from the group consisting of: an upper body garment such as a shirt, t-shirt, blouse, jacket, hoodie, sweatshirt, undershirt, brassier, girdle, blouse, or glove; a lower body garment such as a pair of pants, sweatpants, trousers, slacks, leggings, tights, underpants, pantyhose, shorts, or sock; a full-body garment such as a union suit, jump suit, pair of overalls, or dress; a clothing accessory such as shoe, boot, insole, hat, cap, headband, armband, strap, torso band, tubular accessory, wristband, other band, knee or elbow brace, back brace, knee or elbow pad, belt, bandage, electronic tattoo, or wearable patch.

In various examples, a wearable energy-conducting mesh, grid, lattice, or matrix can measure one or more joint configurations and/or motions selected from the group consisting of: eversion, extension, flexion, and/or inversion of the ankle; abduction, extension, flexion, lateral bending, and/or rotation of the spine; eversion, extension, flexion, and/or inversion of the elbow; extension and/or flexion of the finger or thumb; pronation, rotation, and/or supination of the forearm; abduction, adduction, extension, flexion, and/or rotation of the hip; extension and/or flexion of the jaw; abduction, adduction, extension, and/or flexion of the knee; eversion and/or inversion of the mid-tarsal; abduction, extension, flexion, and/or rotation of the neck; abduction, adduction, extension, flexion, and/or rotation of the shoulder; extension and/or flexion of the toe; and abduction, extension, flexion, and/or ulnar deviation or radial deviation of the wrist.

In an example, a wearable energy-conducting mesh, grid, lattice, or matrix can span the surface of the portion of the body containing one or more body joints selected from the group consisting of: ankle, elbow, finger, forearm, hip, jaw, knee, mid-tarsal, neck, shoulder, spine, thumb, toe, and wrist. In an example, a wearable energy-conducting mesh, grid, lattice, or matrix can span the surface of a body member containing the finger and thumb. In an example, a wearable energy-conducting mesh, grid, lattice, or matrix can span the surface of a body member containing the finger, forearm, thumb and wrist. In an example, a wearable energy-conducting mesh, grid, lattice, or matrix can span the surface of a body member containing the elbow, forearm and wrist.

In an example, a wearable energy-conducting mesh, grid, lattice, or matrix can span the surface of a body member containing an elbow. In an example, a wearable energy-conducting mesh, grid, lattice, or matrix can span the surface of the body containing an elbow, forearm, shoulder and spine. In an example, a wearable energy-conducting mesh, grid, lattice, or matrix can span the surface of a body member containing a hip and knee. In an example, a wearable energy-conducting mesh, grid, lattice, or matrix can span the surface of a body member containing the spine. In an example, a wearable energy-conducting mesh, grid, lattice, or matrix can span the surface of a body member containing an ankle, mid-tarsal and toe. In an example, a wearable energy-conducting mesh, grid, lattice, or matrix can span the surface of the portion of the body containing the neck, shoulder and spine.

In an example, an article of clothing or clothing accessory can be selected from the group consisting of: a shirt, a pair of shorts, a pair of pants, and a full-body suit. In an example, an article of clothing or wearable accessory can be selected from the group consisting of: ankle band, ankle tube, arm band, arm tube, belt, bra, collar, elbow pad, elbow tube, finger tube, girdle, glove, hip pad, hoodie, knee pad, knee tube, neck band, other wearable top, pair of pants, shirt, shoe, shorts, shoulder pad, shoulder tube, sock, suit, torso band, torso tube, underwear, union suit, waist band, and waist tube. In an example, energy pathway can be connected to an article of clothing or wearable accessory by a means selected from the group consisting of: weaving, knitting, and/or sewing; adhesion and/or gluing; hook-and-eye attachment mechanisms; snaps, buckles, straps, or clips; magnetic force; integration with threads, strands, yarns, elastic bands, textile fibers, polymer fibers, metal fibers, and/or nanoscale fibers; and connection by threads, strands, yarns, elastic bands, textile fibers, polymer fibers, metal fibers, and/or nanoscale fibers.

In an example, energy flow through or from different energy pathways in a wearable energy-conducting mesh, grid, lattice, or matrix can differ in one or more parameters selected from the group consisting of: total energy; energy flow per time period; energy power; wave amplitude; wave frequency; wave phase; waveform; frequency range; spectral distribution; resistance; voltage; current; impedance; and interval pattern.

In an example, Motion Recognition Clothing™ can also include a data control unit which further comprises one or more components selected from the group consisting of: a data processing component, a data communication component, a power source, a human-to-computer user interface, a computer-to-human interface, and a digital memory. In an example, a data control unit can be temporarily detached so that the remaining wearable portion of the invention can be washed. In an example, a data processing component can perform one or more functions selected from the group consisting of: amplify sensor signals, analyze data, analyze sensor information, convert analog signals to digital signals, determine a functional relationship between signal variation and joint angle variation, estimate joint angle, filter signals, model joint configuration, record data, run software applications, run software programs, and store data in memory.

In an example, a data communication component can perform one or more functions selected from the group consisting of: transmit and receive data via Bluetooth, WiFi, Zigbee, or other wireless communication modality; transmit and receive data to and from a mobile electronic device such as a cellular phone, mobile phone, smart phone, electronic tablet; transmit and receive data to and from a separate wearable device such as a smart watch or electronically-functional eyewear; transmit and receive data to and from the internet; send and receive phone calls and electronic messages; transmit and receive data to and from a home appliance and/or home control system; and transmit and receive data to and from an implantable medical device.

In an example, Motion Recognition Clothing™ can further comprise one or more motion-related sensors selected from the group consisting of: dual-axial accelerometer, tri-axial accelerometer, other multi-axial accelerometer, gyroscope, inclinometer or tilt sensor, goniometer, GPS or other location sensor, other inertial or motion sensor, goniometer, and kinematic sensor. In an example, Motion Recognition Clothing™ can further comprise one or more electromagnetic energy sensors selected from the group consisting of: electroencephalography (EEG) sensor, peripheral neurosensor, electromyography (EMG) sensor, Hall-effect sensor, electromagnetic field sensor, electrocardiogram (ECG) sensor, cardiac monitor, EOG sensor, galvanic skin response (GSR) sensor, impedance sensor, compass, magnometer, magnetic sensor, potentiometer, variable-resistance sensor, resistive bend sensor, piezoelectric sensor, piezomechanical sensor, piezoresistive sensor, and other electromagnetic sensor. Variations discussed elsewhere in this disclosure or in priority-linked disclosures can be applied to the example in this figure where relevant.

I claim:

1. A wearable device to measure the motion and/or configuration of a person's body comprising:

a wearable energy-conducting mesh, lattice, grid, or matrix that is configured to span the surface of a portion of a person's body which contains a joint, wherein the mesh, lattice, grid, or matrix further comprises a plurality of energy pathways;
a plurality of energy input components which direct energy into the energy pathways at a first plurality of locations;
a plurality of energy sensors which measure energy flow through the energy pathways from a second plurality of locations;
wherein data from the energy sensors are analyzed in order to measure the motion and/or configuration of the body joint;
wherein there is a first energy pathway in the plurality of energy pathways and there is a second energy pathway in the plurality of energy pathways; and
wherein the first energy pathway has a first amount of longitudinal curvature or convolution, the second energy pathway has a second amount of longitudinal curvature or convolution, and the second amount is greater than the first amount.

2. A wearable device to measure the motion and/or configuration of a person's body comprising:

a wearable energy-conducting mesh, lattice, grid, or matrix that is configured to span the surface of a portion of a person's body which contains a joint, wherein the mesh, lattice, grid, or matrix further comprises a plurality of energy pathways;
a plurality of energy input components which direct energy into the energy pathways at a first plurality of locations;
a plurality of energy sensors which measure energy flow through the energy pathways from a second plurality of locations;
wherein data from the energy sensors are analyzed in order to measure the motion and/or configuration of the body joint;
wherein there is a first energy pathway in the plurality of energy pathways and there is a second energy pathway in the plurality of energy pathways; and
wherein the first energy pathway has a first sinusoidal shape with a first phase, the second energy pathway has a second sinusoidal shape with a second phase, and the first phrase is different than the second phase.

* * * * *